US006872748B2

(12) United States Patent
Lee

(10) Patent No.: US 6,872,748 B2
(45) Date of Patent: Mar. 29, 2005

(54) SIMPLIFIED RESINIFERATOXIN ANALOGUES AS VANILLOID RECEPTOR AGONIST SHOWING EXCELLENT ANALGESIC ACTIVITY AND THE PHARMACEUTICAL COMPOSITIONS CONTAINING THE SAME

(75) Inventor: Jee Woo Lee, Seoul (KR)

(73) Assignee: Digital Biotech Co., Ltd. (KR)

( * ) Notice: Subject to any disclaimer, the term of this patent is extended or adjusted under 35 U.S.C. 154(b) by 0 days.

(21) Appl. No.: 10/324,393

(22) Filed: Dec. 18, 2002

(65) Prior Publication Data

US 2004/0063786 A1 Apr. 1, 2004

Related U.S. Application Data

(63) Continuation of application No. PCT/KR02/01746, filed on Sep. 18, 2002, now abandoned.

(30) Foreign Application Priority Data

Sep. 27, 2001 (KR) ................................ 10-2001-0060028
Sep. 16, 2002 (KR) ................................ 10-2002-0056280

(51) Int. Cl.[7] ........................ A01N 37/02; A01N 37/06; A61K 31/225; C07C 67/02
(52) U.S. Cl. ........................................ 514/548; 560/255
(58) Field of Search ........................... 560/255; 514/548

(56) References Cited

U.S. PATENT DOCUMENTS 6,476,076 B1 * 11/2002 Lee et al. ................... 514/580

OTHER PUBLICATIONS

Vanilloid (Capsaicin) Receptors & Mechanisms; A. Szallashi, et al., Vol. 51, #2, Pharmacological Reviews, pp. 159–211.

Capsaicin–Induced Ion Fluxes in Dorsal Root Ganglion Cells In Culture, JN Wood et al, The Journal of Neuroscience, Sep. 1988, 8(9): 3208–3220.

The capsaicin receptor: a heat–activated ion channel in the pain pathway; MJ Caterina et al., Nature:vol. 389: Oct. 23, 1997, pp. 816–824.

The Cloned Capsaicin Receptor Integrates Multiple Pain–Producing Stimuli, M.Tominaga et al., Neuron, vol. 21, 531–543, Sep. 1998.

Impaired Nociception & Pain Sensation in Mice Lacking the Capsaicin Receptor, MJ Caterina et al., Apr. 14, 2000, vol. 288 Science, pp. 306–313.

Vanilloid receptor–1 is essential for inflammatory thermal hyperalgesia, Letters to Nature, vol. 405, May 11, 2000, pp. 183–187.

3–Acyloxy–2–phenalkylpropyl Amides & Esters of Homovanillic Acid as Novel Vanilloid Receptor Agonists, Bioorganic & Medicinal Chemistry Letters 9 (1999) 2909–2914.

Capsaicin–like agonists, R. Wrigglesworth et al., Drugs of the Future 1998, 23(5): 531–538.

* cited by examiner

*Primary Examiner*—Richard L. Raymond
*Assistant Examiner*—Zachary C. Tucker
(74) *Attorney, Agent, or Firm*—Anderson Kill & Olick, PC

(57) ABSTRACT

The present invention is related to new vanilloid analogues containing resiniferatoxin pharmacophores, pharmaceutical compositions that have such analogues, and their uses as vanilloid receptor agonists and potent analgesics. The present invention provides a pharmaceutical composition for preventing, alleviating or treating pain, acute pain, chronic pain, neuropathic pain, post-operative pain, migraine, arthralgia, neutopathies, nerve injury, diabetic neuropathy, neurodegeneration, neurotic skin disorder, stroke, urinary bladder hypersensitiveness, irritable bowel syndrome, a respiratory disorder such as asthma or chronic obstructive pulmonary disease, irritation of skin, eye or mucous membrane, fervescence, stomach-duodenal ulcer, inflammatory bowel disease, inflammatory disease or urgent urinary incontinence.

11 Claims, No Drawings

SIMPLIFIED RESINIFERATOXIN ANALOGUES AS VANILLOID RECEPTOR AGONIST SHOWING EXCELLENT ANALGESIC ACTIVITY AND THE PHARMACEUTICAL COMPOSITIONS CONTAINING THE SAME

CROSS REFERENCE TO RELATED APPLICATION

This application is a continuation patent application of PCT Patent Application No. PCT/KR02/01746, which was filed on Sep. 18, 2002, designating the United States of America, now abandoned.

FIELD OF THE INVENTION

The present invention relates to vanilloid analogues containing resiniferatoxin pharmacophores, pharmaceutical compositions comprising such analogues, and methods of using such analogues as vanilloid receptor agonists and potent analgesics.

BACKGROUND OF THE INVENTION

As diseases associated with the activity of vanilloid receptor, pain, acute pain, chronic pain, neuropathic pain, post-operative pain, migraine, arthralgia, neuropathies, nerve injury, diabetic neuropathy, neurodegeneration, neurotic skin disorder, stroke, urinary bladder hypersensitiveness, irritable bowel syndrome, a respiratory disorder such as asthma or chronic obstructive pulmonary disease, irritation of skin, eye or mucous membrane, fervescence, stomach-duodenal ulcer, inflammatory bowel disease and inflammatory diseases can be enumerated. The present invention provides pharmaceutical compositions for prevention or treatment of these diseases. Yet, the diseases described above are only for enumeration, not to limit the scope of clinical application of vanilloid receptor agonist.

Capsaicin(8-methyl-N-vanillyl-6-nonenamides; CAP) is a main pungent component in hot pepper. Hot pepper has been used, for a long time, not only as a spice but also as a traditional medicine in the treatment of gastric disorders and when applied locally, for the relief of pain and inflammation (Szallasi and Blumberg, *Pharm. Rev.,* 51, pp159–211, 1999. CAP has a wide spectrum of biological actions, and not only exhibits effects on the cardiovascular and respiratory systems but also induces pain and irritancy on local application. CAP, however, after such induction of pain, induces desensitization, both to CAP itself and also to other noxious stimuli to make the pain stopped. Based on this property, CAP and its analogues such as olvanil, nuvanil, DA-5018, SDZ-249482, resiniferatoxin are either used as analgesic agent, therapeutic agent for incontinentia urinae or skin disorder, or under development (Wriggleworth and Walpore, *Drugs of the Future*, 23, pp531–538, 1998).

Transmissions of mechanical, thermal and chemical noxious stimuli are mainly occurred by primary afferent nerve fibers of fine unmyelinated nerve(C-fiber) and thin myelinated nerve(A-fiber), and main reaction site of CAP and its analogues called vanilloid is present at the nerve fiber transmitting the noxious stimuli. CAP acts at the receptor existing on these neurons to induce potent stimuli by causing potent inflow of mono-acid and di-valent cations such as calcium and sodium, then exhibits potent analgesic effect by blocking the nervous function (Wood et al.; *J. Neurosci*., 8, pp3208–3220, 1988). Vanilloid receptor-1(VR) has been recently cloned and its existences becomes clear (Caterina et al.; *Nature,* 389, pp816–824, 1997). It was clarified that this receptor transmits not only stimuli by CAP analogues (vanilloid) but also various noxious stimuli such as proton and thermal stimuli (Tominaga et al.; *Neuron,* 21, pp513–543, 1998). Based on this, it is considered that VR functions as a integrative modulator against various noxious stimuli and carries out critical role in transmissions of pain and noxious stimuli. Recently, knock-out mouse in which gene encoding for vanilloid receptor was deleted was prepared (Caterinal et al.; *Science,* 288, pp306–313, 2000: Davis et al.; *Nature,* 405, pp183–187, 2000). Compared to normal mice, the mouse was found out to exhibit much reduced reaction to thermal stimuli and thermal pain, while exhibiting no difference in general behavior, reconfirming the importance of the receptor in transmission of noxious signal. However, except proton, no other endogenous ligand, not exogenous ligand such as CAP, actually involved in transmission of noxious stimuli at VR was known.

VR (or CAP receptor) is a specific neuronal membrane recognition site for CAP and related irritant compounds. It is expressed almost exclusively by primary sensory neurons involved in nociception and neurogenic inflammation. The receptor functions as a cation-selective ion channel with a preference for calcium, and its functional subtype, VR-1, activated by both CAP and noxious heat has recently been cloned. Its desensitization caused by specific ligands has been recognized as a promising therapeutic approach to mitigate neuropathic pain and other pathological conditions in which neuropeptides released from primary sensory neurons play a crucial role.

Most exogenous VR agonists which are being developed or used as analgesics are structually related to CAP (i.e., Zostrix™, Olvanil™, SDZ-249482™, and DA-5018™) and resiniferatoxin. Their structures include a common vanilloid ring which appears to be important for agonist activity. However, in a recent report, it was demonstrated that compounds lacking the vanilloid moiety, such as sesquiterpenoid unsaturated dialdehydes or triprenyl phenol, may also activate the receptor. Although receptor antagonists are fewer, several compounds such a capsazepine, which acts competitively at the CAP binding site, the channel blocker ruthenium red and capsazocaine have been reported.

Resiniferatoxin (RTX), a tricyclic diterpene isolated from *Euphorbia resinifera*, has been regarded as an ultrapotent CAP analogue. Indeed, the specific binding of RTX to the CAP binding site in dorsal root ganglia has been demonstrated with labeled [$^3$H]RTX. RTX is being developed as an ultrapotent sensory neuron desensitizing agent for the treatment of urinary urge incontinence and the pain assoaciated with diabetic neuropathy. Recently, a totally enantiocontrolled synthesis and a conformational analysis of RTX have been reported. However, the pharmacophoric groups of RTX have not yet been clearly defined, although structure-activity studies suggest that the $C_{20}$-homovanillic moiety, the $C_3$-keto group, and the ortho-ester phenyl group on ring C are crucial structural elements responsible for the extremely high potency of RTX. The lower potency of CAP relative to RTX, on the other hand, may be rationalized by the lack of some of these critical pharmacophoric groups, especially $C_3$-keto group.

U.S. Pat. No. 4,939,149 discloses a method for desensitizing a subject animal by administering a therapeutically effective desensitizing amount of RTX for desensitizing the animal to neurogenic inflammation, to chemically and thermally induced pain and to responses involving sensory afferent pathways sensitive to CAP.

Although a number of vanilloid agonist based on the structures of CAP and RTX have been reported as potential analgesics (e.g., U.S. Pat. No. 5,021,450 discloses homovanillyl diterpene derivatives such as 12-deoxyphorbol 13-phenylacetate 20-homovanillate and mezerein 20-homovanillate as mimics of RTX), these CAP-like analogues are limited by their intrinsic lower potency and narrow therapeutic index. RTX, on the other hand, is of limited availability from natural sources and is difficult to obtain synthetically due to its structural complexity.

The present inventors have made extensive researches to discover novel analgesic agents based on the VR, which has simpler structure than RTX or known RTX- or CAP-like analogues. As results thereof, KP348819 which we invented, disclosed that the new compounds having modifications on $C_{20}$-homovanillic moiety, the $C_3$-carbonyl, and the ortho-ester phenyl moiety as essential groups for recognition and binding showed potent VR agonist activity in terms of the receptor binding assay and the CAP-activated single channels assay (Lee et al.; *Bioorganic & Medicinal Chemistr. Letters*, pp2909–2914, 1999). And KPA2000-0048385 which we invented, disclosed that new compounds having modifications on 4-methane sulphone amido instead of 4-hydroxy-3-methoxy phenyl moiety as essential groups for recognition and binding based on the VR showed different receptor agonist activity.

The present invention is to provide novel compounds having modifications on thiocarbamate moiety, the 3-acyloxy2-benzylpropyl, the 4-t-butylbenzyl, and the 4-hydroxy-3-methoxy moiety as essential groups for recognition and binding showed potent VR receptor agonist activity in terms of the receptor binding assay and exhibit analgesic and anti-inflammatory effects while causing no irritancy, and pharmaceutical compositions containing the same.

SUMMARY OF THE INVENTION

Thus, the present invention provides novel compounds represented by the following formula (I):

(I)

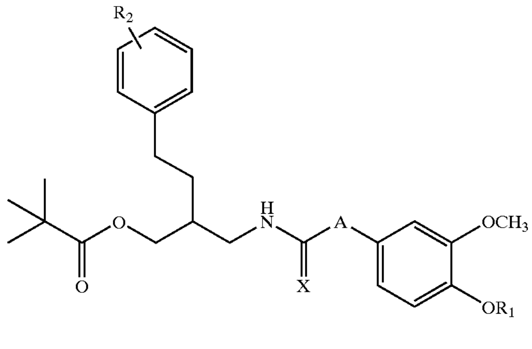

wherein,

X is an oxygen or sulfur atom;

A is —$NHCH_2$— or —$CH_2$—;

$R_1$ is a hydrogen atom, an aminoethyl or an alkoxyalkyl group having 1 to 6 carbon atoms;

$R_2$ is a hydrogen or halogen atom or alkyl group having 1 to 6 carbon atoms.

And, the present invention provides novel compounds represented by the following formula (II):

(II)

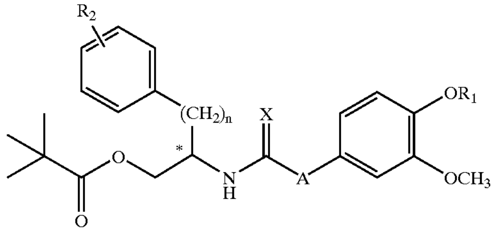

wherein,

X is an oxygen or sulfur atom;

A is —$NHCH_2$— or —$CH_2$—;

$R_1$ is a hydrogen atom, an aminoethyl or an alkoxyalkyl group having 1 to 6 carbon atoms;

$R_2$ is a hydrogen or halogen atom or alkyl group having 1 to 6 carbon atoms;

n is an integer of 1 to 3;

the asteric mark * indicates a chiral carbon atom, and their pharmaceutically acceptable salts.

And, the present invention provides novel compounds represented by the following formula (III).

(III)

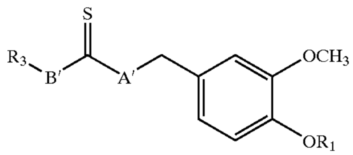

wherein,

A' and B' are oxygen or nitrogen atom;

$R_1$ is a hydrogen atom, an aminoethyl or an alkoxyalkyl group having 1 to 6 carbon atoms;

(III-1)

$R_3$ is 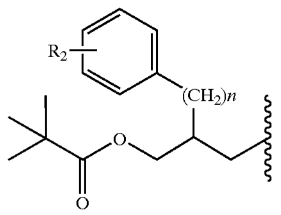 or (III-2)

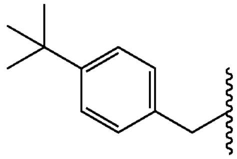 ;

$R_2$ is a hydrogen or halogen atom or alkyl group having 1 to 6 carbon atoms;

n is an integer of 1 to 3;

excluded that A' and B' is oxygen or nitrogen atoms simultaneously.

The present invention also provides pharmaceutical compositions comprising the compound (I), (II) or (III) as an active ingredient in an amount effective to alleviate pain, together with a pharmaceutically acceptable carrier.

The present invention also provides a use of the compounds as an active ingredient in medicines for treating pain or analgesic medicines.

The present invention still provides processes for preparing the compound (I), (II) and (III).

DETAILED DESCRIPTION

A novel compound of the present invention is represented by the following formula (I):

(I)

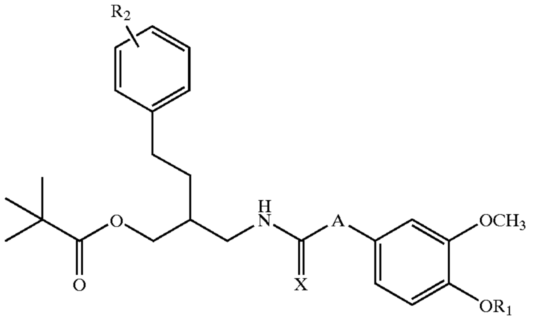

wherein,

X is an oxygen or sulfur atom;

A is $—NHCH_2—$ or $—CH_2—$;

$R_1$ is a hydrogen atom, an aminoethyl or an alkoxyalkyl group having 1 to 6 carbon atoms;

$R_2$ is a hydrogen or halogen atom or alkyl group having 1 to 6 carbon atoms.

The preferred compounds may be represented by the following formula (I-a) to (I-c):

(I-a)

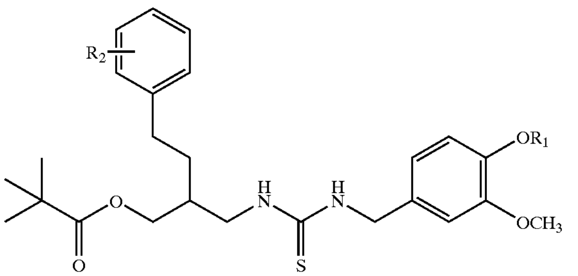

(I-b)

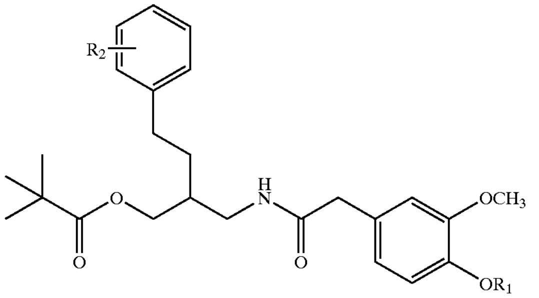

-continued (I-c)

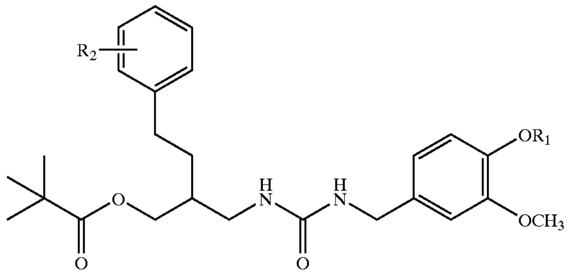

wherein, $R_1$ and $R_2$ have the same meanings as defined above.

In a preferred embodiment, the compounds have general formula (I-a) wherein X is sulfur atom; A is $—NHCH_2—$; $R_1$ is hydrogen atom or aminoethyl group; $R_2$ is an hydrogen or halogen atom or an alkyl group having 1 to 6 carbon atoms.

In a preferred embodiment, the compounds have the general formula (I-b) wherein X is oxygen atom; A is $—CH_2—$; $R_1$ is hydrogen atom or aminoethyl group; $R_2$ is an hydrogen or halogen atom or an alkyl group having 1 to 6 carbon atoms.

In a preferred embodiment, the compounds have the general formula (I-c) wherein X is oxygen atom; A is $—NHCH_2—$; $R_1$ is hydrogen atom or aminoethyl group; $R_2$ is an hydrogen or halogen atom or an alkyl group having 1 to 6 carbon atoms.

In a preferred embodiment, the preferred compound is one selected from the group consisting of N-[4-(3,4-dimethylphenyl)-2-(pivaloyloxymethyl)butyl]-N-[4-hydroxy-3-methoxybenzyl]thiourea, N-[4-t-bytulphenyl-2-(pivaloyloxymethyl)butyl]-N-[4-hydroxy-3-methoxybenzyl]thiourea, N-[4-(3,4-dimethylphenyl)-2-(pivaloyloxymethyl)butyl]-N-[4-hydroxy-3-methoxybenzyl]urea, N-[4-t-dimethylphenyl-2-(pivaloyloxymethyl)butyl]-N-[4-hydroxy-3-methoxybenzyl]urea, N-[4-(3,4-dimentylphenyl-2-(pivaloyloxymethyl)butyl)-2-[4-hydroxy-3-methoxyphenyl]acetamide, N-[4-(4-t-butylphenyl)-2-(pivaloyloxymethyl)butyl]-2-[4-hydroxy-3-methoxyphenyl]acetamide, N-[4-(3,4-dimethylphenyl)-2-(pivaloyloxymethyl)butyl]-2-[4-(2-aminoethoxy)-3-methoxyphenyl]acetamide, N-[4-(4-t-butylphenyl)-2-(pivaloyloxymethyl)butyl]-2-[4-(2-aminethoxy)-3-methoxyphenyl]acetamide.

And a novel compound of the present invention is represented by the following formula (II):

(II)

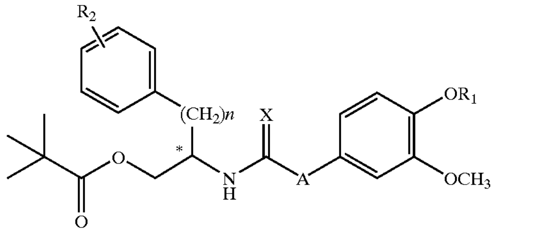

wherein,

X is an oxygen or sulfur atom;

A is —$NHCH_2$— or —$CH_2$—;

$R_1$ is a hydrogen atom, an aminoethyl or an alkoxyalkyl group having 1 to 6 carbon atoms;

$R_2$ is a hydrogen or halogen atom or alkyl group having 1 to 6 carbon atoms;

n is an integer of 1 to 3;

the asteric mark * indicates a chiral carbon atom, and their pharmaceutically acceptable salts.

The preferred compounds may be represented by the following formula (II-a) to (II-c):

(II-a)

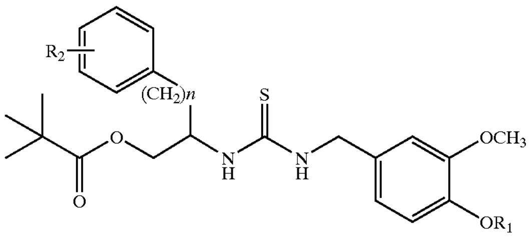

(II-b)

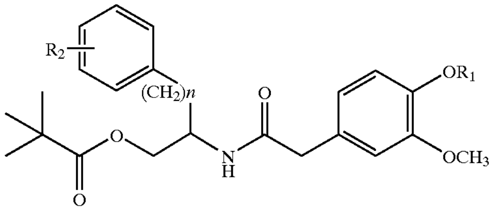

(II-c)

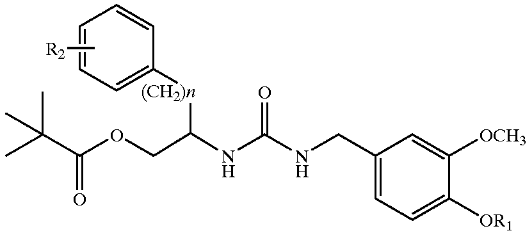

wherein, $R_1$ and $R_2$ have the same meanings as defined above.

In a preferred embodiment, the compounds have general formula (II-a) wherein X is sulfur atom; A is —$NHCH_2$—; $R_1$ is hydrogen atom or aminoethyl group; $R_2$ is an hydrogen or halogen atom or an alkyl group having 1 to 6 carbon atoms; n is an integer of 1 or 2.

In a preferred embodiment, the compounds have general formula (II-b) wherein X is oxygen atom; A is —$CH_2$—; $R_1$ is hydrogen atom or aminoethyl group; $R_2$ is an hydrogen or halogen atom or an alkyl group having 1 to 6 carbon atoms; n is an integer of 1 or 2.

In a preferred embodiment, the compounds have general formula (II-c) wherein X is oxygen atom; A is —$NHCH_2$—; $R_1$ is hydrogen atom or aminoethyl group; $R_2$ is an hydrogen or halogen atom or an alkyl group having 1 to 6 carbon atoms; n is an integer of 1 or 2.

In a preferred embodiment, the preferred compound is one selected from the group consisting of N-[3-(3,4-dimethylphenyl)-1-pivaloyloxy-2-propyl]-N-[4-hydroxy-3-methoxybenzyl]thiourea, N-3-(4-t-butylphenyl)-1-pivaloyloxy-2-propyl]-N-[4-hydroxy-3-methoxybenzyl]thiourea, N-[4-(3,4-dimethylphenyl)-1-pivaloyloxy-2-butyl]-N-[4-hydroxy-3-methoxybenzyl]thiorea, N-[3-(3,4-dimethylphenyl)-1-pivaloyloxy-2-propyl]-N-[4-hydroxy-3-methoxybenzyl]urea, N-[3-(4-t-dimethylphenyl)-1-pivaloyloxy-2-propyl]-N-[4-hydroxy-3-methoxybenzyl]urea N-[4-(3,4-dimethylphenyl)-1-pivaloyloxy-2-butyl]-N-[4-hydroxy-3-methoxybenzyl]urea, N-[3-(3,4-dimethylphenyl)-1-pivaloyloxy-2-propyl]-N-[4-(2-aminoethoxy)3-methoxybenzyl]thiourea, N-[3-(4-t-dimethylphenyl)-1-pivaloyloxy-2-propyl]-N-[4-(2-aminoethoxy)3-methoxybenzyl]thiourea, N-[4-(3,4-dimethylphenyl)-1-pivaloyloxy-2-propyl]-N-[4-(2-aminoethoxy)3-methoxybenzyl]thiourea, N-[3-(3,4-dimethylphenyl)-1-pivaloyloxy-2-propyl]-N-[4-(2-aminoethoxy)3-methoxybenzyl]urea, N-[3-(4-t-dimethylphenyl)-1-pivaloyloxy-2-propyl]-N-[4-(2-aminoethoxy)3-methoxybenzyl]urea, N-[4-(3,4-dimethylphenyl)-1-pivaloyloxy-2-propyl]-N-[4-(2-aminoethoxy)3-methoxybenzyl]urea, N-[3-(3,4-dimethylphenyl)-1-pivaloyloxy-2-propyl]-2-[4-hydroxy-3-methoxyphenyl]acetamide, N-[3-(4-t-dimethylphenyl)-1-pivaloyloxy-2-propyl]-2-[4-hydroxy-3-methoxyphenyl]acetamide, N-[4-(3,4-dimethylphenyl)-1-pivaloyloxy-2-propyl]-2-[4-hydroxy-3-methoxyphenyl]acetamide, N-[3-(3,4-dimethylphenyl)-1-pivaloyloxy-2-propyl]-2-[4-(2-aminoethoxy)-3-methoxyphenyl]acetamide, N-[3-(4-t-dimethylphenyl)-1-pivaloyloxy-2-propyl]-2-[4-(2-aminoethoxy)-3-methoxyphenyl]acetamide, N-[4-(3,4-dimethylphenyl)-1-pivaloyloxy-2-propyl]-2-[4-(2-aminoethoxy)-3-methoxyphenyl]acetamide, N-[(2R)-3-phenyl-1-pivaloyloxy-2-propyl]-N-[4-hydroxy-3-methoxybenzyl]thiourea, N-[(2S)-3-phenyl-1-pivaloyloxy-2-propyl]-N-[4-hydroxy-3-methoxybenzyl]thiourea, N-[(2R)-3-phenyl-1-pivaloyloxy-2-propyl]-N-[4-hydroxy-3-methoxybenzyl]urea, N-[(2S)-3-phenyl-1-pivaloyloxy-2-propyl]-N-[4-hydroxy-3-methoxybenzyl]urea, N-[(2R)-3-phenyl-1-pivaloyloxy-2-propyl]-N-[4-(2-aminoethoxy)-3-methoxybenzyl]thiourea, N-[(2S)-3-phenyl-1-pivaloyloxy-2-propyl]-N-[4-(2-aminoethoxy)-3-methoxybenzyl]thiourea, N-[(2R)-3-phenyl-1-pivaloyloxy-2-propyl]-N-[4-(2-aminoethoxy)-3-methoxybenzyl]urea, N-[(2S)-3-phenyl-1-pivaloyloxy-2-propyl]-N-[4-(2-aminoethoxy)-3-methoxybenzyl]urea, N-[(2R)-3-phenyl-1-pivaloyloxy-2-propyl]-2-[4-hydroxy-3-methoxyphenyl]acetamide, N-[(2S)-3-phenyl-1-pivaloyloxy-2-propyl]-2-[4-hydroxy-3-methoxyphenyl]acetamide, N-[(2R)-3-phenyl-1-pivaloyloxy-2-propyl]-2-[4-(2-aminoethoxy)-3-methoxyphenyl]acetamide, N-[(2S)-3-phenyl-1-pivaloyloxy-2-propyl]-2-[4-(2-aminoethoxy)-3-methoxyphenyl]acetamide.

And a novel compounds of the present invention is represented by the following formula (III):

(III)

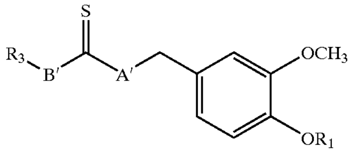

wherein,

A' and B' are oxygen or nitrogen atom;

$R_1$ is a hydrogen atom, an aminoethyl or an alkoxyalkyl group having 1 to 6 carbon atoms;

(III-1)

$R_3$ is

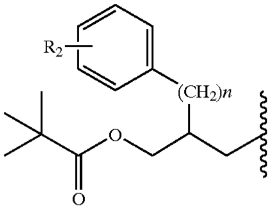

or (III-2)

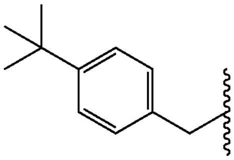

$R_2$ is a hydrogen or halogen atom or alkyl group having 1 to 6 carbon atoms;

n is an integer of 1 to 3;

provided that both of A' and B' are not oxygen atom or nitrogen atom simultaneously.

The preferred compounds may be represented by the following formula (III-a) to (III-d):

(III-a)

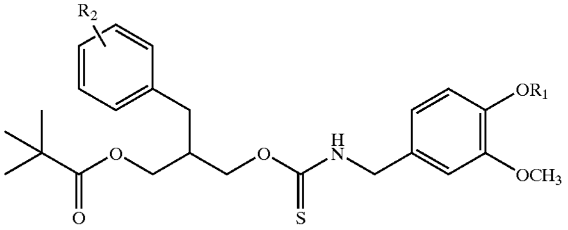

(III-b)

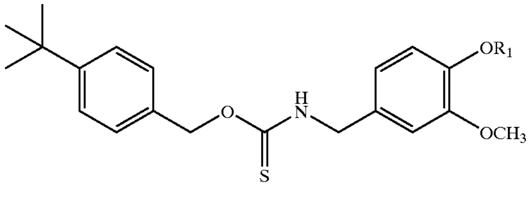

-continued (III-c)

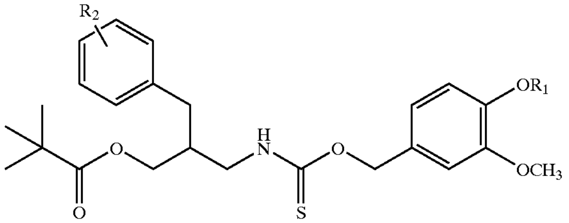

(III-d)

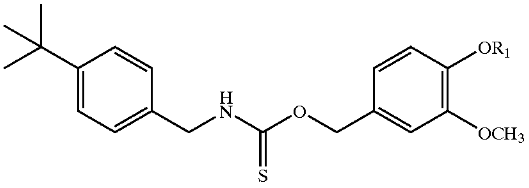

wherein, $R_1$ and $R_2$ have the same meanings as defined above.

In a preferred embodiment, the compounds have general formula (III-a) wherein A' is nitrogen atom; B' is oxygen atom; $R_1$ is hydrogen atom or aminoethyl group; $R_3$ is the group of formula (III-1) wherein $R_2$ is an hydrogen or halogen atom or an alkyl group having 1 to 6 carbon atoms; n is an integer of 1 or 2.

In a preferred embodiment, the compounds have general formula (III-b) wherein A' is nitrogen atom; B' is oxygen atom; $R_1$ is hydrogen atom or aminoethyl group; $R_3$ is the group of formula (III-2).

In a preferred embodiment, the compounds have general formula (III-c) wherein A' is oxygen atom; B' is nitrogen atom; $R_1$ is hydrogen atom or aminoethyl group; $R_3$ is the group of formula (III-1) wherein $R_2$ is an hydrogen or halogen atom or an alkyl group having 1 to 6 carbon atoms; n is an integer of 1 or 2.

In a preferred embodiment, the compounds have general formula (III-d) wherein A' is oxygen atom; B' is nitrogen atom; $R_1$ is hydrogen atom or aminoethyl group; $R_3$ is the group of formula (III-2).

In a preferred embodiment, the preferred compound is one selected from the group consisting of O-[2-(3,4-diemethylbenzyl)-3-(pivaloyloxy)propyl]-N-(4-hydroxy-3-methoxybenzyl)thiocarbamate, O-[2-(4-t-butylbenzyl)-3-(pivaloyloxy)propyl]-N-(4-hydroxy-3-methoxybenzyl)thiocarbamate, O-[2-(3,4-dimethylbenzyl)-3-(pivaloyloxy)propyl]-N-[4-(2-aminoethoxy)-3-methoxybenzyl]thiocarbamate, O-[2-(4-t-butylbenzyl)-3-(pivaloyloxy)propyl]-N-[4-(2-aminoethoxy)-3-methoxybenzyl]thiocarbamate, O-(4-t-butylbenzyl)-N-(4-hydroxy-3-methoxybenzyl) thiocarbamate, O-(4-t-butylbenzyl)-N-[4-(2-aminoethoxy)-3-methoxybenzyl]thiocarbamate, N-[2-(3,4-dimethylbenzyl)-3-(pivaloyloxy)propyl]-O-(4-hydroxy-3-methoxybenzyl)thiocarbamate, N-[2-(4-t-butylbenzyl)-3-(pivaloyloxy)propyl]-O-(4-hydroxy-3-methoxybenzyl)thiocarbamate, N-[2-(3,4-dimethylbenzyl)-3-(pivaloyloxy)propyl]-O-[4-(2-aminoethoxy)-3-methoxybenzyl]thiocarbamate, N-[2-(4-t-butylbenzyl)3-(pivaloyloxy)propyl]-O-[4-(2-aminoethoxy)-3-methoxybenzyl]thiocarbamate, N-(4-t-butylbenzyl)-O-(4-hydroxy-3-methoxybenzyl) thiocarbamate, N-(4-t-butylbenzyl)-O-[4-(2-aminoethoxy)-3-methoxybenzyl]thiocarbamate.

In all cases, the compound of formula (I), (II) or (III) may be in racemic mixture, or in R or S stereoisomer. And, the present invention encompasses the compound (I), (II) and (E) in the form of their pharmaceutically acceptable salts.

The compounds of the invention may be chemically synthesized by the methods in the reaction schemes hereinafter, which are merely exemplary and in no way limit the invention. The reaction schemes show the steps for preparing the representative compounds of the present invention, and other compounds also may be produced by following the steps with appropriate modifications of reagents and starting materials, which are envisaged by those skilled in the art.

SCHEME 1

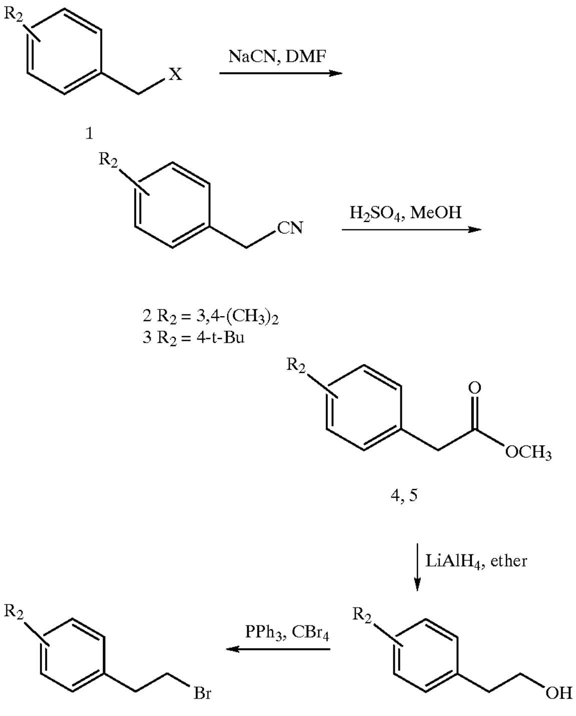

1

2 $R_2$ = 3,4-$(CH_3)_2$
3 $R_2$ = 4-t-Bu 4, 5

6, 7

8, 9

As depicted in above Scheme 1, benzyl chloride derivative 1 was reacted with cyanate reagents, e.g., sodium cyanate to synthesize compounds 2 and 3, and then reacted with alcohols, e.g., methanol under acidic conditions, to synthesize compound 4 and 5. Ester group of compound 4, 5 was reacted with reducing agents such as $LiAlH_4$ to produce alcohol, and then bromo derivatives 8 and 9 were synthesized by using $PPh_3$ and $CBr_4$ as a bromine provider, according to Mitsunobu reaction.

SCHEME 2

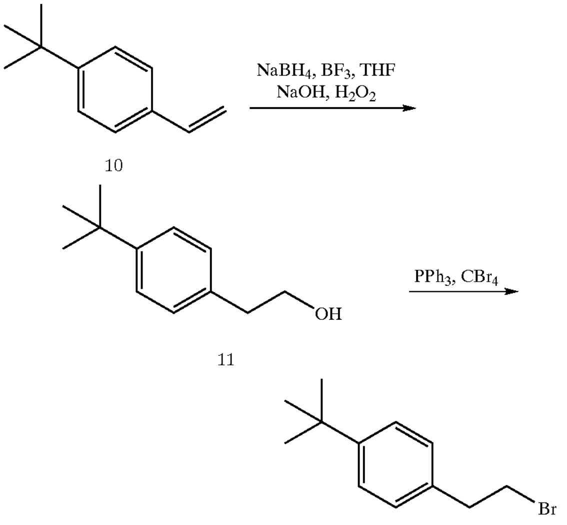

10

11

12

As depicted in the above Scheme 2, the compound of formula (In) which $R_3$ group is (III-2), was synthesized by using a butyl stylben derivative 10 as a starting material. Compound 10 was reacted with boronating agents, e.g., trifluoroboron, and hydrolyzed to synthesize compound 11 with hydroxy group. And then compound 12 was synthesized by using $PPh_3$ and $CBr_4$ as a bromine provider, according to Mitsunobu reaction.

SCHEME 3

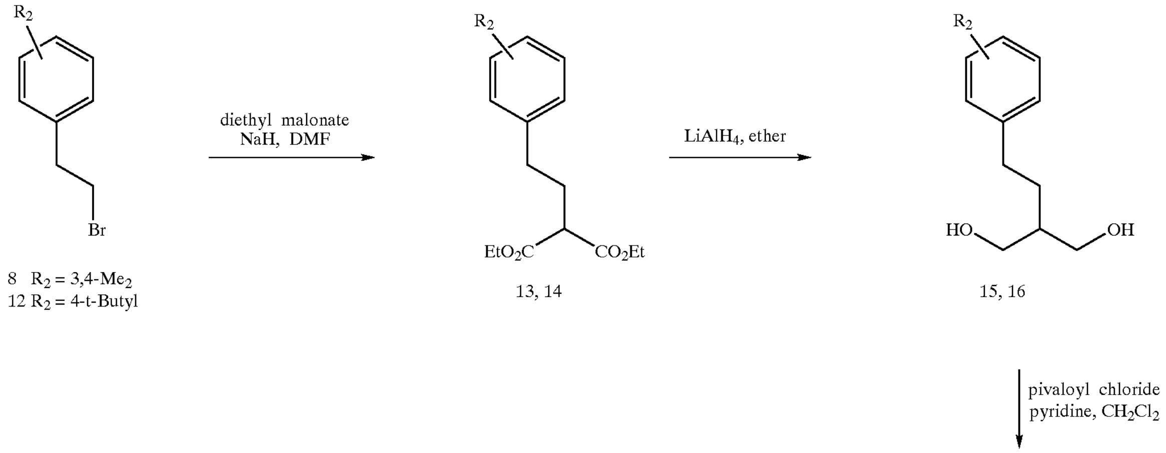

8 $R_2$ = 3,4-$Me_2$
12 $R_2$ = 4-t-Butyl 13, 14

15, 16

-continued

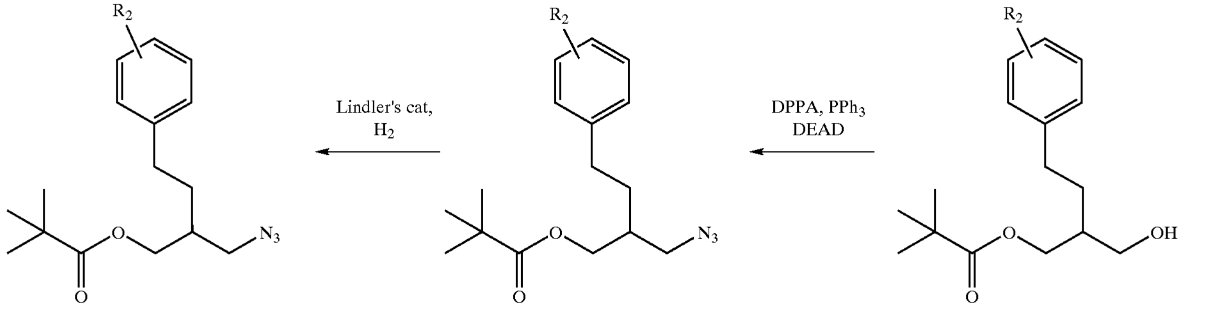

21, 22 19, 20 17, 18

As depicted in the above Scheme 3, monoalkylation of diethyl malonate with Bromo derivatives 8 and 12, followed by $LiAlH_4$-reduction, produced the corresponding diols 15 and 16. Monoesterification of compounds 15 and 16 with pivaloylating agents, e.g., pivaloyl chloride under basic conditions, produced the corresponding pivaloyls 17 and 18. Conversion of the remaining alcohol function to an azide, and followed by $LiAlH_4$-reduction, produced the corresponding amines 21 and 22.

SCHEME 4

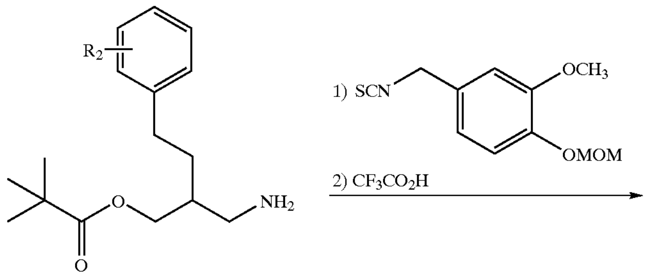

21 ,22

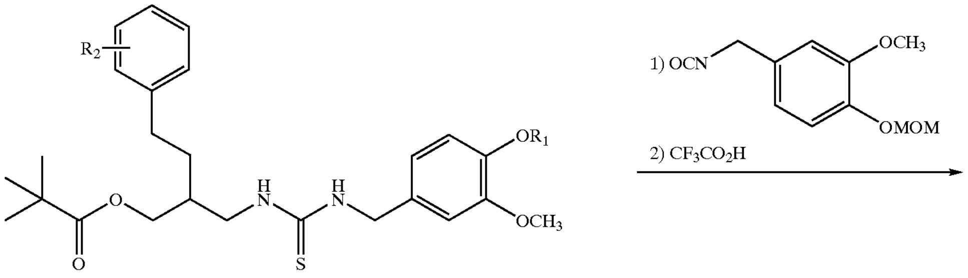

26, 27 $R_1$ = MOM
28, 29 $R_1$ = H

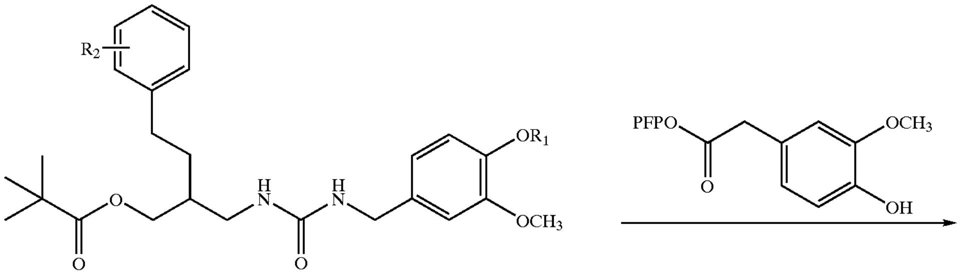

30, 31 $R_1$ = MOM
32, 33 $R_1$ = H

-continued

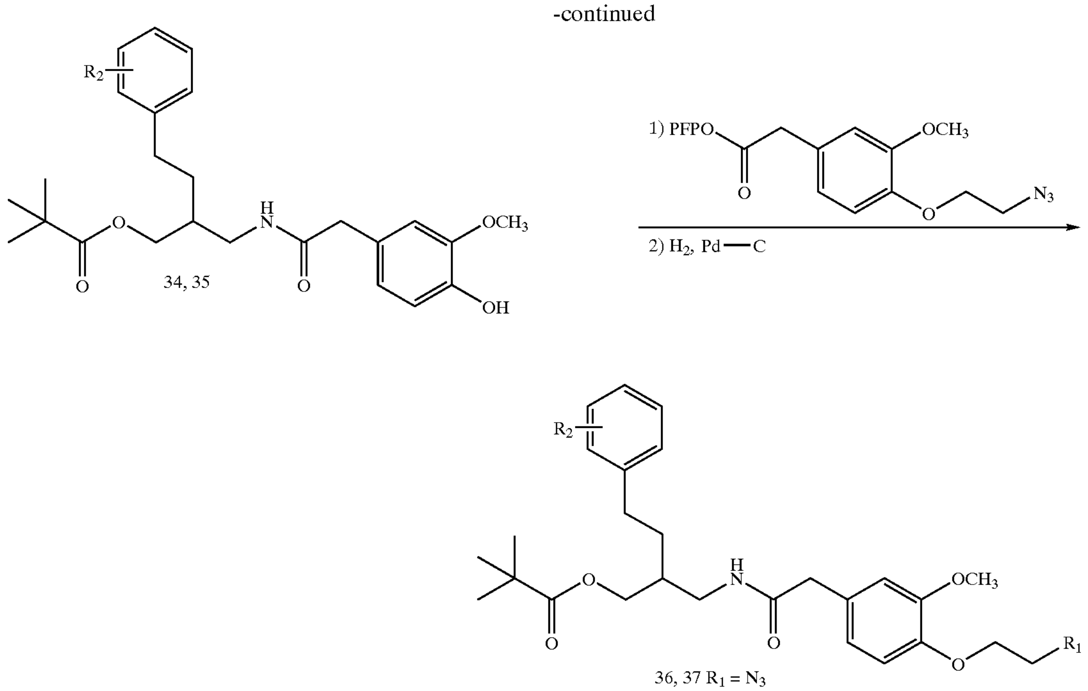

34, 35

36, 37 $R_1 = N_3$
38, 39 $R_1 = NH_2$

As depicted in the above Scheme 4, amines 21 and 22 synthesized in the Scheme 3, were condensed with 3-methoxy-4-methoxymethoxybenzyl isothiocyanate to produce compound 26 and 27. MOM(methylmethylether) group was hydrolyzed under acidic conditions, to give the thioureas 28 and 29. Amines 21 and 22 were condensed with 3-methoxy-4-methoxymethoxybenzyl isocyanate to synthesize ureas 32 and 33. Also, Amines 21 and 22 were condensed with ester to synthesize amides 34 and 35. And condensation of amines 21 and 22 with ester, followed by hydrogenation, produced the corresponding amides 38 and 39.

SCHEME 5

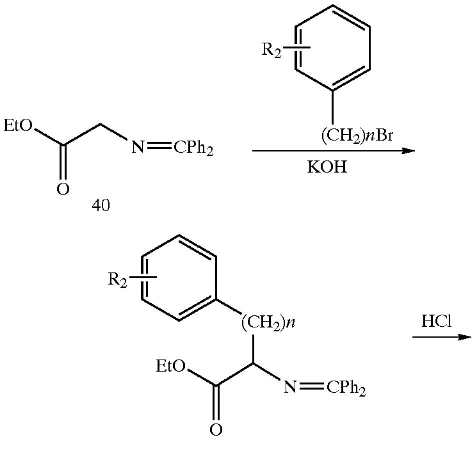

40

41 n = 1 $R_2$ = 3,4-($CH_3$)
42 n = 1 $R_2$ = 4-t-Bu
43 n = 2 $R_2$ = 3,4-$(CH_3)_2$

-continued

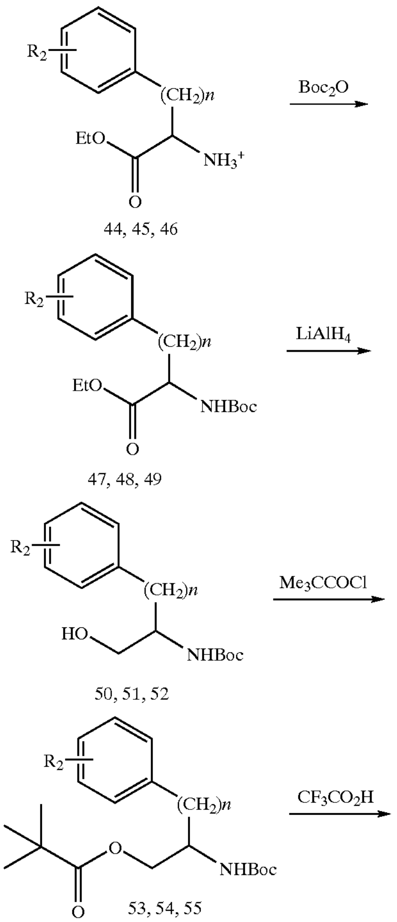

44, 45, 46

47, 48, 49

50, 51, 52

53, 54, 55

-continued

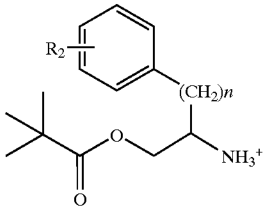

56, 57, 58

As depicted in the above Scheme 5, amine salts 44~46 which eliminated N-protection group were synthesized by using N-(diphenylmethylene)glycine 40 as a starting material according to a general method, and then the amine salts 40~42 were reacted with butoxycarbonyl group to produce compounds 47~49. Acylation of compounds 47~49 with pivaloylating agents, e.g., pivaloyl chloride under basic conditions, produced the corresponding acyl compounds 53~55. Elimination of the N-protection group produced the corresponding amines 56~58.

SCHEME 6

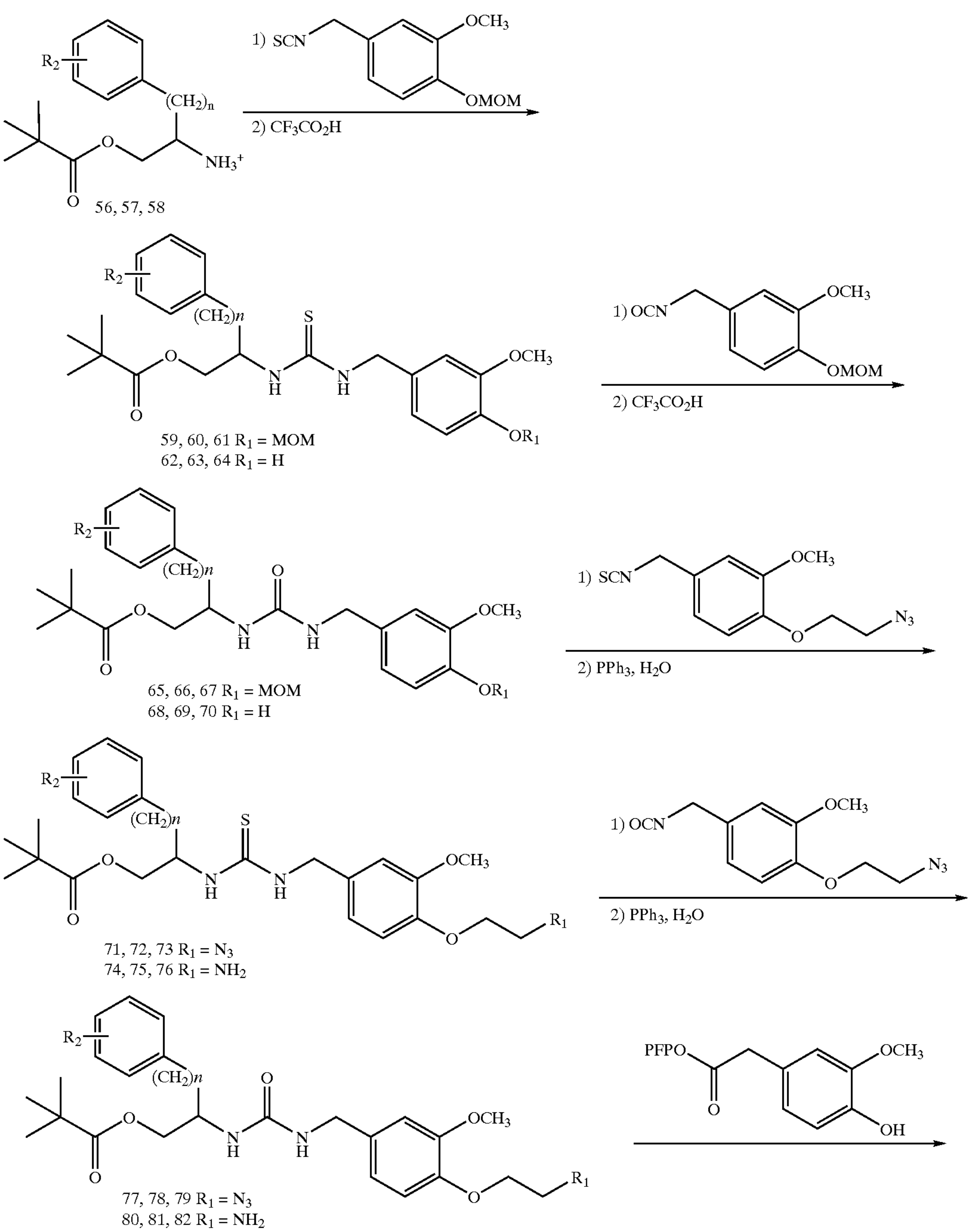

56, 57, 58

59, 60, 61 $R_1$ = MOM
62, 63, 64 $R_1$ = H 65, 66, 67 $R_1$ = MOM
68, 69, 70 $R_1$ = H 71, 72, 73 $R_1$ = $N_3$
74, 75, 76 $R_1$ = $NH_2$ 77, 78, 79 $R_1$ = $N_3$
80, 81, 82 $R_1$ = $NH_2$

-continued

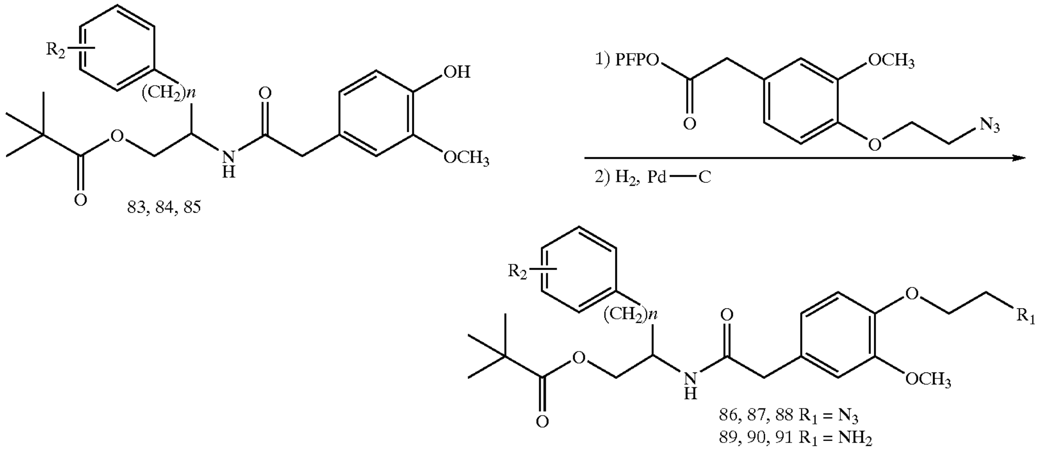

83, 84, 85

86, 87, 88 $R_1 = N_3$
89, 90, 91 $R_1 = NH_2$

As depicted in the above Scheme 6, amines 56~58 synthesized in the Scheme 5, were condensed with 3-methoxy-4-methoxymethoxybenzyl isothiocyanate to synthesize compounds 59~61 and hydrolyzed under trifluoro acetic acid to give compounds 62~64. And amines 56~58 were condensed with 3-methoxy-4-methoxymethoxybenzyl isothiocyanate to synthesize ureas 68~70. Also, amines 56~58 were condensed with 4-azidoethoxy-3-methoxy benzyl isothiocyanate to give compounds 71~73. Azido group of compounds 71~73 was reduced by $PPh_3$ to produce compounds 74~76. Also, amines 56~58 were condensed with 4-azidoethoxy-3-methoxy benzyl isothiocyanate to synthesize ureas 80~82. And amines 56~58 was condensed with homovanillic pentafluorophenol ester to produce compounds 83~85. Also, amines 56~58 were condensed with (4-azidoethyl)homovanillic pentafluorophenol ester to give compounds 86~88. Azido group of compounds 86~88 was reduced to amines, which in situ was condensed with homovanillic pentafluoro ester to produce compounds 89~91.

SCHEME 7

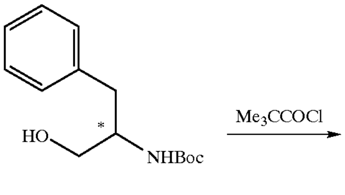

92 (R)
93 (S)

-continued

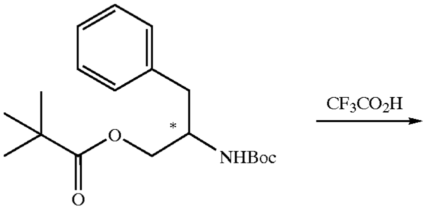

94 (R)
95 (S)

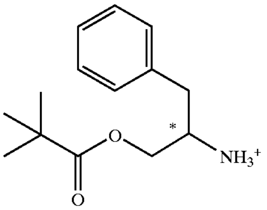

96 (R)
97 (S)

As depicted in the above Scheme 7, two chiral analogues of 96 and 97 were synthesized from N-Boc D-phenyl alaniol (R) 92 or N-Boc L-phenyl alaniol (S) 93 as a starting material. Acylation of compounds 92~93 with pivaloylating agents, e.g., pivaloyl chloride, produced the corresponding acyl compounds 94~95 with N-protection group. Elimination of the N-protection group, produced the racemic amines 96~97.

SCHEME 8

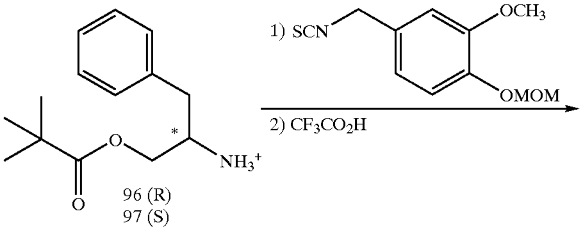

96 (R)
97 (S)

-continued

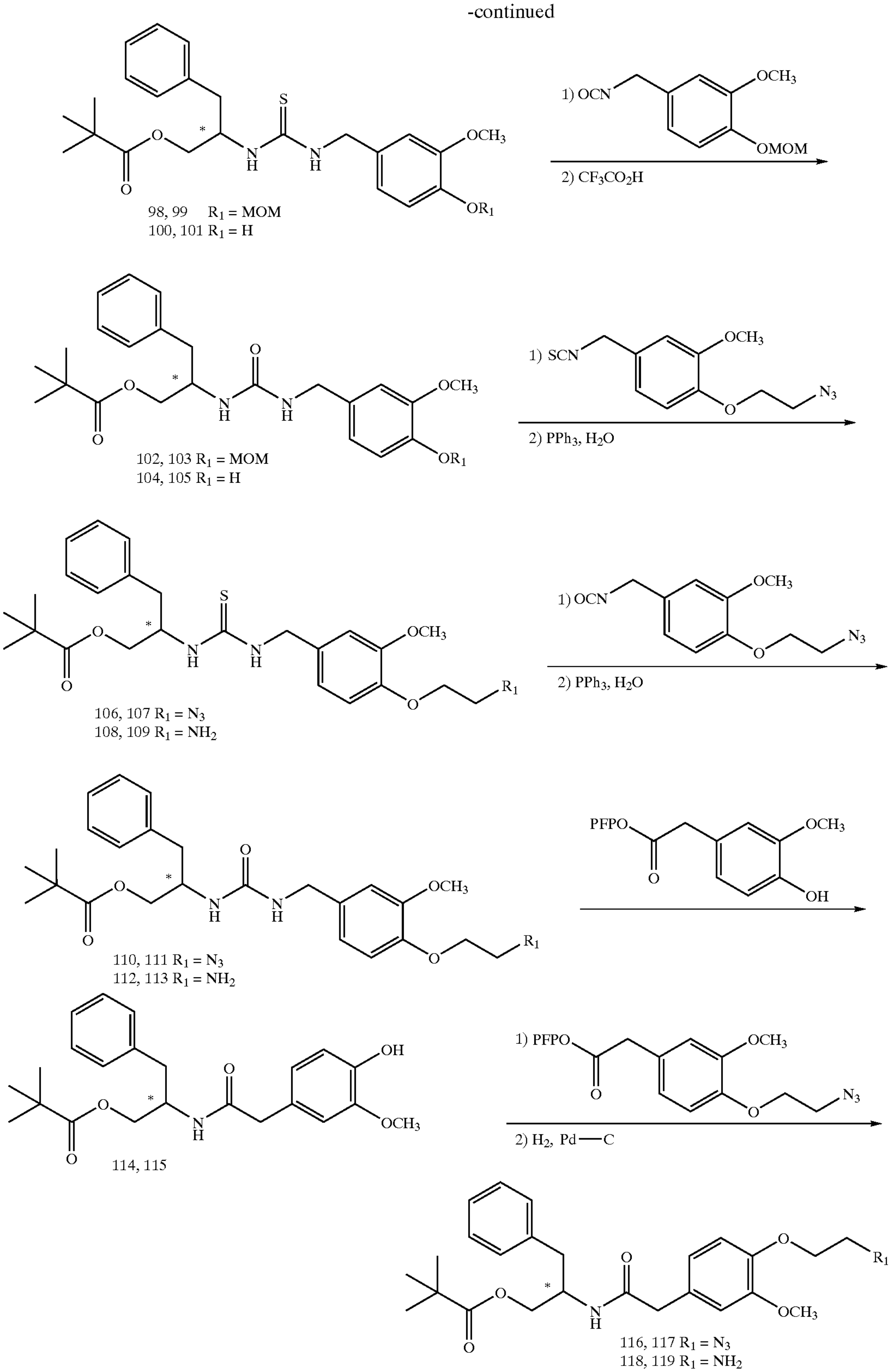

98, 99 $R_1$ = MOM
100, 101 $R_1$ = H 102, 103 $R_1$ = MOM
104, 105 $R_1$ = H 106, 107 $R_1$ = $N_3$
108, 109 $R_1$ = $NH_2$ 110, 111 $R_1$ = $N_3$
112, 113 $R_1$ = $NH_2$ 114, 115

116, 117 $R_1$ = $N_3$
118, 119 $R_1$ = $NH_2$

As depicted in the above Scheme 8, amines 96~97 synthesized in the Scheme 7, were condensed with 3-methoxy-4-methoxymethoxybenzyl isothiocyanate to produce compounds 98~99 which $R_1$ is substituted by MOM group and hydrolyzed under trifluoro acetic acid to give compounds 100~101. And amines 96~97 were condensed with 3-methoxy-4-methoxymethoxybenzyl isothiocyanate to synthesize ureas 104~105. Also, amines 96~97 were condensed with 4-azidoethoxy-3-methoxy benzyl isothiocyanate to give compounds 106~107 which $R_1$ is azido group. Azido group of compounds 106~107 was reduced by $PPh_3$ to produce compounds 108~109. Also, amines 96~97 were condensed with 4-azidoethoxy-3-methoxy benzyl isothiocyanate to synthesize ureas 112~113. And amines 96~97 was condensed with homovanillic pentafluorophenol ester to produce compounds 114~115. Also, amines 96~97 were condensed with (4-azidoethyl)homovanillic pentafluorophenol ester to give compounds 116~117. Aziodo group of compounds 116~117 was reduced to amines, which in situ was condensed with homovanillic pentafluoro ester to produce compounds 118~119.

SCHEME 9

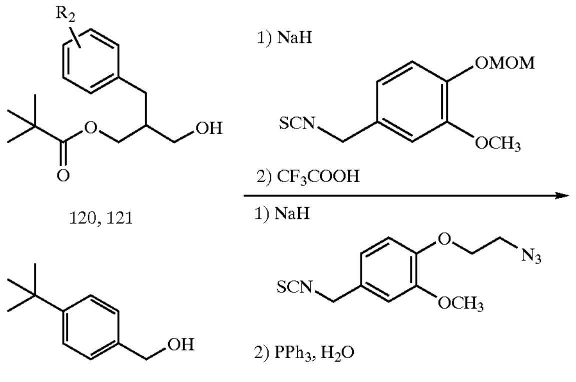

120, 121

122

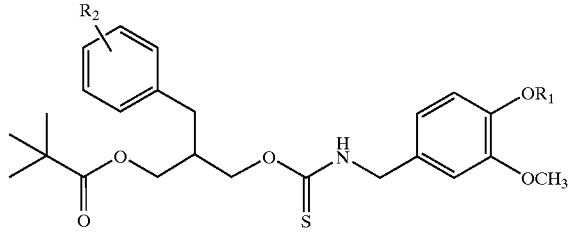

123, 124 $R_1$ = MOM
125, 126 $R_1$ = H
127, 128 $R_1$ = $CH_2CH_2N_3$
129, 130 $R_1$ = $CH_2CH_2NH_2$

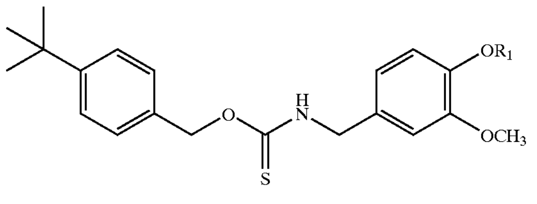

131 $R_1$ = MOM
132 $R_1$ = H
133 $R_1$ = $CH_2CH_2N_3$
134 $R_1$ = $CH_2CH_2NH_2$

As depicted in the above Scheme 9, compounds 120~122 were condensed with 3-methoxy-4-methoxymethoxybenzyl isothiocyanate under basic conditions, and hydrolyzed under acidic conditions, to produce thiocarbamates 125, 126 and 132. Also, compounds 120~122 were condensed with 3-methoxy-4-azidoethoxybenzyl isothiocyanate under basic conditions, and reduced by $PPh_3$ to produce thiocarbamate 129, 130 and 134.

SCHEME 10

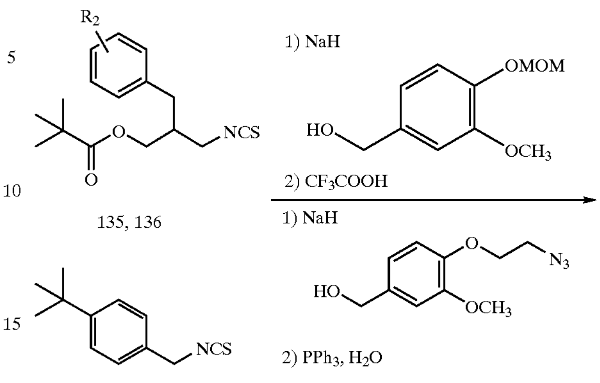

135, 136

137

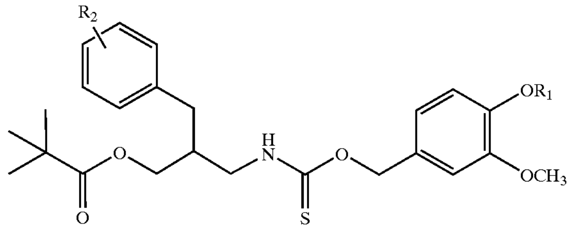

138, 139 $R_1$ = MOM
140, 141 $R_1$ = H
142, 143 $R_1$ = $CH_2CH_2N_3$
144, 145 $R_1$ = $CH_2CH_2NH_2$

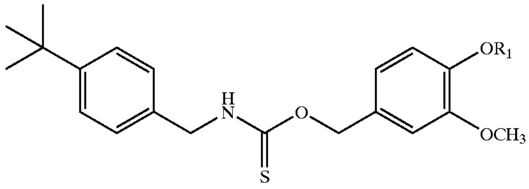

146 $R_1$ = MOM
147 $R_1$ = H
148 $R_1$ = $CH_2CH_2N_3$
149 $R_1$ = $CH_2CH_2NH_2$

As depicted in the above Scheme 10, isothiocyanate group of compound 135~137 was condensed with 3-methoxy-4-methoxymethoxybenzyl alcohol under basic conditions, and hydrolyzed under acidic conditions, to produce thiocarbamates 140, 141 and 147. Also, isothiocyanate group of compound 135~137 was condensed with 3-methoxy-4-azidoethoxybenzyl alcohol under basic conditions and reduced by $PPh_3$ to produce thiocarbamates 144, 145 and 149.

The present invention also provides a pharmaceutical composition comprising a compound of formula (I), (II) or (III) or a pharmaceutically acceptable salt thereof as an active ingredient.

The compound of formula (I), (II) or (III) according to the present invention can be provided as a pharmaceutical composition containing pharmaceutically acceptable carriers, adjuvants or diluents. For example, the compounds of the present invention can be dissolved in oils, propylene glycol or other solvents which are commonly used to produce an injection. Suitable examples of the carriers include physiological saline, polyethylene glycol, ethanol, vegetable oils, isopropyl myristate, etc., but are not limited to them. For topical administration, the compounds of the present invention can be formulated in the form of ointments and creams.

The pharmaceutical compositions comprising the compound of the present invention may be applied for the following occasions:

- to relieve pain caused by posttherpetic neuralgia, diabetic neuropathy, postmastectomy pain syndrome, stump pain, reflex sympathetic dystrophy, trigeminal neuralgia, oral neuropathic pain, osteoarthritis, rheumatoid arthritis, fibromyalgia, Guillain-Barre syndrome, meralgia paraesthetica, burning mouth syndrom.
- to ameliorate pain such as intractable pain due to bilateral peripheral neuropathy
- to relieve itch due to psoriasis, hemodyalisis, aquagenic pruritus, vulvar vestibulitis, notalgia paraesthetica, brachioradial prutitus, Lichen simplex chronicus
- to treat cluster headache, vasomotor rhinitis or perenial allergic rhinitis in the form of intranasal drop
- to treat bladder hypersensitivity or spinal detrusor hyperreflexia in the form of intravesical solution.

The compound of the present invention has potent analgesic and antiinflammatory activity, and the pharmaceutical composition of the present invention thus may be employed to alleviate or relieve acute, chronic or inflammatory pains, suppress inflammation, or treat urgent urinary incontinence.

The present invention also provides a method of alleviating or relieving acute, chronic, inflammatory or neuropathic pains of suppressing inflammation or treating urge incontinence which comprises administering compound selected from the group consisting of compounds of formula (I), (II) or (III) or pharmaceutical acceptable salts thereof as agonists of vanilloid receptors.

In accordance with another aspect of the present invention, there is also provided a method for alleviating and/or treating pain, acute pain, chronic pain, neuropathic pain, post-operative pain, migraine, arthralgia, neuropathies, nerve injury, diabetic neuropathy, neurodegeneration, neurotic skin disorder, stroke, urinary bladder, hypersensitiveness, irritable bowel syndrome, a respiratory disorder such as asthma or chronic obstructive pulmonary disease, irritation of skin, eye or mucous membrane, fervescene, stomach-duodenal ulcer, inflammatory bowel disease, inflammatory disease or urgent urinary incontinence, comprising administrating with the compound (I), (II) or (III) in need of such prevention or treatment a therapeutically effective amount of the salt or a pharmaceutically acceptable hydrate thereof.

Hereinafter, the following formulation methods and excipients are merely exemplary and in no way limit the invention.

The compounds of the present invention in pharmaceutical dosage forms may be used in the form of their pharmaceutically acceptable salts, and also may be used alone or in appropriate association, as well as in combination with other pharmaceutically active compounds.

The compounds of the present invention may be formulated into preparations for injections by dissolving, suspending, or emulsifying them in aqueous solvents such as normal saline, 5% Dextrose, or non-aqueous solvent such as vegetable oil, synthetic aliphatic acid glycerides, esters of higher aliphatic acids or propylene glycol. The formulation may include conventional additives such as solubilizers, isotonic agents, suspending agents, emulsifying agents, stabilizers and preservatives.

The desirable dose of the inventive compounds varies depending on the condition and the weight of the subject, severity, drug form, route and period of administration, and may be chosen by those skilled in the art. However, in order to obtain desirable effects, it is generally recommended to administer at the amount ranging 0.0001–100 mg/kg, preferably 0.001–100 mg/kg by weight/day of the inventive compounds of the present invention. The dose may be administered in single or divided into several times per day. In terms of composition, the compounds should be present between 0.0001 to 10% by weight, preferably 0.0001 to 1% by weight based on the total weight of the composition.

The pharmaceutical composition of present invention can be administered to a subject animal such as mammals (rat, mouse, domestic animals or human) via various routes. All modes of administration are contemplated, for example, administration can be made orally, rectally or by intravenous, intramuscular, subcutaneous, intrathecal, epidural or intracerebroventricular injection.

The present invention is more specifically explained by the following examples. However, it should be understood that the present invention is not limited to these examples in any manner.

EXAMPLES

Example 1

Preparation of 2-(3,4-dimethylphenyl)acetonitrile (2)

A mixture solution of 3,4-dimethylbenzyl chloride 10 g (64.7 mmol) in dimethyl formamide (15 ml) was treated with sodium cyanide (15.85 g, 323.8 mmol) for 16 hrs at 100° C. The mixture was diluted with $H_2O$ and extracted with $CH_2Cl_2$ several times. The combined organic layers were washed with $H_2O$, dried over $MgSO_4$, and concentrated in vacuo. The residue was purified by flash column chromatography on silica gel with EtOAc/hexanes (1:10) as an eluant to give compound 2.

100% yield, colorless oil. $^1$H-NMR ($CDCl_3$) δ: 6.95–7.25 (m, 5 H), 3.60 (s, 2 H, $CH_2CN$), 2.25 (d, 3 H, J=12.9 Hz, $CH_3$), 2.20 (d, 3 H, J=12.9 Hz, $CH_3$).

Example 2

Preparation of methyl-2-(3,4-dimethylphenyl) acetate (4)

A mixture solution of 2-(3,4-dimethylphenyl)acetonitrile (2) (9.395 g, 64.7 mmol) in methanol was refluxed with $H_2SO_4$ 3.5 ml (64.7 mmol) for 3 days. The mixture was cooled, diluted with $H_2O$ and concentrated in vacuo under sodium bicarbonate. The residue was separated $H_2O$ and $CH_2Cl_2$ and the $H_2O$ layer was extracted with $CH_2Cl_2$ several times. The combined organic layers were washed with $H_2O$, dried over $MgSO_4$, and concentrated in vacuo. The residue was purified by flash column chromatography on silica gel with EtOAc/hexanes (1:10) as an eluant to give compound 4.

98% yield, yellow oil. $^1$H-NMR ($CDCl_3$) δ: 6.95–7.1 (m, 5 H), 3.66 (s, 3 H, $CO_2CH_3$), 3.54 (s, 2 H, $CH_2CO_2$), 2.25 (d, 3 H, J=13.4 Hz, $CH_3$), 2.20 (d, 3 H, J=9.8 Hz, $CH_3$).

Example 3

Preparation of 2-(3,4-dimethylphenyl)1-ethanol (6)

A cooled solution of lithium aluminium hydride (4.8 g, 126.6 mmol) in diethyl ether at 10° C. was treated dropwise with a solution of methyl-2-(3,4-dimethylphenyl)acetate(4). After stirring for 3 hrs at room temperature, the reaction mixture was stirred for 30 min at room temperature, cooled in ice-bath and stirred for 1 hr at room temperature by the dropwise addition of $H_2O$ 5 ml, NaOH 10 ml and $H_2O$ 15 ml. The mixture was filtered and washed with EtOAc and the filtrate was concentrated in vacuo. The residue was purified by flash column chromatography on silica gel with EtOAc/hexanes (1:3) as an eluant to give compound 6.

60% yield, colorless oil. $^1H$-NMR ($CDCl_3$) δ: 6.95–7.1 (m, 5 H), 3.85 (m, 2 H, $CH_2OH$), 2.81 (t, 2 H, J=6.6 Hz, $CH_2Ar$), 2.25 (m, 6 H, 2×$CH_3$).

Example 4

Preparation of 4-(2-bromoethyl)-1,2-dimethylbenzen (8)

A mixture solution of 2-(3,4-dimethylphenyl)1-ethanol(6) (3.285 g, 21.9 mmol) in tetrahydrofuran (20 ml) was treated with triphenyl phosphine (6.883 g, 26.2 mmol) at 0° C. and stirred for 3 hrs at room temperature by addition of carbon tetrabromide (8.703 g, 26.2 mmol). The mixture was diluted with ether and filtered and the filtrate was concentrated in vacuo. The residue was purified by flash column chromatography on silica gel with hexanes as an eluant to give compound 8.

91% yield, colorless oil. $^1H$-NMR ($CDCl_3$) δ: 6.95–7.1 (m, 5 H), 3.54 (t, 2 H, J=7.3 Hz, $CH_2Br$), 3.10 (t, 2 H, J=7.8 Hz, $CH_2Ar$), 2.25 (m, 6 H, 2×$CH_3$).

Example 5

Preparation of 2-(4-t-butylphenyl)1-ethanol (11)

A mixture solution of butyl styrene (10) (4.81 g, 30 mmol) in tetrahydrofuran was treated with sodium borohydride (0.34 g, 9 mmol), and stirred for 2 hrs at room temperature by addition of boron trifluoride-diethyl (1.84 ml, 15 mmol). The reaction mixture was quenched by addition of $H_2O$ (10 ml) cautiously, basified with NaOH (15 ml), treated with 30% hydrogen peroxide. The reaction mixture was diluted with ice-water and extracted with ether several times. The combined organic layers were washed with $H_2O$, dried over $MgSO_4$, and concentrated in vacuo. The residue was purified by flash column chromatography on silica gel with EtOAc/hexanes (1:5) as an eluant to give compound 11.

78% yield, colorless oil. $^1H$-NMR ($CDCl_3$) δ: 7.34 (d, 2 H, J=8.0 Hz), 7.16 (d, 2 H, J=8.0 Hz), 3.86 (dd, 2 H, J=6.4, 12.7 Hz, $CH_2OH$), 2.85 (t, 2 H, J=6.6 Hz, $CH_2Ar$), 1.31 (s, 9 H, $C(CH_3)_3$).

Example 6

Preparation of 4-(2-bromoethyl)4-t-butyl-benzene (12)

A mixture solution of 2-(4-t-butylphenyl)1-ethanol(11) (3.285 g, 21.9 mmol) in tetrahydrofuran (20 ml) was treated with triphenyl phosphine (6.883 g, 26.2 mmol) at 0° C. and stirred for 3 hrs at room temperature by addition of carbon tetrabromide (8.703 g, 26.2 mmol). The mixture was dilted with ether and filtered and the filtrate was concentrated in vacuo. The residue was purified by flash column chromatography on silica gel with hexanes as an eluant to give compound 12.

90% yield, colorless oil. $^1H$-NMR ($CDCl_3$) δ: 7.35 (d, 2 H, J=8.3 Hz), 7.14 (d, 2 H, J=8.3 Hz), 3.55 (t, 2 H, J=7.3 Hz, $CH_2Br$), 3.10 (t, 2 H, J=7.8 Hz, $CH_2Ar$), 1.31 (s, 9 H, $C(CH_3)_3$).

Example 7

Preparation of Diethyl 2-(3,4-dimethylphenethyl) malonate (13)

A cooled solution of diethylmalonate (6.4 g, 40 mmol) in DMF (20 ml) at 0° C. was treated with sodium hydride (60%, 1.92 g, 48 mmol) portionwise and stirred for 40 min at room temperature. The reaction mixture was added with 3,4-dimethylbenzyl chloride (8) (48 mmol) and stirred for 16 hrs at room temperature. The mixture was diluted with $H_2O$ and extracted with EtOAc several times. The combined organic layers were washed with $H_2O$ and brine, dried over $MgSO_4$ and concentrated in vacuo. The residue was purified by flash column chromatography on silica gel with EtOAc/hexanes (1:10) as an eluant to give compound 13.

76% yield, colorless oil. $^1H$-NMR ($CDCl_3$) δ: 6.9–7.1 (m, 3 H), 4.20 (q, 4 H, J=7.1 Hz, 2×$CO_2CH_2CH_3$), 3.34 (t, 1 H, J=7.6 Hz, CH), 2.59 (t, 2 H, J=6.5 Hz, $CH_2Ar$), 2.1–2.3 (m, 6 H, 2×$CH_3$ and $CH_2CH_2Ar$), 1.27 (t, 6 H, J=7.1 Hz, 2×$CO_2CH_2CH_3$).

Example 8

Preparation of Diethyl 2-(4-t-butylphenethyl) malonate (14)

The compound 14 was prepared by the same procedure with that described in above Example 7.

78% yield, colorless oil. $^1H$-NMR ($CDCl_3$) δ: 7.31 (d, 2 H, J=8.3 Hz), 7.12 (d, 2 H, J=8.3 Hz), 4.19 (q, 4 H, J=7.1 Hz, 2×$CO_2CH_2CH_3$), 3.35 (t, 1 H, J=7.6 Hz, CH), 2.63 (t, 2 H, J=7.3 Hz, $CH_2Ar$), 2.21 (m, 2 H, $CH_2CH_2Ar$), 1.31 (s, 9 H, $C(CH_3)_3$), 1.27 (t, 6 H, J=7.1 Hz, 2×$CO_2CH_2CH_3$).

Example 9

Preparation of 2-(3,4-dimethylphenethyl)-1,3-propanediol (15)

A cooled solution of lithium aluminium hydride (3.64 g, 96 mmol) in diethyl ether (80 ml) at 0° C. was treated dropwise with a solution of diester compound (13) (24 mmol) in diethyl ether (20 ml). After stirring for 3 hrs at room temperature, the reaction mixture was cooled over an ice-bath and treated successively by the dropwise addition of $H_2O$ (3.5 ml), 15% NaOH solution (7 ml), and $H_2O$ (10.5 ml). The mixture was filtered by washing with EtOAc and the filtrate was concentrated in vacuo. The residue was purified by flash column chromatography on silica gel with EtOAc/hexanes (3:1) as an eluant to give compound 15.

74% yield, white solid. $^1H$-NMR ($CDCl_3$) δ: 6.9–7.1 (m, 3 H), 3.85 (m, 2 H, $CH_2OH$), 3.71 (m, 2 H, $CH_2OH$), 2.60 (t, 2 H, J=7.3 Hz, $CH_2Ar$), 2.23 (dd, 6 H, 2×$CH_3$), 1.82 (m, 1 H, CH), 1.5–1.65 (m, 2 H, $CH_2CH_2Ar$).

Example 10

Preparation of 2-(4-tert-butylphenethyl)-1,3-propanediol (16)

The compound 16 was prepared by the same procedure with that described in above Example 9.

86% yield, white solid $^1H$-NMR ($CDCl_3$) δ: 7.30 (d, 2 H, J=8.3 Hz), 7.12 (d, 2 H, J=8.3 Hz), 3.86 (m, 2 H, $CH_2OH$), 3.72 (m, 2 H, $CH_2OH$), 2.64 (t, 2 H, J=7.3 Hz, $CH_2Ar$), 1.82 (m, 1 H, CH), 1.5–1.65 (m, 2 H, $CH_2CH_2Ar$), 1.31 (s, 9 H, $C(CH_3)_3$).

Example 11

Preparation of 4-(3,4-Dimethylphenyl)-2-(hydroxymethyl)butyl pivalate (17)

A cooled solution of diol compound (15) (15 mmol), pyridine (16.5 mmol, 1.33 ml) in $CH_2Cl_2$ (50 ml) was treated with pivaloyl chloride (16.5 mmol, 2.02 ml) at 0° C. After being stirred for 30 min at 0° C., the reaction mixture was quenched with ice and extracted with EtOAc several times. The combined organic layers were washed with $H_2O$ and brine, dried over $MgSO_4$ and concentrated in vacuo. The residue was purified by column chromatography on silica gel with EtOAc/hexanes (1:4) as an eluant to give compound 17.

84% yield, colorless oil. $^1$H-NMR ($CDCl_3$) δ: 6.9–7.1 (m, 3 H), 4.26 (dd of AB, 1 H, J=4.4, 11.4 Hz, $CH_2OCO$), 4.14 (dd of AB, 1 H, J=6.1, 11.4 Hz, $CH_2OCO$), 3.56 (m, 2 H, $CH_2OH$), 2.62 (t, 2 H, J=7.8 Hz, $CH_2Ar$), 2.23 (dd, 6 H, 2×$CH_3$), 2.03 (t, 1 H, OH), 1.85 (m, 1 H, CH), 1.55–1.75 (m, 2 H, $CH_2CH_2Ar$), 1.21 (s, 9 H, $C(CH_3)_3$).

Example 12

Preparation of 4-(4-tert-Butylphenyl)-2-(hydroxymethyl)butyl pivalate (18)

The compound 18 was prepared by the same procedure with that described in above Example 11.

80% yield, colorless oil. $^1$H-NMR ($CDCl_3$) δ: 7.33 (d, 2 H, J=8.2 Hz), 7.14 (d, 2 H, J=8.2 Hz), 4.29 (dd of AB, 1 H, J=4.3, 11.4 Hz, $CH_2OCO$), 4.17 (dd of AB, 1 H, J=6.0, 11.4 Hz, $CH_2OCO$), 3.63 (m, 1 H, $CH_2OH$), 3.55 (m, 1 H, $CH_2OH$), 2.68 (t, 2 H, J=7.8 Hz, $CH_2Ar$), 2.08 (bs, 1 H, OH), 1.90 (m, 1 H, CH), 1.6–1.75 (m, 2 H, $CH_2CH_2Ar$), 1.33 (s, 9 H, $C(CH_3)_3$), 1.24 (s, 9 H, $COC(CH_3)_3$).

Example 13

Preparation of 2-(Azidomethyl)-4-(3,4-dimethylphenyl)butyl pivalate (19)

A mixture of alcohol (17) (10 mmol), triphenylphospine (20 mmol, 5.25 g), diethyl azodicarboxylate (20 mmol, 3.15 ml) in THF (70 ml) was treated with diphenylphosphorylazide (20 mmol, 4.32 ml) and stirred at room temperature for 18 h. The solvent was removed in vacuo and the residue was purified by column chromatography on silica gel with EtOAc/hexanes (1:10) as an eluant to give compound 19.

82% yield, colorless oil. $^1$H-NMR ($CDCl_3$) δ: 6.9–7.1 (m, 3 H), 4.10 (m, 2 H, $CH_2OCO$), 3.38 (d, 2 H, J=5.8 Hz, $CH_2N_3$), 2.60 (t, 2 H, J=7.4 Hz, $CH_2Ar$), 2.23 (dd, 6 H, 2×$CH_3$), 1.95 (m, 1 H, CH), 1.6–1.7 (m, 2 H, $CH_2CH_2Ar$), 1.21 (s, 9 H, $C(CH_3)_3$).

Example 14

Preparation of 2-(Azidomethyl)-4-(4-tert-butylphenyl)butyl pivalate (20)

The compound 20 was prepared by the same procedure with that described in above Example 13.

84% yield, colorless oil $^1$H-NMR ($CDCl_3$) δ: 7.32 (d, 2 H, J=8.5 Hz), 7.11 (d, 2 H, J=8.5 Hz), 4.12 (dd of AB, 1 H, J=4.9, 11.2 Hz, $CH_2OCO$), 4.08 (dd of AB, 1 H, J=4.4, 11.4 Hz, $CH_2OCO$), 3.38 (d, 2 H, J=5.8 Hz, $CH_2N_3$), 2.64 (t, 2 H, J=7.3 Hz, $CH_2Ar$), 1.95 (m, 1 H, CH), 1.65–1.75 (m, 2 H, $CH_2CH_2Ar$), 1.31 (s, 9 H, $C(CH_3)_3$), 1.21 (s, 9 H, $COC(CH_3)_3$).

Example 15

Preparation of 2-(Aminomethyl)-4-(4-tert-butylphenyl)butyl pivalate (21)

A suspension of compound 20 (0.5 mmol) and Lindler's catalyst (50 mg) in EtOH (5 ml) was hydrogenated under a hydrogen balloon for 2 hrs. The reaction mixture was filtered and the filtrate was concentrated in vacuo to give amine in a quantitative yield, which was used for the next step without further purification.

Procedure A: General Method for the Synthesis of Thiourea and Amide

A solution of amine (1 mmol) (1.2 mmol of $NEt_3$ was added in case of amine salt) was treated with isothiocyanate (1 mmol) or pentafluorophenyl ester (1 mmol) in $CH_2Cl_2$ (10 ml) was stirred overnight at room temperature and concentrated in vacuo. The residue was purified by flash column chromatography on silica gel with EtOAc/hexanes (1:1) as an eluant.

Procedure B: General Method for Deprotection of Methoxymethyl Group

A cooled solution of the compound (1 mmol) in $CH_2Cl_2$ (4 ml) at 0° C. was treated with trifluoroacetic acid (2 ml) and stirred for 1 hr at room temperature. The mixture was quenched with solid $NaHCO_3$ and filtered and the filtrate was concentrated in vacuo. The residue was diluted with EtOAc, washed with $NaHCO_3$, $H_2O$ and brine, and concentrated in vacuo. The residue was purified by flash column chromatography on silica gel with EtOAc/hexanes (1:1) as an eluant.

Procedure C: General Method for Azide Reduction by Triphenylphosphine

A mixture of azide (1 mmol), triphenylphosphine (1.1 mmol) and $H_2O$ (5 mmol) in THF (10 ml) was stirred overnight at room temperature and concentrated in vacuo. The residue was purified by flash column chromatography on silica gel with $CH_2Cl_2$/MeOH (8:1) as an eluant.

Procedure D: General Method for Azide Reduction by Catalytic Hydrogenation

A mixture of azide (1 mmol) and 5% palladium on carbon (10% w/w) in MeOH (10 ml) was hydrogenated under a balloon of hydrogen for 1 hr. The reaction mixture was filtered and the filtrate was concentrated in vacuo. The residue was purified by flash column chromatography on silica gel with $CH_2Cl_2$/MeOH (10:1) as an eluant.

Procedure E: General Method for the Thiocarbamate

A cooled solution of alcohol (1 mmol) in DMF or THF (4 ml) at 0° C. was treated with sodium hydride (60%, 40 mg, 1 mmol) and stirred for 20 min at 0° C. To the mixture isothiocyanate (1 mmol) was added and the mixture was stirred for 1–2 hrs at room temperature. After aqueous work-up, the residue was purified by flash column chromatography to give the corresponding thiocarbamate.

Example 16

N-[4-(3,4-Dimethylphenyl)-2-(pivaloyloxymethyl)butyl]-N'-[4-(methoxymethoxy)-3-methoxybenzyl]thiourea (26)

The compound 26 was prepared with compound 19 by the same procedure with that described in above Procedure A.

85% yield, white solid. $^1$H-NMR ($CDCl_3$) δ: 6.8–7.15 (m, 6 H), 6.32 (t, 1 H, NH), 6.01 (bs, 1 H, NH), 5.21 (s, 2 H, $OCH_2O$), 4.50 (d, 2 H, J=5.2 Hz, $CSNHCH_2Ar$), 4.18 (dd, 1 H, J=3.7, 11.5 Hz, $CH_2OCO$), 3.95 (dd, 1 H, J=5.1, 11.5 Hz, $CH_2OCO$), 3.86 (s, 3 H, $OCH_3$), 3.76 (m, 1 H, $CHCH_2NHCS$), 3.50 (s, 3 H, $OCH_3$), 3.23 (m, 1 H, $CHCH_2NHCS$), 2.65 (t, 2 H, J=8.3 Hz, $CH_2CH_2Ar$), 2.15–2.3 (m, 7 H, 2×$CH_3$), 1.94 (m, 1 H, CH), 1.60 (m, 2 H, $CH_2CH_2Ar$), 1.20 (s, 9 H, $COC(CH_3)_3$).

Example 17

N-[4-tert-Butylphenyl-2-(pivaloyloxymethyl)butyl]-N'-[4-(methoxymethoxy)-3-methoxy-benzyl]thiourea (27)

The compound 27 was prepared with compound 20 by the same procedure with that described in above Procedure A.

89% yield, white solid. $^1H$-NMR ($CDCl_3$) δ: 7.30 (d, 2 H, J=8.3 Hz), 7.1–7.15 (m, 3 H), 6.8–6.9 (m, 2 H), 6.41 (bt, 1 H, NH), 6.35 (bs, 1 H, NH), 6.10 (bs, 1 H, NH), 5.21 (s, 2 H, $OCH_2O$), 4.51 (d, 2 H, J=4.1 Hz, $CSNHCH_2Ar$), 4.18 (dd, 1 H, J=3.7, 11.5 Hz, $CH_2OCO$), 3.95 (dd, 1 H, J=5.1, 11.5 Hz, $CH_2OCO$), 3.86 (s, 3 H, $OCH_3$), 3.75 (m, 1 H, $CHCH_2NHCS$), 3.50 (s, 3 H, $OCH_3$), 3.25 (m, 1 H, $CHCH_2NHCS$), 2.69 (t, 2 H, J=7.8 Hz, $CH_2CH_2Ar$), 2.03 (m, 1 H, CH), 1.60 (m, 2 H, $CH_2CH_2Ar$), 1.30 (s, 3 H, $C(CH_3)_3$), 1.19 (s, 9 H, $COC(CH_3)_3$).

Example 18

N-[4-(3,4-Dimethylphenyl)-2-(pivaloyloxymethyl) butyl]-N'-[4-hydroxy-3-methoxybenzyl] thiourea (28)

The compound 28 was prepared with compound 26 by the same procedure with that described in above Procedure B. 73% yield, yellow oil. $^1H$-NMR ($CDCl_3$) δ: 6.8–7.1 (m, 6 H), 6.29 (bt, 1 H, NH), 6.00 (bs, 1 H, NH), 5.60 (s, 1 H, OH), 4.48 (bs, 2 H, $CSNHCH_2Ar$), 4.20 (dd, 1 H, J=3.7, 11.5 Hz, $CH_2OCO$), 3.96 (dd, 1 H, J=5.1, 11.5 Hz, $CH_2OCO$), 3.87 (s, 3 H, $OCH_3$), 3.78 (bs, 1 H, $CHCH_2NHCS$), 3.25 (m, 1 H, $CHCH_2NHCS$), 2.65 (t, 2 H, J=8.3 Hz, $CH_2CH_2Ar$), 2.2–2.3 (m, 6 H, 2×$CH_3$), 2.00 (m, 1 H, CH), 1.58 (m, 2 H, $CH_2CH_2Ar$), 1.19 (s, 9 H, $COC(CH_3)_3$). MS m/z: 487 ($MH^+$)

Example 19

N-[4-tert-Butylphenyl-2-(pivaloyloxymethyl)butyl]-N'-[4-hydroxy-3-methoxybenzyl]thiourea (29)

The compound 29 was prepared with compound 27 by the same procedure with that described in above Procedure B.

78% yield, yellow oil. $^1H$-NMR ($CDCl_3$) δ: 7.33 (d, 2 H, J=8.2 Hz), 7.14 (d, 2 H, J=8.2 Hz), 6.8–6.9 (m, 3 H), 6.34 (bt, 1 H, NH), 6.10 (bs, 1 H, NH), 5.63 (s, 1 H, OH), 4.50 (bs, 2 H, $CSNHCH_2Ar$), 4.20 (dd, 1 H, J=3.7, 11.6 Hz, $CH_2OCO$), 3.97 (dd, 1 H, J=5.1, 11.6 Hz, $CH_2OCO$), 3.89 (s, 3 H, $OCH_3$), 3.79 (bs, 1 H, $CHCH_2NHCS$), 3.28 (m, 1 H, $CHCH_2NHCS$), 2.71 (t, 2 H, J=8.1 Hz, $CH_2CH_2Ar$), 2.04 (m, 1 H, CH), 1.62 (m, 2 H, $CH_2CH_2Ar$), 1.33 (s, 3 H, $C(CH_3)_3$), 1.21 (s, 9 H, $COC(CH_3)_3$). MS m/z: 515 ($MH^+$)

Example 20

N-[4-(3,4-dimethylphenyl)-2-(pivaloyloxymethyl) butyl]-N-[4-hydroxy-3-methoxybenzyl]urea (32)

The compound 32 was prepared by the same procedure with that described in above Procedure A and B.

$^1H$-NMR ($CDCl_3$) δ: 6.85–7.1 (m, 6 H), 6.25 (bt, 1 H, NH), 5.82 (bs, 1 H, NH), 5.58 (s, 1 H, OH), 4.18 (bs, 2 H, $CSNHCH_2Ar$), 4.14 (dd, 1 H, J=3.7, 11.5 Hz, $CH_2OCO$), 3.96 (dd, 1 H, J=5.1, 11.5 Hz, $CH_2OCO$), 3.85 (s, 3 H, $OCH_3$), 3.38 (bs, 1 H, $CHCH_2NHCS$), 3.18 (m, 1 H, $CHCH_2NHCS$), 2.62 (t, 2 H, J=8.3 Hz, $CH_2CH_2Ar$), 2.2–2.3 (m, 6 H, 2×$CH_3$), 1.94 (m, 1 H, CH), 1.54 (m, 2 H, $CH_2CH_2Ar$), 1.19 (s, 9 H, $COC(CH_3)_3$). MS m/z: 471 ($MH^+$)

Example 21

N-[4-t-butylphenyl-2-(pivaloyloxymethyl)butyl]-N-[4-hydroxy-3-methoxybenzyl]urea (33)

The compound 33 was prepared by the same procedure with that described in above Procedure A and B.

$^1H$-NMR($CDCl_3$) δ: 7.32(d, 2 H, J=8.2 Hz), 7.12 (d, 2 H, J=8.2 Hz), 6.8–6.9 (m, 3 H), 6.32 (bt, 1 H, NH), 6.08 (bs, 1 H, NH), 5.60 (s, 1 H, OH), 4.20 (bs, 2 H, $CSNHCH_2Ar$), 4.16 (dd, 1 H, J=3.7, 11.6 Hz, $CH_2OCO$), 3.94 (dd, 1 H, J=5.1, 11.6 Hz, $CH_2OCO$), 3.84 (s, 3 H, $OCH_3$), 3.38 (bs, 1 H, $CHCH_2NHCS$), 3.16 (m, 1 H, $CHCH_2NHCS$), 2.66 (t, 2 H, J=8.1 Hz, $CH_2CH_2Ar$), 1.96 (m, 1 H, CH), 1.60 (m, 2 H, $CH_2CH_2Ar$), 1.32 (s, 3 H, $C(CH_3)_3$), 1.21 (s, 9 H, $COC(CH_3)_3$). MS m/z: 499 ($MH^+$)

Example 22

N-[4-(3,4-Dimethylphenyl)-2-(pivaloyloxymethyl) butyl]-2-[4-hydroxy-3-methoxyphenyl] acetamide (34)

The compound 34 was prepared with compound 19 by the same procedure with that described in above Procedure A.

59% yield, pink oil. $^1H$-NMR ($CDCl_3$) δ: 6.7–7.05 (m, 6 H), 5.76 (bt, 1 H, NH), 5.63 (s, 1 H, OH), 4.02 (dd, 1 H, J=4.4, 11.5 Hz, $CH_2OCO$), 3.95 (dd, 1 H, J=5.4, 11.5 Hz, $CH_2OCO$), 3.86 (s, 3 H, $OCH_3$), 3.49 (s, 2 H, $OCCH_2Ar$), 3.29 (m, 1 H, $CH_2NH$), 3.13 (m, 1 H, $CH_2NH$), 2.58 (m, 2 H, $CH_2CH_2Ar$), 2.1–2.3 (m, 6 H, 2×$CH_3$), 1.84 (m, 1 H, CH), 1.54 (m, 2 H, $CH_2CH_2Ar$), 1.17 (s, 9 H, $COC(CH_3)_3$) MS m/z: 456 ($MH^+$)

Example 23

N-[4-(4-tert-Butylphenyl)-2-(pivaloyloxymethyl) butyl]-2-[4-hydroxy-3-methoxyphenyl] acetamide (35)

The compound 35 was prepared with compound 20 by the same procedure with that described in above Procedure A. 15% yield, yellow oil. $^1H$-NMR ($CDCl_3$) δ: 7.28 (d, 2 H, J=8.2 Hz), 7.06 (d, 2 H, J=8.3 Hz), 6.7–6.9 (m, 3 H), 5.75 (bt, 1 H, NH), 5.57 (s, 1 H, OH), 4.04 (dd, 1 H, J=4.6, 11.6 Hz, $CH_2OCO$), 3.94 (dd, 1 H, J=5.1, 11.6 Hz, $CH_2OCO$), 3.86 (s, 3 H, $OCH_3$), 3.49 (s, 2 H, $OCCH_2Ar$), 3.28 (m, 1 H, $CH_2NH$), 3.14 (m, 1 H, $CH_2NH$), 2.60 (dd, 2 H, J=6.3, 9.5 Hz $CH_2CH_2Ar$), 1.86 (m, 1 H, CH), 1.56 (m, 2 H, $CH_2CH_2Ar$), 1.30 (s, 3 H, $C(CH_3)_3$), 1.17 (s, 9 H, $COC(CH_3)_3$). IR (KBr): 3444, 2960, 1726, 1716, 1651, 1557, 1539, 1516 MS m/z: 484 ($MH^+$)

Example 24

N-[4-(3,4-Dimethylphenyl)-2-(pivaloyloxymethyl) butyl]-2-[4-(2-azidoethoxy)-3-methoxyphenyl]-acetamide (36)

The compound 36 was prepared by the same procedure with that described in above Procedure A.

98% yield, a colorless oil. $^1H$-NMR ($CDCl_3$) δ: 6.75–7.05 (m, 6 H), 5.78 (bt, 1 H, NH), 4.17 (t, 2 H, J=5.4 Hz, $OCH_2CH_2N_3$), 4.03 (dd, 1 H, J=4.1, 11.5 Hz, $CH_2OCO$), 3.95 (dd, 1 H, J=5.4, 11.5 Hz, $CH_2OCO$), 3.84 (s, 3 H, $OCH_3$), 3.62 (t, 2 H, J=6.7 Hz, $OCH_2CH_2N_3$), 3.50 (s, 2 H, $OCCH_2Ar$), 3.30 (m, 1 H, $CH_2NH$), 3.12 (m, 1 H, $CH_2NH$), 2.58 (m, 2 H, $CH_2CH_2Ar$), 2.22 (dd, 6 H, 2×$CH_3$), 1.84 (m, 1 H, CH), 1.55 (m, 2 H, $CH_2CH_2Ar$), 1.18 (s, 9 H, $COC(CH_3)_3$).

Example 25

N-[4-(4-tert-Butylphenyl)-2-(pivaloyloxymethyl) butyl]-2-[4-(2-azidoethoxy)-3-methoxyphenyl] acetamide (37)

The compound 37 was prepared by the same procedure with that described in above Procedure A.

97% yield, a colorless oil. $^1$H-NMR ($CDCl_3$) δ: 7.28 (d, 2 H, J=8.2 Hz), 7.06 (d, 2 H, J=8.3 Hz), 6.7–6.9 (m, 3 H), 5.78 (bt, 1 H, NH), 4.17 (t, 2 H, J=5.4 Hz, $OCH_2CH_2N_3$), 4.03 (dd, 1 H, J=4.1, 11.5 Hz, $CH_2OCO$), 3.94 (dd, 1 H, J=5.4, 11.5 Hz, $CH_2OCO$), 3.86 (s, 3 H, $OCH_3$), 3.62 (t, 2 H, J=5.4 Hz, $OCH_2CH_2N_3$), 3.48 (s, 2 H, $OCCH_2Ar$), 3.32 (m, 1 H, $CH_2NH$), 3.12 (m, 1 H, $CH_2NH$), 2.58 (m, 2 H, $CH_2CH_2Ar$), 1.84 (m, 1 H, CH), 1.55 (m, 2 H, $CH_2CH_2Ar$), 1.30 (s, 3 H, $C(CH_3)_3$), 1.18 (s, 9 H, $COC(CH_3)_3$).

Example 26

N-[4-(3,4-Dimethylphenyl)-2-(pivaloyloxymethyl) butyl]-2-[4-(2-aminoethoxy)-3-methoxyphenyl] acetamide (38)

The compound 38 was prepared by the same procedure with that described in above Procedure D.

92% yield, a colorless oil. $^1$H-NMR ($CDCl_3$) δ: 6.75–7.05 (m, 6 H), 5.88 (bt, 1 H, J=6.0 Hz, NH), 4.07 (t, 2 H, J=4.9 Hz, $OCH_2CH_2NH_2$), 4.03 (dd, 1 H, J=4.4, 11.5 Hz, $CH_2OCO$), 3.96 (dd, 1 H, J=5.4, 11.5 Hz, $CH_2OCO$), 3.83 (s, 3 H, $OCH_3$), 3.49 (s, 2 H, $OCCH_2Ar$), 3.1–3.35 (m, 4 H, $CH_2NH$ and $OCH_2CH_2NH_2$), 2.58 (m, 2 H, $CH_2CH_2Ar$), 2.22 (dd, 6 H, 2×$CH_3$), 1.85 (m, 1 H, CH), 1.55 (m, 2 H, $CH_2CH_2Ar$), 1.18 (s, 9 H, $COC(CH_3)_3$). MS m/z: 498 ($M^+$)

Example 27

N-[4-(4-tert-Butylphenyl)-2-(pivaloyloxymethyl) butyl]-2-[4-(2-aminoethoxy)-3-methoxyphenyl] acetamide (39)

The compound 39 was prepared by the same procedure with that described in above Procedure D.

94% yield, a colorless oil. $^1$H-NMR ($CDCl_3$) δ: 7.30 (d, 2 H, J=8.2 Hz), 7.04 (d, 2 H, J=8.3 Hz), 6.7–6.9 (m, 3 H), 5.86 (bt, 1 H, J=6.0 Hz, NH), 4.06 (t, 2 H, J=4.9 Hz, $OCH_2CH_2NH_2$), 4.02 (dd, 1 H, J=4.4, 11.5 Hz, $CH_2OCO$), 3.94 (dd, 1 H, J=5.4, 11.5 Hz, $CH_2OCO$), 3.82 (s, 3 H, $OCH_3$), 3.48 (s, 2 H, $OCCH_2Ar$), 3.1–3.35 (m, 4 H, $CH_2NH$ and $OCH_2CH_2NH_2$), 2.58 (m, 2 H, $CH_2CH_2Ar$), 1.85 (m, 1 H, CH), 1.54 (m, 2 H, $CH_2CH_2Ar$), 1.30 (s, 3 H, $C(CH_3)_3$), 1.18 (s, 9 H, $COC(CH_3)_3$). MS m/z: 527 ($MH^+$)

General Procedure for the Preparation of Compounds 41~43:

A mixture of N-(diphenylmethylene)glycine ethyl ester (40) (3 mmol, 800 mg) and potassium hydroxide (9 mmol, 505 mg) in dimethylsulfoxide (5 ml) was treated with benzyl halide (3 mmol) at 0° C. and stirred for 30 min at room temperature. A reaction mixture was neutralized with 1 N hydrochloric acid and extracted with EtOAc several times. The combined organic layers were washed with water and brine, dried over $MgSO_4$ and concentrated in vacuo. The residue was purified by flash column chromatography on silica gel with EtOAc/hexanes (1:10) as an eluant to afford compounds 41~43.

Example 28

Ethyl 3-(3,4-Dimethylphenyl)-2-[(diphenylmethylene)amino]propanoate (41)

The compound 41 was prepared by the same procedure with that described in above General Procedure.

42% yield, yellow oil. $^1$H-NMR ($CDCl_3$) δ: 7.55 (m, 2 H), 7.2–7.45 (m, 6 H), 6.6–7.0 (m, 5 H), 4.1–4.3 (m, 3 H, $NCHCO_2CH_2$), 3.0–3.4 (m, 2 H, $CH_2Ar$), 2.1–2.2 (m, 6 H, 2×$CH_3$),1.26 (m, 3 H, $CO_2CH_2CH_3$).

Example 29

Ethyl 3-(4-tert-Butylphenyl)-2-[(diphenylmethylene) amino]propanoate (42)

The compound 42 was prepared with 4-tert-butylbenzyl halide by the same procedure with that described in above General Procedure.

70% yield, white solid. $^1$H-NMR ($CDCl_3$) δ: 7.58 (d, 2 H, J=8.3 Hz), 7.15–7.4 (m, 10 H), 6.94 (d, 2 H, J=8.0 Hz), 4.1–4.25 (m, 3 H, $NCHCO_2CH_2$), 3.24 (dd of AB, 1 H, J=4.1, 13.2 Hz, $CH_2Ar$), 3.12 (dd of AB, 1 H, J=9.2, 13.2 Hz, $CH_2Ar$), 1.30 (s, 9 H, $C(CH_3)_3$), 1.25 (t, 3 H, J=7.0 Hz, $CO_2CH_2CH_3$).

Example 30

Ethyl 4-(3,4-Dimethylphenyl)-2-[(diphenylmethylene)amino]butanoate (43)

The compound 43 was prepared with 4-(2-bromoethyl)-1,2-dimethyl benzene by the same procedure with that described in above General Procedure. 65% yield, yellow oil. $^1$H-NMR ($CDCl_3$) δ: 7.66 (m, 2 H), 7.35–7.5 (m, 6 H), 7.14 (m, 2 H), 6.85–7.0 (m, 3 H), 4.0–4.25 (m, 3 H, $NCHCO_2CH_2$), 2.4–2.6 (m, 2 H, $CH_2Ar$), 2.15–2.3 (m, 8 H, 2×$CH_3$ and $NCHCH_2$),1.26 (t, 3 H, J=5.0 Hz, $CO_2CH_2CH_3$).

General Procedure for the Preparation of Compounds 44~46:

A solution of compound (1 mmol) in tetrahydrofuran (10 ml) was adjusted to pH 4 with 1 N hydrochloric acid and stirred for 30 min. The mixture was neutralized with 1 N sodium hydroxide solution and extracted with ethyl acetate several times. The combined organic layers were washed with water and brine, dried over $MgSO_4$ and concentrated in vacuo. The residue was purified by flash column chromatography on silica gel with EtOAc/hexanes (1:2) as an eluant to afford compounds 44~46.

Example 31

Ethyl 2-Amino-3-(3,4-dimethylphenyl) propanoate (44)

The compound 44 was prepared with compound 41 by the same procedure with that described in above General Procedure.

61% yield, yellow oil. $^1$H-NMR ($CDCl_3$) δ: 6.9–7.1 (m, 3 H), 4.1–4.25 (m, 2 H, $CO_2CH_2$), 3.70 (m, 1 H, $NH_2CH$), 3.0–3.2 (m, 1 H, $CH_2Ar$), 2.80 (m, 1 H, $CH_2Ar$), 2.2–2.3 (m, 6 H, 2×$CH_3$), 1.25 (m, 3 H, $CO_2CH_2CH_3$).

Example 32

Ethyl 2-Amino-3-(4-tert-butylphenyl) propanoate (45)

The compound 45 was prepared with compound 42 by the same procedure with that described in above General Procedure.

81% yield, yellow oil. $^1$H-NMR ($CDCl_3$) δ: 7.32 (d, 2 H, J=8.3 Hz), 7.13 (d, 2 H, J=8.3 Hz), 4.17 (q, 2 H, J=7.1 Hz, $CO_2CH_2$), 3.70 (dd, 1 H, J=5.2, 8.0 Hz, $NH_2CH$), 3.05 (dd of AB, 1 H, J=5.2, 13.5 Hz, $CH_2Ar$), 3.82 (dd of AB, 1 H, J=8.0, 13.5 Hz, $CH_2Ar$), 1.30 (s, 9 H, $C(CH_3)_3$), 1.23 (t, 3 H, J=7.1 Hz, $CO_2CH_2CH_3$).

Example 33

Ethyl 2-Amino-4-(3,4-dimethylphenyl) butanoate (46)

The compound 46 was prepared with compound 43 by the same procedure with that described in above General Procedure.

82% yield, yellow oil. $^1$H-NMR ($CDCl_3$) δ: 6.9–7.1 (m, 3 H), 4.18 (q, 2 H, J=7.1 Hz, $CO_2CH_2$), 3.45 (dd, 1 H, J=5.4, 7.8 Hz, $NH_2CH$), 2.6–2.7 (m, 2 H, $CH_2Ar$), 2.3–2.4 (m, 6 H, 2×$CH_3$), 2.05 (m, 1 H, $CH_2CH_2Ar$), 1.82 (m, 1 H, $CH_2CH_2Ar$), 1.28 (m, 3 H, J=7.1 Hz, $CO_2CH_2CH_3$).

General Procedure for the Preparation of Compounds 47~49:

A mixture of compound (1 mmol) and di-tert-butyl dicarbonate (1.2 mmol) in tetrahydrofuran (5 ml) was stirred for 16 hrs and concentrated in vacuo. The residue was purified by flash column chromatography on silica gel with EtOAc/hexanes (1:4) as an eluant to afford compounds 47~49.

Example 34

Ethyl 2-[(tert-Butoxycarbonyl)amino]-3-(3,4-dimethylphenyl) propanoate (47)

The compound 47 was prepared with compound 44 by the same procedure with that described in above General Procedure.

100% yield, colorless oil. $^1$H-NMR ($CDCl_3$) δ: 6.85–7.1 (m, 3 H), 4.96 (m, 1 H, NH), 4.50 (m, 1 H, NHCH), 4.1–4.2 (m, 2 H, $CO_2CH_2$), 3.0–3.2 (m, 2 H, $CH_2Ar$), 2.2–2.35 (m, 6 H, 2×$CH_3$), 1.41 (d, 9 H, J=6.8 Hz, $CO_2C(CH_3)_3$), 1.2–1.3 (t, 3 H, $CO_2CH_2CH_3$).

Example 35

Ethyl 2-[(tert-Butoxycarbonyl)amino]-3-(4-tert-butylphenyl) propanoate (48)

The compound 48 was prepared with compound 45 by the same procedure with that described in above General Procedure.

100% yield, colorless oil. $^1$H-NMR ($CDCl_3$) δ: 7.30 (d, 2 H, J=8.3 Hz), 7.06 (d, 2 H, J=8.3 Hz), 4.96 (bd, 1 H, NH), 4.56 (m, 1 H, NHCH), 4.16 (q, 2 H, J=7.1 Hz, $CO_2CH_2$), 3.04 (d, 2 H, $CH_2Ar$), 1.42 (s, 9 H, $CO_2C(CH_3)_3$), 1.30 (s, 9 H, $C(CH_3)_3$), 1.22 (t, 3 H, J=7.1 Hz, $CO_2CH_2CH_3$).

Example 36

Ethyl 2-[(tert-Butoxycarbonyl)amino]-4-(3,4-dimethylphenyl) butanoate (49)

The compound 49 was prepared with compound 46 by the same procedure with that described in above General Procedure.

94% yield, colorless oil. $^1$H-NMR ($CDCl_3$) δ: 6.90–7.1 (m, 3 H), 5.08 (d, J=7.5 Hz, 1 H, NH), 4.32 (m, 1 H, NHCH), 4.16 (q, 2 H, J=7.1 Hz, $CO_2CH_2$), 2.5–2.7 (m, 2 H, $CH_2Ar$), 2.2–2.35 (m, 6 H, 2×$CH_3$), 2.10 (m, 1 H, $CH_2CH_2Ar$), 1.90 (m, 1 H, $CH_2CH_2Ar$), 1.45 (s, 9 H, $CO_2C(CH_3)_3$), 1.23 (t, 3 H, J=7.1 Hz, $CO_2CH_2CH_3$).

General Procedure for the Preparation of Compounds 50~52:

A cooled suspension of lithium aluminium hydride (2 mmol) in diethyl ether (10 ml) at 0° C. was treated dropwise with compound (1 mmol) in diethyl ether (10 ml). After being stirred for 1 hr at room temperature, the mixture was cooled and quenched with $H_2O$ (1 ml), 15% NaOH solution (2 ml) and $H_2O$ (3 ml) successively. The suspension was filtered and washed with EtOAc and the filtrate was concentrated. The residue was purified by flash column chromatography on silica gel with EtOAc/hexanes (4:1) as an eluant to afford compounds 50~52.

Example 37 tert-Butyl N-[3-(3,4-dimethylphenyl)-1-(hydroxymethyl)propyl]carbamate (50)

The compound 50 was prepared with compound 47 by the same procedure with that described in above General Procedure.

85% yield, colorless oil. $^1$H-NMR ($CDCl_3$) δ: 6.9–7.1 (m, 3 H), 4.70 (bs, 1 H, NH), 3.82 (bs, 1 H, NHCH), 3.5–3.7 (m, 2 H, $CH_2OH$), 2.7–2.9 (m, 2 H, $CH_2Ar$), 2.2–2.3 (m, 6 H, 2×$CH_3$), 1.42 (s, 9 H, $CO_2C(CH_3)_3$).

Example 38 tert-Butyl N-[3-(4-tert-butylphenyl)-1-(hydroxymethyl)propyl]carbamate (51)

The compound 51 was prepared with compound 48 by the same procedure with that described in above General Procedure.

80% yield, white solid. $^1$H-NMR ($CDCl_3$) δ: 7.32 (d, 2 H, J=8.3 Hz), 7.13 (d, 2 H, J=8.3 Hz), 4.70 (bs, 1 H, NH), 3.86 (bs, 1 H, NHCH), 3.67 (dd, 1 H, J=3.4, 11.0 Hz, $CH_2OH$), 3.55 (dd, 1 H, J=5.6, 11.0 Hz, $CH_2OH$), 2.80 (d, 2 H, J=7.3 Hz, $CH_2Ar$), 1.41 (s, 9 H, $CO_2C(CH_3)_3$), 1.30 (s, 9 H, $C(CH_3)_3$).

Example 39 tert-Butyl N-[2-(3,4-dimethylphenyl)-1-(hydroxymethyl)ethyl]carbamate (52)

The compound 52 was prepared with compound 49 by the same procedure with that described in above General Procedure.

96% yield, colorless oil. $^1$H-NMR ($CDCl_3$) δ: 6.9–7.1 (m, 3 H), 4.70 (bs, 1 H, NH), 3.82 (bs, 1 H, NHCH), 3.5–3.7 (m, 2 H, $CH_2OH$), 2.7–2.9 (m, 2 H, $CH_2Ar$), 2.2–2.3 (m, 6 H, 2×$CH_3$), 2.05 (m, 1 H, $CH_2CH_2Ar$), 1.85 (m, 1 H, $CH_2CH_2Ar$), 1.42 (s, 9 H, $CO_2C(CH_3)_3$).

General Procedure for the Preparation of Compounds 53~55:

A cooled solution of compound (1 mmol), triethylamine (3 mmol) and dimethylaminopyridine (0.1 mmol) at 0° C. in $CH_2Cl_2$ (10 ml) was treated with pivaloyl chloride (1.5 mmol) and stirred for 1 hr at room temperature. The mixture was concentrated in vacuo and the residue was purified by flash column chromatography on silica gel with EtOAc/hexanes (1:4) as an eluant to afford compounds 53~55.

Example 40

2-[(tert-Butoxycarbonyl)amino]-3-(3,4-dimethylphenyl)propyl pivalate (53)

The compound 53 was prepared with compound 50 by the same procedure with that described in above General Procedure.

99% yield, colorless oil. $^1$H-NMR ($CDCl_3$) δ: 6.85–7.1 (m, 3 H), 4.61 (d, 1 H, NH), 3.95–4.1 (m, 3 H, $CH_2OCO$ and NHCH), 2.6–2.9 (m, 2 H, $CH_2Ar$), 2.2–2.3 (m, 6 H, 2×$CH_3$), 1.42 (s, 9 H, $CO_2C(CH_3)_3$), 1.23 (s, 9 H, $COC(CH_3)_3$).

Example 41

2-[(tert-Butoxycarbonyl)amino]-3-(4-tert-butylphenyl)propyl pivalate (54)

The compound 54 was prepared with compound 25 by the same procedure with that described in above General Procedure.

99% yield, white solid. $^1$H-NMR ($CDCl_3$) δ: 7.31 (d, 2 H, J=8.3 Hz), 7.10 (d, 2 H, J=8.3 Hz), 4.57 (bs, 1 H, NH), 4.0–4.2 (m, 3 H, $CH_2OCO$ and NHCH), 2.75–2.9 (m, 2 H, $CH_2Ar$), 1.41 (s, 9 H, $CO_2C(CH_3)_3$), 1.30 (s, 9 H, $C(CH_3)_3$), 1.23 (s, 9 H, $COC(CH_3)_3$).

Example 42

2-[(tert-Butoxycarbonyl)amino]-4-(3,4-dimethylphenyl)butyl pivalate (55)

The compound 55 was prepared with compound 52 by the same procedure with that described in above General Procedure.

87% yield, white solid. $^1$H-NMR ($CDCl_3$) δ: 6.9–7.1 (m, 3 H), 4.52 (d, 1 H, NH), 3.9–4.2 (m, 3 H, $CH_2OCO$ and NHCH), 2.6–2.8 (m, 2 H, $CH_2Ar$), 2.2–2.3 (m, 6 H, 2×$CH_3$), 1.6–1.8 (m, 2 H, $CH_2CH_2Ar$), 1.45 (s, 9 H, $CO_2C(CH_3)_3$), 1.20 (s, 9 H, $COC(CH_3)_3$).

Example 43

N-[3-(3,4-Dimethylphenyl)-1-pivaloyloxy-2-propyl]-N'-[4-(methoxymethoxy)-3-methoxybenzyl] thiourea (59)

The compound 59 was prepared with compound 53 by the same procedure with that described in above General Procedure A.

97% yield, yellow oil. $^1$H-NMR ($CDCl_3$) δ: 6.7–7.1 (m, 6 H), 6.36 (bs, 1 H, NH), 6.03 (d, 1 H, J=8.0 Hz, NH), 5.21 (s, 2 H, $OCH_2O$), 4.70 (m, 1 H, CH), 4.46 (bs, 2 H, $NHCH_2Ar$), 4.15 (dd, 1 H, J=5.1, 11.5 Hz, $CH_2OCO$), 3.98 (dd, 1 H, J=4.7, 11.5 Hz, $CH_2OCO$), 3.85 (s, 3 H, $OCH_3$), 3.50 (s, 3 H, $OCH_3$), 2.98 (dd, 1 H, J=5.1, 13.4 Hz, $CH_2Ar$), 2.68 (dd, 1 H, J=8.3, 13.4 Hz, $CH_2Ar$), 2.2–2.3 (m, 6 H, 2×$CH_3$), 1.19 (s, 9 H, $COC(CH_3)_3$).

Example 44

N-[3-(4-tert-Butylphenyl)-1-pivaloyloxy-2-propyl]-N'-[4-(methoxymethoxy)-3-methoxybenzyl] thiourea (60)

The compound 45 was prepared with compound 54 by the same procedure with that described in above General Procedure A.

52% yield, yellow oil. $^1$H-NMR ($CDCl_3$) δ: 7.31 (d, 2 H, J=8.3 Hz), 7.12 (d, 2 H, J=8.3 Hz), 7.10 (d, 1 H, J=8 Hz), 6.88 (d, 1 H, J=1.7 Hz), 6.80 (dd, 1 H, J=1.7, 8 Hz), 6.42 (bs, 1 H, NH), 6.04 (d, 1 H, J=7.6 Hz, NH), 5.21 (s, 2 H, $OCH_2O$), 4.70 (bs, 1 H, CH), 4.48 (bs, 2 H, $NHCH_2Ar$), 4.16 (dd, 1 H, J=6.3, 11.4 Hz, $CH_2OCO$), 3.98 (dd, 1 H, J=4.6, 11.4 Hz, $CH_2OCO$), 3.86 (s, 3 H, $OCH_3$), 3.50 (s, 3 H, $OCH_3$), 3.01 (dd, 1 H, J=4.6, 13.4 Hz, $CH_2Ar$), 2.73 (dd, 1 H, J=8.0, 13.4 Hz, $CH_2Ar$), 1.30 (s, 9 H, $C(CH_3)_3$), 1.18 (s, 9 H, $COC(CH_3)_3$).

Example 45

N-[4-(3,4-Dimethylphenyl)-1-pivaloyloxy-2-butyl]-N'-[4-(methoxymethoxy)-3-methoxybenzyl] thiourea (61)

The compound 61 was prepared with compound 55 by the same procedure with that described in above General Procedure A.

64% yield, white solid. $^1$H-NMR ($CDCl_3$) δ: 6.8–7.1 (m, 6 H), 6.52 (bs, 1 H, NH), 5.94 (bs, 1 H, NH), 5.20 (s, 2 H, $OCH_2O$), 4.52 (bs, 2 H, $NHCH_2Ar$), 4.26 (dd, 1 H, J=4.4, 11.5 Hz, $CH_2OCO$), 3.96 (bs, 1 H, $CH_2OCO$), 3.85 (s, 3 H, $OCH_3$), 3.49 (s, 3 H, $OCH_3$), 2.5–2.7 (m, 2 H, $CH_2Ar$), 2.1–2.3 (m, 6 H, 2×$CH_3$), 1.80 (m, 2 H, $CH_2CH_2Ar$), 1.14 (s, 9 H, $COC(CH_3)_3$).

Example 46

N-[3-(3,4-Dimethylphenyl)-1-pivaloyloxy-2-propyl]-N'-[4-hydroxy-3-methoxybenzyl] thiourea (62)

The compound 62 was prepared with compound 59 by the same procedure with that described in above General Procedure B.

61% yield, white solid. mp=43–48° C. $^1$H-NMR ($CDCl_3$) δ: 6.7–7.1 (m, 6 H), 6.21 (bs, 1 H, NH), 5.94 (m, 1H, NH), 5.62 (bs, 1 H, OH), 4.68 (bs, 1 H, CH), 4.40 (bs, 2 H, $NHCH_2Ar$), 4.15 (m, 1 H, $CH_2OCO$), 4.00 (m, 1 H, $CH_2OCO$), 3.87 (s, 3 H, $OCH_3$), 3.00 (m, 1 H, $CH_2Ar$), 2.76 (m, 1 H, $CH_2Ar$), 2.2–2.3 (m, 6 H, 2×$CH_3$), 1.18 (s, 9 H, $COC(CH_3)_3$). MS m/z: 459 ($MH^+$)

Example 47

N-[3-(4-tert-Butylphenyl)-1-pivaloyloxy-2-propyl]-N'-[4-hydroxy-3-methoxybenzyl]thiourea (63)

The compound 63 was prepared with compound 60 by the same procedure with that described in above General Procedure B.

62% yield, white solid. mp=117–119° C. $^1$H-NMR ($CDCl_3$) δ: 7.30 (d, 2 H, J=8.3 Hz), 7.10 (d, 2 H, J=8.3 Hz), 6.75–6.8 (m, 2 H), 6.69 (dd, 1 H, J=1.7, 8 Hz), 6.42 (bs, 1 H, NH), 6.02 (d, 1 H, J=8.0 Hz, NH), 5.67 (bs, 1 H, OH), 4.70 (bs, 1 H, CH), 4.42 (bs, 2 H, $NHCH_2Ar$), 4.16 (dd, 1 H, J=5.1, 11.5 Hz, $CH_2OCO$), 3.98 (dd, 1 H, J=4.4, 11.4 Hz, $CH_2OCO$), 3.86 (s, 3 H, $OCH_3$), 3.00 (dd, 1 H, J=4.9, 13.4 Hz, $CH_2Ar$), 2.72 (dd, 1 H, J=8.0, 13.4 Hz, $CH_2Ar$), 1.30 (s, 9 H, $C(CH_3)_3$), 1.18 (s, 9 H, $COC(CH_3)_3$). MS m/z: 487 ($MH^+$)

Example 48

N-[4-(3,4-Dimethylphenyl)-1-pivaloyloxy-2-butyl]-N'-[4-hydroxy-3 -methoxybenzyl]thiourea (64)

The compound 64 was prepared with compound 61 by the same procedure with that described in above General procedure B.

76% yield, white solid. $^1$H-NMR ($CDCl_3$) δ: 6.7–7.0 (m, 6 H), 6.53 (bs, 1 H, NH), 5.92 (bs, 1 H, NH), 5.69 (s, 1 H, OH), 4.46 (bs, 2 H, $NHCH_2Ar$), 4.25 (dd, 1 H, J=4.6, 11.5 Hz, $CH_2OCO$), 3.96 (bs, 1 H, $CH_2OCO$), 3.85 (s, 3 H, $OCH_3$), 2.57 (t, 2 H, J=7.6 Hz, $CH_2Ar$), 2.1–2.3 (m, 6 H, 2×$CH_3$), 1.80 (m, 2 H, $CH_2CH_2Ar$), 1.14 (s, 9 H, $COC(CH_3)_3$). MS m/z: 473 ($MH^+$)

Example 49

N-[3-(3,4-dimethylphenyl)-1-pivaloyloxy-2-propyl]-N-[4-hydroxy-3-methoxybenzyl]urea (68)

The compound 68 was prepared with 4-[(methoxymethyl)oxy]-3-methoxybenzyl isocyanate by the same procedure with that described in above General Procedure A and B.

$^1$H-NMR ($CDCl_3$) δ: 6.8–7.1 (m, 6 H), 6.20 (bs, 1 H, NH), 5.92 (m, 1 H, NH), 5.60 (bs, 1 H, OH), 4.38 (bs, 1 H, CH), 4.12 (bs, 2 H, $NHCH_2Ar$), 4.12 (m, 1 H, $CH_2OCO$), 3.98 (m, 1 H, $CH_2OCO$), 3.85 (s, 3 H, $OCH_3$), 2.98 (m, 1 H, $CH_2Ar$), 2.75 (m, 1 H, $CH_2Ar$), 2.2–2.3 (m, 6 H, 2×$CH_3$), 1.18 (s, 9 H, $COC(CH_3)_3$). MS m/z: 443 ($MH^+$)

Example 50

N-[3-(4-tert-dimethylphenyl)-1-pivaloyloxy-2-propyl]-N-[4-hydroxy-3-methoxybenzyl]urea (69)

The compound 69 was prepared with 4-[(methoxymethyl)oxy]-3-methoxybenzyl isocyanate by the same procedure with that described in above General Procedure A and B.

$^1$H-NMR ($CDCl_3$) δ: 7.28 (d, 2 H, J=8.3 Hz), 7.08 (d, 2 H, J=8.3 Hz), 6.7–6.9 (m, 3 H), 6.40 (bs, 1 H, NH), 5.96 (d, 1 H, J=8.0 Hz, NH), 5.65 (bs, 1 H, OH), 4.32 (bs, 1 H, CH), 4.11 (bs, 2 H, $NHCH_2Ar$), 4.02 (dd, 1 H, J=5.1, 11.5 Hz, $CH_2OCO$), 3.94 (dd, 1 H, J=4.4, 11.4 Hz, $CH_2OCO$), 3.83 (s, 3 H, $OCH_3$), 2.98 (dd, 1 H, J=4.9, 13.4 Hz, $CH_2Ar$), 2.70 (dd, 1 H, J=8.0, 13.4 Hz, $CH_2Ar$), 1.30 (s, 9 H, $C(CH_3)_3$), 1.18 (s, 91 H, $COC(CH_3)_3$). MS m/z: 471 ($MH^+$)

Example 51

N-[3-(3,4-dimethylphenyl)-1-pivaloyloxy-2-propyl]-N-[4-hydroxy-3-methoxybenzyl]urea (70)

The compound 70 was prepared with 4-[(methoxymethyl) oxy]-3-methoxybenzyl isocyanate by the same procedure with that described in above General Procedure A and B.

$^1$H-NMR ($CDCl_3$) δ: 6.75–7.0 (m, 6 H), 6.52 (bs, 1 H, NH), 5.90 (bs, 1 H, NH), 5.65 (s, 1 H, OH), 4.16 (bs, 2 H, $NHCH_2Ar$), 4.08 (dd, 1 H, J=4.6, 11.5 Hz, $CH_2OCO$), 3.94 (bs, 1 H, $CH_2OCO$), 3.83 (s, 3 H, $OCH_3$), 2.54 (t, 2 H, J=7.6 Hz, $CH_2Ar$), 2.1–2.3 (m, 6 H, 2×$CH_3$), 1.80 (m, 2 H, $CH_2CH_2Ar$), 1.14 (s, 9 H, $COC(CH_3)_3$). MS m/z: 457 ($MH^+$)

Example 52

N-[3-(3,4-Dimethylphenyl)-1-pivaloyloxy-2-propyl]-N'-[4-(2-azidoethoxy)-3-methoxybenzyl] thiourea (71)

The compound 71 was prepared by the same procedure with that described in above General Procedure A.

62% yield, yellow oil. $^1$H-NMR ($CDCl_3$) δ: 6.75–7.05 (m, 6 H), 6.27 (bs, 1 H, NH), 5.99 (d, 1 H, J=7.9 Hz, NH), 4.65 (bs, 1 H, CH), 4.46 (bs, 2 H, $NHCH_2Ar$), 4.1–4.2 (m, 3 H, $OCH_2CH_2N_3$ and $CH_2OCO$), 3.98 (dd, 1 H, J=4.6, 11.5 Hz, $CH_2OCO$), 3.85 (s, 3 H, $OCH_3$), 3.64 (t, 2 H, J=5.1 Hz, $OCH_2CH_2N_3$), 2.99 (dd, 1 H, J=5.1, 13.4 Hz, $CH_2Ar$), 2.68 (dd, 1 H, J=8.0, 13.4 Hz, $CH_2Ar$), 2.2–2.3 (m, 6 H, 2×$CH_3$), 1.19 (s, 9 H, $C(CH_3)_3$)

Example 53

N-[3-(4-tert-Butylphenyl)-1-pivaloyloxy-2-propyl]-N'-[4-(2-azidoethoxy)-3-methoxybenzyl] thiourea (72)

The compound 72 was prepared by the same procedure with that described in above General Procedure A.

92% yield, yellow oil. $^1$H-NMR ($CDCl_3$) δ: 7.31 (d, 2 H, J=8.3 Hz), 7.12 (d, 2 H, J=8.3 Hz), 6.8–6.9 (m, 3 H), 6.48 (bs, 1 H, NH), 6.06 (d, 1 H, J=7.8 Hz, NH), 4.69 (bs, 1 H, CH), 4.48 (bs, 2 H, $NHCH_2Ar$), 4.1–4.2 (m, 3 H, $OCH_2CH_2N_3$ and $CH_2OCO$), 3.98 (dd, 1 H, J=4.6, 11.5 Hz, $CH_2OCO$), 3.84 (s, 3 H, $OCH_3$), 3.62 (t, 2 H, J=5.1 Hz, $OCH_2CH_2N_3$), 3.01 (dd, 1 H, J=5.1, 13.4 Hz, $CH_2Ar$), 2.73 (dd, 1 H, J=8.0, 13.4 Hz, $CH_2Ar$), 1.30 (s, 9 H, $C(CH_3)_3$), 1.18 (s, 9 H, $C(CH_3)_3$)

Example 54

N-[4-(3,4-Dimethylphenyl)-1-pivaloyloxy-2-butyl]-N'-[4-(2-azidoethoxy)-3-methoxybenzyl] thiourea (73)

The compound 73 was prepared by the same procedure with that described in above General Procedure A.

86% yield, yellow oil. $^1$H-NMR ($CDCl_3$) δ: 6.8–7.1 (m, 6 H), 6.52 (bs, 1 H, NH), 5.94 (bs, 1 H, NH), 4.52 (bs, 2 H, $NHCH_2Ar$), 4.26 (dd, 1 H, J=4.4, 11.5 Hz, $CH_2OCO$), 4.17 (t, 2 H, J=5.4 Hz, $OCH_2CH_2N_3$), 3.96 (bs, 1 H, $CH_2OCO$), 3.85 (s, 3 H, $OCH_3$), 3.62 (t, 2 H, J=6.7 Hz, $OCH_2CH_2N_3$), 2.5–2.7 (m, 2 H, $CH_2Ar$), 2.1–2.3 (m, 6 H, 2×$CH_3$), 1.80 (m, 2 H, $CH_2CH_2Ar$), 1.14 (s, 9 H, $COC(CH_3)_3$).

Example 55

N-[3-(3,4-Dimethylphenyl)-1-pivaloyloxy-2-propyl]-N'-[4-(2-aminoethoxy)-3-methoxybenzyl] thiourea (74)

The compound 74 was prepared by the same procedure with that described in above General Procedure C.

84% yield, white solid, mp=62–63° C. $^1$H-NMR ($CDCl_3$) δ: 6.75–7.05 (m, 6 H), 6.59 (bt, 1 H, NH), 6.23 (d, 1 H, J=6.6 Hz, NH), 4.72 (bs, 1 H, CH), 4.46 (bs, 2 H, $NHCH_2Ar$), 4.13 (dd, 1 H, J=5.1, 11.2 Hz, $CH_2OCO$), 3.95–4.05 (m, 3 H, $OCH_2CH_2NH_2$ and $CH_2OCO$), 3.82 (s, 3 H, $OCH_3$), 3.12 (t, 2 H, J=4.6 Hz, $OCH_2CH_2NH_2$), 2.99 (dd, 1 H, J=5.1, 13.4 Hz, $CH_2Ar$), 2.5–2.75 (m, 3 H, $NH_2$ and $CH_2Ar$), 2.2–2.3 (m, 6 H, 2×$CH_3$), 1.19 (s, 9 H, $C(CH_3)_3$) MS m/z: 502 ($MH^+$)

Example 56

N-[3-(4-tert-Butylphenyl)-1-pivaloyloxy-2-propyl]-N'-[4-(2-aminoethoxy)-3-methoxybenzyl] thiourea (75)

The compound 75 was prepared by the same procedure with that described in above General Procedure C.

98% yield, white solid, mp=63–65° C. $^1$H-NMR ($CDCl_3$) δ: 7.30 (d, 2 H, J=8.3 Hz), 7.13 (d, 2 H, J=8.3 Hz), 6.86 (bs, 1 H), 6.79 (bs, 2 H), 6.68 (bs, 1 H, NH), 6.26 (d, 1 H, J=7.05 Hz, NH), 4.73 (bs, 1 H, CH), 4.48 (bs, 2 H, $NHCH_2Ar$), 4.15 (dd, 1 H, J=4.9, 11.5 Hz, $CH_2OCO$), 3.95–4.05 (m, 3 H, $OCH_2CH_2NH_2$ and $CH_2OCO$), 3.82 (s, 3 H, $OCH_3$), 3.11 (t, 2 H, J=4.9 Hz, $OCH_2CH_2NH_2$), 3.02 (dd, 1 H, J=5.1, 13.4 Hz, $CH_2Ar$), 2.65–2.8 (m, 3 H, $NH_2$ and $CH_2Ar$), 1.30 (s, 9 H, $C(CH_3)_3$), 1.19 (s, 9 H, $C(CH_3)_3$). MS m/z: 530 ($MH^+$)

Example 57

N-[4-(3,4-Dimethylphenyl)-1-pivaloyloxy-2-butyl]-N'-[4-(2-aminoethoxy)-3-methoxybenzyl] thiourea (76)

The compound 76 was prepared by the same procedure with that described in above General Procedure C.

94% yield, a colorless oil. $^1$H-NMR ($CDCl_3$) δ: 6.8–7.1 (m, 6 H), 6.52 (bs, 1 H, NH), 5.94 (bs, 1 H, NH), 4.52 (bs, 2 H, $NHCH_2Ar$), 4.26 (dd, 1 H, J=4.4, 11.5 Hz, $CH_2OCO$), 4.06 (t, 2 H, J=4.9 Hz, $OCH_2CH_2NH_2$), 3.96 (bs, 1 H, $CH_2OCO$), 3.85 (s, 3 H, $OCH_3$), 3.25 (m, 2 H, $OCH_2CH_2NH_2$), 2.5–2.7 (m, 2 H, $CH_2Ar$), 2.1–2.3 (m, 6 H, 2×$CH_3$), 1.80 (m, 2 H, $CH_2CH_2Ar$), 1.14 (s, 9 H, $COC(CH_3)_3$). MS m/z: 516 ($MH^+$)

Example 58

N-[3-(3,4-Dimethylphenyl)-1-pivaloyloxy-2-propyl]-N-[4-(2-aminoethoxy-3-methoxybenzyl) urea (80)

The compound 80 was prepared with 4-(2-azidoethoxy)-3-methoxybenzyl isocyanate by the same procedure with that described in General Procedure A and C.

$^1$H-NMR ($CDCl_3$) δ: 6.75–7.05 (m, 6 H), 6.52 (bt, 1 H, NH), 6.20 (d, 1 H, J=6.6 Hz, NH), 4.42 (bs, 1 H, CH), 4.26 (bs, 2 H, NHCH2Ar), 4.10 (dd, 1 H, J=5.1, 11.2 Hz, $CH_2OCO$), 3.95–4.05 (m, 3 H, $OCH_2CH_2NH_2$ and $CH_2OCO$), 3.80 (s, 3 H, $OCH_3$), 3.12 (t, 2 H, J=4.6 Hz, $OCH_2CH_2NH_2$), 2.96 (dd, 1 H, J=5.1, 13.4 Hz, $CH_2Ar$), 2.5–2.75 (m, 3 H, $NH_2$ and $CH_2Ar$), 2.2–2.3 (m, 6 H, 2×$CH_3$), 1.19 (s, 9 H, $C(CH_3)_3$) MS m/z: 486 ($MH^+$)

Example 59

N-[3-(3,4-Dimethylphenyl)-1-pivaloyloxy-2-propyl]-N-[4-(2-aminoethoxy-3-methoxybenzyl) urea (81)

The compound 81 was prepared with 4-(2-azidoethoxy)-3-methoxybenzyl isocyanate by the same procedure with that described in General Procedure A and C.

$^1$H-NMR ($CDCl_3$) δ: 7.28 (d, 2 H, J=8.3 Hz), 7.12 (d, 2 H, J=8.3 Hz), 6.84 (bs, 1 H), 6.76 (bs, 2 H), 6.66 (bs, 1 H, NH), 6.24 (d, 1 H, J=7.05 Hz, NH), 4.43 (bs, 1 H, CH), 4.28 (bs, 2 H, $NHCH_2Ar$), 4.12 (dd, 1 H, J=4.9, 11.5 Hz, $CH_2OCO$), 3.95–4.05 (m, 3 H, $OCH_2CH_2NH_2$ and $CH_2OCO$), 3.80 (s, 3 H, $OCH_3$), 3.11 (t, 2 H, J=4.9 Hz, $OCH_2CH_2NH_2$), 3.00 (dd, 1 H, J=5.1, 13.4 Hz, $CH_2Ar$), 2.65–2.8 (m, 3 H, $NH_2$ and $CH_2Ar$), 1.30 (s, 9 H, $C(CH_3)_3$), 1.19 (s, 9 H, $C(CH_3)_3$). MS m/z: 514 ($MH^+$)

Example 60

N-[3-(3,4-Dimethylphenyl)-1-pivaloyloxy-2-propyl]-N-[4-(2-aminoethoxy-3-methoxybenzyl) urea (82)

The compound 82 was prepared with 4-(2-azidoethoxy)-3-methoxybenzyl isocyanate by the same procedure with that described in General Procedure A and C.

$^1$H-NMR($CDCl_3$) δ: 7.28 (d, 2 H, J=8.3 Hz), 7.12 (d, 2 H, J=8.3 Hz), 6.84 (bs, 1 H), 6.76 (bs, 2 H), 6.66 (bs, 1 H, NH), 6.24 (d, 1 H, J=7.05 Hz, NH), 4.43 (bs, 1 H, CH), 4.28 (bs, 2 H, $NHCH_2Ar$), 4.12 (dd, 1 H, J=4.9, 11.5 Hz, $CH_2OCO$), 3.95–4.05 (m, 3 H, $OCH_2CH_2NH_2$ and $CH_2OCO$), 3.80 (s, 3 H, OCH3), 3.11 (t, 2 H, J=4.9 Hz, $OCH_2CH_2NH_2$), 3.00 (dd, 1 H, J=5.1, 13.4 Hz, $CH_2Ar$), 2.65–2.8 (m, 3 H, $NH_2$ and $CH_2Ar$), 1.30 (s, 9 H, $C(CH_3)_3$), 1.19 (s, 9 H, $C(CH_3)_3$). MS m/z: 514 ($MH^+$)

Example 61

N-[3-(3,4-Dimethylphenyl)-1-pivaloyloxy-2-propyl]-2-[4-hydroxy-3-methoxyphenyl] acetamide (83)

The compound 83 was prepared by the same procedure with that described in above General Procedure A.

78% yield, yellow oil. $^1$H-NMR ($CDCl_3$) δ: 6.6–7.05 (m, 6 H), 5.58 (d, 1 H, J=8.5 Hz, NH), 4.34 (m, 1 H, CH), 3.97 (dd of AB, 2 H, $CH_2OCO$), 3.85 (s, 3 H, $OCH_3$), 3.46 (s, 2 H, $OCCH_2Ar$), 2.68 (ddd of AB, 2 H, $CH_2Ar$), 2.2–2.3 (m, 6 H, 2×$CH_3$), 1.14 (s, 9 H, $C(CH_3)_3$). MS m/z: 428 ($MH^+$)

Example 62

N-[3-(4-tert-Butylphenyl)-1-pivaloyloxy-2-propyl]-2-[4-hydroxy-3-methoxyphenyl]acetamide (84)

The compound 84 was prepared by the same procedure with that described in above General Procedure A.

79% yield, yellow oil. $^1$H-NMR ($CDCl_3$) δ: 7.25 (d, 2 H, J=8.3 Hz) 6.65–7.0 (m, 5 H), 5.58 (d, 1 H, J=8.5 Hz, NH), 4.39 (m, 1 H, CH), 3.97 (ddd of AB, 2 H, $CH_2OCO$), 3.74 (s, 3 H, $OCH_3$), 3.50 (s, 2 H, $OCCH_2Ar$), 2.72 (ddd of AB, 2 H, $CH_2Ar$), 1.28 (s, 9 H, $C(CH_3)_3$), 1.14 (s, 9 H, $C(CH_3)_3$). MS m/z: 456 ($MH^+$)

Example 63

N-[4-(3,4-Dimethylphenyl)-1-pivaloyloxy-2-butyl]-2-[4-hydroxy-3-methoxyphenyl]acetamide (85)

The compound 85 was prepared by the same procedure with that described in above General Procedure A.

76% yield, oil. $^1$H-NMR ($CDCl_3$) δ: 6.6–7.05 (m, 6 H), 5.58 (d, 1 H, 3=8.5 Hz, NH), 4.28 (m, 1 H, CH), 3.97 (dd of AB, 2 H, $CH_2OCO$), 3.85 (s, 3 H, $OCH_3$), 3.46 (s, 2 H, $OCCH_2Ar$), 2.68 (ddd of AB, 2 H, $CH_2Ar$), 2.2–2.3 (m, 6 H, 2×$CH_3$), 1.80 (m, 2 H, $CH_2CH_2Ar$), 1.14 (s, 9 H, $C(CH_3)_3$). MS m/z: 442 ($MH^+$)

Example 64

N-[3-(3,4-Dimethylphenyl)-1-pivaloyloxy-2-propyl]-2-[4-(2-azidoethoxy)-3-methoxyphenyl] acetamide (86)

The compound 86 was prepared by the same procedure with that described in above General Procedure A.

92% yield, yellow oil. $^1$H-NMR ($CDCl_3$) δ: 6.65–7.05 (m, 6 H), 5.52 (d, 1 H, J=8.1 Hz, NH), 4.37 (m, 1 H, CH), 4.16 (t, 2 H, J=5.1 Hz, $OCH_2CH_2N_3$), 3.96 (ddd of AB, 2 H, $CH_2OCO$), 3.83 (s, 3 H, $OCH_3$), 3.62 (t, 2 H, J=5.1 Hz, $OCH_2CH_2N_3$), 3.47 (s, 2 H, $OCCH_2Ar$), 2.74 (dd, 1 H, J=6.1, 13.9 Hz, $CH_2Ar$), 2.63 (dd, 1 H, J=7.8, 13.9 Hz, $CH_2Ar$), 2.2–2.3 (m, 6 H, 2×$CH_3$), 1.14 (s, 9 H, $C(CH_3)_3$).

Example 65

N-[3-(4-tert-Butylphenyl)-1-pivaloyloxy-2-propyl]-2-[4-(2-azidoethoxy)-3-methoxyphenyl] acetamide (87)

The compound 87 was prepared by the same procedure with that described in above General Procedure A.

65% yield, yellow oil. $^1$H-NMR ($CDCl_3$) δ: 7.26 (d, 2 H, J=8.3 Hz), 6.98 (d, 2 H, J=8.3 Hz), 6.85 (d, 1 H, J=8 Hz), 6.65–6.75 (m, 2 H), 5.59 (d, 1 H, J=8.3 Hz, NH), 4.40 (m, 1 H, CH), 4.16 (t, 2 H, J=5.1 Hz, $OCH_2CH_2N_3$), 3.96 (ddd of AB, 2 H, $CH_2OCO$), 3.83 (s, 3 H, $OCH_3$), 3.62 (t, 2 H, J=5.1 Hz, $OCH_2CH_2N_3$), 3.48 (s, 2 H, $OCCH_2Ar$), 2.78 (dd, 1 H, J=6.1, 13.9 Hz, $CH_2Ar$), 2.68 (dd, 1 H, J=7.8, 13.9 Hz, $CH_2Ar$), 1.30 (s, 9 H, $C(CH_3)_3$), 1.14 (s, 9 H, $C(CH_3)_3$).

Example 66

N-[4-(3,4-Dimethylphenyl)-1-pivaloyloxy-2-butyl]-2-[4-(2-azidoethoxy)-3-methoxyphenyl] acetamide (88)

The compound 88 was prepared by the same procedure with that described in above General Procedure A.

62% yield, yellow oil. $^1$H-NMR ($CDCl_3$) δ: 6.6–7.05 (m, 6 H), 5.58 (d, 1 H, J=8.5 Hz, NH), 4.28 (m, 1 H, CH), 4.16 (t, 2 H, J=5.4 Hz, $OCH_2CH_2N_3$), 3.97 (dd of AB, 2 H, $CH_2OCO$), 3.85 (s, 3 H, $OCH_3$), 3.62 (t, 2 H, J=5.4 Hz, $OCH_2CH_2N_3$), 3.46 (s, 2 H, $OCCH_2Ar$), 2.68 (ddd of AB, 2 H, $CH_2Ar$), 2.2–2.3 (m, 6 H, 2×$CH_3$), 1.80 (m, 2 H, $CH_2CH_2Ar$), 1.14 (s, 9 H, $C(CH_3)_3$).

Example 67

N-[3-(3,4-Dimethylphenyl)-1-pivaloyloxy-2-propyl]-2-[4-(2-aminoethoxy)-3-methoxyphenyl] acetamide (89)

The compound 89 was prepared by the same procedure with that described in above General Procedure D.

73% yield, yellow oil. $^1$H-NMR ($CDCl_3$) δ: 6.65–7.05 (m, 6 H), 5.57 (d, 1 H, J=8.3 Hz, NH), 4.35 (m, 1 H, CH), 4.09 (t, 2 H, J=5.1 Hz, $OCH_2CH_2NH_2$), 3.96 (ddd of AB, 2 H, $CH_2OCO$), 3.83 (s, 3 H, $OCH_3$), 3.46 (s, 2 H, $OCCH_2Ar$), 3.19 (t, 2 H, J=5.1 Hz, $OCH_2CH_2NH_2$), 2.92 (bs, 2 H, $NH_2$), 2.74 (dd, 1 H, J=6.1, 13.9 Hz, $CH_2Ar$), 2.63 (dd, 1 H, J=7.8, 13.9 Hz, $CH_2Ar$), 2.2–2.3 (m, 6 H, 2×$CH_3$), 1.14 (s, 9 H, $C(CH_3)_3$). MS m/z: 471 ($MH^+$)

Example 68

N-[3-(4-tert-Butylphenyl)-1-pivaloyloxy-2-propyl]-2-[4-(2-aminoethoxy)-3-methoxyphenyl] acetamide (90)

The compound 90 was prepared by the same procedure with that described in above General Procedure D.

70% yield, yellow oil. $^1$H-NMR ($CDCl_3$) δ: 7.26 (d, 2 H, J=8.3 Hz), 6.98 (d, 2 H, J=8.3 Hz), 6.85 (d, 1 H, J=8 Hz), 6.65–6.75 (m, 2 H), 5.59 (d, 1 H, J=8.3 Hz, NH), 4.40 (m, 1 H, CH), 4.09 (t, 2 H, J=5.1 Hz, $OCH_2CH_2NH_2$), 3.96 (ddd of AB, 2 H, $CH_2OCO$), 3.83 (s, 3 H, $OCH_3$), 3.47 (s, 2 H, $OCCH_2Ar$), 3.18 (t, 2 H, J=5.1 Hz, $OCH_2CH_2NH_2$), 2.95 (bs, 2 H, $NH_2$), 2.78 (dd, 1 H, J=6.1, 13.9 Hz, $CH_2Ar$), 2.68 (dd, 1 H, J=7.8, 13.9 Hz, $CH_2Ar$), 1.29 (s, 9 H, $C(CH_3)_3$), 1.14 (s, 9 H, $C(CH_3)_3$). MS m/z: 499 ($MH^+$)

Example 69

N-[4-(3,4-Dimethylphenyl)-1-pivaloyloxy-2-butyl]-2-[4-(2-aminoethoxy)-3-methoxyphenyl] acetamide (91)

The compound 91 was prepared by the same procedure with that described in above General Procedure D.

68% yield, yellow oil. $^1$H-NMR ($CDCl_3$) δ: 6.65–7.05 (m, 6 H), 5.56 (d, 1 H, J=8.5 Hz, NH), 4.28 (m, 1 H, CH), 3.95–4.1 (m, 4 H, $CH_2OCO$ and $OCH_2CH_2NH_2$), 3.86 (s, 3 H, $OCH_3$), 3.62 (t, 2 H, J=5.4 Hz, $OCH_2CH_2N_3$), 3.46 (s, 2 H, $OCCH_2Ar$), 3.12 (t, 2 H, $OCH_2CH_2NH_2$), 2.68 (ddd of AB, 2 H, $CH_2Ar$), 2.5 (bs, 2 H, $NH_2$), 2.2–2.3 (m, 6 H, 2×$CH_3$), 1.79 (m, 2 H, $CH_2CH_2Ar$), 1.14 (s, 9 H, $C(CH_3)_3$). MS m/z: 485 ($MH^+$)

Example 70

(R)-2-(tert-Butoxycarbonylamino)-3-phenylpropyl pivalate (94)

A cooled solution of (R)-2-(tert-butoxycarbonylamino)-3-phenyl-1-propanol (92) (1 g, 4 mmol) in $CH_2Cl_2$ (20 ml) at 0° C. was treated with triethylamine (1.12 m, 8 mmol), pivaloyl chloride (0.74 ml, 6 mmol) followed by 4-(dimethylamino)pyridine (50 mg 0.4 mmol) and stirred overnight at room temperature. The mixture was concentrated in vacuo and the residue was purified by flash column chromatography on silica gel with EtOAc/hexanes (1:4) as an eluant to give compound 94.

88% yield, white solid mp=59–60° C. $^1$H-NMR ($CDCl_3$) δ: 7.15–7.35 (m, 5 H, Ph), 4.59 (d, 1 H, J=8.4 Hz, NH), 4.12 (m, 1 H, CH), 4.00 (ddd of AB, 2 H, $CH_2OCO$), 2.83 (ddd of AB, 2 H, $CH_2Ph$), 1.41 (s, 9 H, $C(CH_3)_3$), 1.23 (s, 9 H, $C(CH_3)_3$)

Example 71

(S)-2-(tert-Butoxycarbonylamino)-3-phenylpropyl pivalate (95)

The compound 95 was prepared by the same procedure with that described in above Example 70.

Example 72

(R)-2-Amino-3-phenylpropyl pivalate (96)

A cooled solution of compound 94 (1.006 g, 3 mmol) in $CH_2Cl_2$ (10 ml) at 0° C. was treated with trifluoroacetic acid (2.5 ml) and stirred for 1 hr at room temperature. The mixture was concentrated in vacuo to give compound 96 as a yellow oil which was used for the next step without further purification.

$^1$H-NMR ($CDCl_3$) δ: 7.15–7.4 (m, 5 H, Ph), 4.30 (d of AB, 1 H, $CH_2OCO$), 4.16 (d of AB, 1 H, $CH_2OCO$), 3.73 (m, 1 H, CH), 3.05 (ddd of AB, 2 H, $CH_2Ph$), 1.22 (s, 9 H, $C(CH_3)_3$)

Example 73

(S)-2-Amino-3-phenylpropyl pivalate (97)

The compound 97 was prepared by the same procedure with that described in above Example 72.

Example 74

N-[(2R)-3-Phenyl-1-pivaloyloxy-2-propyl]-N'-[4-(methoxymethoxy)-3-methoxybenzyl]thiourea (98)

The compound 98 was prepared by the same procedure with that described in above General Procedure A.

[α]=7.95 (c, 1.0, $CHCl_3$) $^1$H-NMR ($CDCl_3$) δ: 7.15–7.35 (m, 5 H, Ph), 7.09 (d, 1 H, J=8 Hz, $Ar_{H-5}$), 6.85 (d, 1 H, J=1.85 Hz, $Ar_{H-2}$), 6.79 (dd, 1 H, J=1.95, 8 Hz, $Ar_{H-6}$), 6.41 (bs, 1 H, N$\underline{H}$$CH_2$), 6.06 (d, 1 H, J=7.8 Hz, NHCH), 5.21 (s, 2 H, $OCH_2O$), 4.75 (bs, 1 H, CHNH), 4.46 (bs, 2 H, $NHCH_2Ar$), 4.16 (dd, 1 H, J=5.1, 11.5 Hz, $CH_2OCO$), 4.00 (dd, 1 H, J=4.4, 11.5 Hz, $CH_2OCO$), 3.85 (s, 3 H, $OCH_3$), 3.51 (s, 3 H, $CH_2OCH_3$), 3.04 (dd, 1 H, J=5.3, 13.4 Hz, $CH_2Ar$), 2.76 (dd, 1 H, J=8.1, 13.4 Hz, $CH_2Ar$), 1.19 (s, 9 H, $C(CH_3)_3$)

Example 75

N-[(2S)-3-Phenyl-1-pivaloyloxy-2-propyl]-N'-[4-(methoxymethoxy)-3-methoxybenzyl]thiourea (99)

The compound 99 was prepared by the same procedure with that described in above General Procedure A and the spectra were identical to that of compound 98.

[α]=−9.93 (c, 0.55, $CHCl_3$)

Example 76

N-[(2R)-3-Phenyl-1-pivaloyloxy-2-propyl]-N'-(4-hydroxy-3-methoxybenzyl)thiourea (100)

The compound 100 was prepared by the same procedure with that described in above General Procedure B.

[α]=5.42 (c, 0.475, $CHCl_3$) $^1$H-NMR ($CDCl_3$) δ: 7.15–7.32 (m, 5 H, Ph), 6.87 (d, 1 H, J=8 Hz, $Ar_{H-5}$), 6.81 (d, 1 H, J=1.85 Hz, $Ar_{H-2}$), 6.77 (dd, 1 H, J=1.95, 8 Hz, $Ar_{H-6}$), 6.29 (bs, 1 H, $NHCH_2$), 6.00 (d, 1 H, J=8 Hz, NHCH), 5.64 (bs, 1 H, OH), 4.74 (bs, 1 H, CHNH), 4.40 (bs, 2 H, $NHCH_2Ar$), 4.16 (dd, 1 H, J=5.1, 11.5 Hz, $CH_2OCO$), 4.00 (dd, 1 H, J=4.6, 11.5 Hz, $CH_2OCO$), 3.87 (s, 3 H, $OCH_3$), 3.04 (dd, 1 H, J=5.4, 13.4 Hz, $CH_2Ar$), 2.75 (dd, 1 H, J=8.3, 13.4 Hz, $CH_2Ar$), 1.19 (s, 9 H, $C(CH_3)_3$) MS m/z: 431 ($MH^+$)

Example 77

N-[(2S)-3-Phenyl-1-pivaloyloxy-2-propyl]-N]-(4-hydroxy-3-methoxybenzyl)thiourea (101)

The compound 101 was prepared by the same procedure with that described in above General Procedure B and the spectra were identical to that of compound 100.

[α]=−2.58 (c, 0.4, $CHCl_3$) MS m/z: 431 ($MH^+$)

Example 78

N-[(2R)-3-Phenyl-1-pivaloyloxy-2-propyl]-N-[4-hydroxy-3-methoxybenzyl]urea (104)

The compound 104 was prepared by the same procedure with that described in above General Procedure A and B.

$^1$H-NMR ($CDCl_3$) δ: 7.15–7.30 (m, 5 H. Ph), 6.85 (d, 1 H, J=8 Hz), 6.77 (d, 1 H, J=1.85 Hz), 6.74 (dd, 1 H, J=1.95, 8 Hz), 6.29 (bs, 1 H, $NHCH_2$), 6.00 (d, 1 H, J=8 Hz, NHCH), 5.60 (bs, 1 H, OH), 4.34 (bs, 1 H, CHNH), 4.10 (bs, 2 H, $NHCH_2Ar$), 4.12 (dd, 1 H, J=5.1, 11.5 Hz, $CH_2OCO$), 3.98 (dd, 1 H, J=4.6, 11.5 Hz, $CH_2OCO$), 3.85 (s, 3 H, $OCH_3$), 3.00 (dd, 1 H, J=5.4, 13.4 Hz, $CH_2Ar$), 2.74 (dd, 1 H, J=8.3, 13.4 Hz, $CH_2Ar$), 1.19 (s, 9 H, $C(CH_3)_3$) MS m/z: 415 ($MH^+$)

Example 79

N-[(2S)-3-Phenyl-1-pivaloyloxy-2-propyl]-N-[4-hydroxy-3-methoxybenzyl]urea (105)

The compound 105 was prepared by the same procedure with that described in above General Procedure A and B and the spectra were identical to that of compound 104.

MS m/z: 415 ($MH^+$)

Example 80

N-[(2R)-3-Phenyl-1-pivaloyloxy-2-propyl]-N-[4-(2-azidoethoxy)-3-methoxybenzyl]thiourea (106)

The compound 106 was prepared by the same procedure with that described in above General Procedure A.

[α]=12.82 (c, 0.1, $CHCl_3$) $^1$H-NMR ($CDCl_3$) δ: 7.15–7.32 (m, 5 H, Ph), 6.78–6.88 (m, 3 H, Ar), 6.33 (bs, 1 H, $NHCH_2$), 6.03 (d, 1 H, J=7.56 Hz, NHCH), 4.73 (bs, 1 H, CHNH), 4.45 (bs, 2 H, $NHCH_2Ar$), 4.1–4.2 (m, 3 H, $OCH_2CH_2N_3$ and $CH_2OCO$), 4.00 (dd, 1 H, J=4.4, 11.4 Hz, $CH_2OCO$), 3.84 (s, 3 H, $OCH_3$), 3.64 (t, 2 H, J=5.4 Hz, $OCH_2CH_2N_3$), 3.05 (dd, 1 H, J=5.4, 13.6 Hz, $CH_2Ar$), 2.75 (dd, 1 H, J=8.0, 13.6 Hz, $CH_2Ar$), 1.19 (s, 9 H, $C(CH_3)_3$)

Example 81

N-[(2S)-3-Phenyl-1-pivaloyloxy-2-propyl]-N-[4-(2-azidoethoxy)-3-methoxybenzyl]thiourea (107)

The compound 107 was prepared by the same procedure with that described in above General Procedure A and the spectra were identical to that of compound 106.

[α]=−15.36 (c, 0.1, $CHCl_3$)

Example 82

N-[(2R)-3-Phenyl-1-pivaloyloxy-2-propyl]-N-[4-(2-aminoethoxy)-3-methoxybenzyl]thiourea (108)

The compound 108 was prepared by the same procedure with that described in above General Procedure C.

Mp=49° C.

[α]=6.82 (c, 0.1, $CHCl_3$) $^1$H-NMR ($CDCl_3$) δ: 7.18–7.32 (m, 5 H, Ph), 6.75–6.85 (m, 3 H, Ar), 6.56 (bt, 1 H, J=5.1 Hz, $NHCH_2$), 6.22 (d, 1 H, J=7.8 Hz, NHCH), 4.77 (bs, 1 H, CHNH), 4.45 (bs, 2 H, $NHCH_2Ar$), 4.14 (dd, 1 H, J=5.1, 11.5 Hz, $CH_2OCO$), 3.95–4.08 (m, 3 H, $OCH_2CH_2NH_2$ and $CH_2OCO$), 3.82 (s, 3 H, $OCH_3$), 3.12 (t, 2 H, J=5.1 Hz, $OCH_2CH_2NH_2$), 3.05 (dd, 1 H, J=5.3, 13.4 Hz, $CH_2Ar$), 2.76 (dd, 1 H, J=8.0, 13.4 Hz, $CH_2Ar$), 2.40 (bs, 2 H, $NH_2$), 1.19 (s, 9 H, $C(CH_3)_3$) MS m/z: 474 ($MH^+$)

Example 83

N-[(2S)-3-Phenyl-1-pivaloyloxy-2-propyl]-N-[4-(2-aminoethoxy)-3-methoxybenzyl]thiourea (109)

The compound 109 was prepared by the same procedure with that described in above General Procedure C and the spectra were identical to that of compound 108.

Mp=49° C. [α]=−14.66 (c, 0.1, $CHCl_3$) MS m/z: 474 ($MH^+$)

Example 84

N-[(2R)-3-Phenyl-1-pivaloyloxy-2-propyl]-N-(4-(2-aminoethoxy)-3-methoxybenzyl)urea (112)

The compound 112 was prepared by the same procedure with that described in above General Procedure A and C.

$^1$H-NMR ($CDCl_3$) δ: 7.15–7.3 (m, 5 H, Ph), 6.75–6.85 (m, 3 H, Ar), 6.46 (bt, 1 H, J=5.1 Hz, $NHCH_2$), 6.20 (d, 1 H, J=7.8 Hz, NHCH), 4.36 (bs, 1 H, CHNH), 4.1–4.2 (m, 3 H, $NHCH_2Ar$, $CH_2OCO$), 3.95–4.05 (m, 3 H, $OCH_2CH_2NH_2$ and $CH_2OCO$), 3.80 (s, 3 H, $OCH_3$), 3.12 (t, 2 H, J=5.1 Hz, $OCH_2CH_2NH_2$), 3.05 (dd, 1 H, J=5.3, 13.4 Hz, $CH_2Ar$), 2.74 (dd, 1 H, J=8.0, 13.4 Hz, $CH_2Ar$), 2.38 (bs, 2 H, $NH_2$), 1.19 (s, 9 H, $C(CH_3)_3$) MS m/z: 458 ($MH^+$)

Example 85

N-[(2S)-3-Phenyl-1-pivaloyloxy-2-propyl]-N-(4-(2-aminoethoxy)-3-methoxybenzyl)urea (113)

The compound 113 was prepared by the same procedure with that described in above General Procedure A and C and the spectra were identical to that of compound 112.

MS m/z: 458 ($MH^+$)

Example 86

N-[(2R)-3-Phenyl-1-pivaloyloxy-2-propyl]-2-(4-hydroxy-3-methoxyphenyl)acetamide (114)

The compound 114 was prepared by the same procedure with that described in above General Procedure A.

[α]=20.58 (c, 0.1, $CHCl_3$) $^1$H-NMR ($CDCl_3$) δ: 7.2–7.28 (m, 3 H, Ph), 7.0–7.05 (m, 2 H, Ph), 6.78 (dd, 1 H, J=1.7, 8.5 Hz), 6.6–6.68 (m, 2 H, Ar), 5.61 (bs, 1 H, OH), 5.51 (d, 1 H, J=9 Hz, NH), 4.40 (m, 1 H, CH), 3.96 (d of AB, 2 H, J=4.6 Hz, $CH_2OCO$), 3.75 (d, 3 H, J=1.44 Hz, $OCH_3$), 3.45 (s, 2 H, $COCH_2Ar$), 2.75 (ddd of AB, 2 H, $CH_2Ar$), 1.13 (s, 9 H, $C(CH_3)_3$) MS m/z: 400 ($MH^+$)

Example 87

N-[(2S)-3-Phenyl-1-pivaloyloxy-2-propyl]-2-(4-hydroxy-3-methoxyphenyl)acetamide (115)

The compound 115 was prepared by the same procedure with that described in above General Procedure A and the spectra were identical to that of compound 114.

[α]=−23.28 (c, 0.1, $CHCl_3$) MS m/z: 400 ($MH^+$)

Example 88

N-[(2R)-3-Phenyl-1-pivaloyloxy-2-propyl]-2-[4-(2-azidoethoxy)-3-methoxyphenyl]acetamide (116)

The compound 116 was prepared by the same procedure with that described in above General Procedure A.

mp: 77–80° C. [α]=16.30 (c, 0.4, $CHCl_3$) $^1$H-NMR ($CDCl_3$) δ: 7.18–7.25 (m, 3 H, Ph), 7.0–7.1 (m, 2 H, Ph), 6.84 (d, 1 H, J=7.8 Hz, $Ar_{H-5}$), 6.64–6.69 (m, 2 H, Ar), 5.49 (d, 1 H, J=8.3 Hz, NH), 4.39 (m, 1 H, CH), 4.16 (t, 2 H, J=5.1 Hz, $OCH_2CH_2N_3$), 3.95 (ddd of AB, 2 H, $CH_2OCO$), 3.81 (s, 3 H, $OCH_3$), 3.63 (t, 2 H, J=5.1 Hz, $OCH_2CH_2N_3$), 3.45 (s, 2 H, $COCH_2Ar$), 2.73 (ddd of AB, 2 H, $CH_2Ar$), 1.13 (s, 9 H, $C(CH_3)_3$)

Example 89

N-[(2S)-3-Phenyl-1-pivaloyloxy-2-propyl]-2-[4-(2-azidoethoxy)-3-methoxyphenyl]acetamide (117)

The compound 117 was prepared by the same procedure with that described in above General Procedure A and the spectra were identical to that of compound 116.

mp: 77–80° C. [α]=−18.87 (c, 0.55, $CHCl_3$)

Example 90

N-[(2R)-3-Phenyl-1-pivaloyloxy-2-propyl]-2-[4-(2-aminoethoxy)-3-methoxyphenyl]acetamide (118)

The compound 118 was prepared by the same procedure with that described in above General Procedure D.

mp: 70–74° C. [α]=14.34 (c, 0.54, $CHCl_3$) $^1$H-NMR ($CDCl_3$) δ: 7.1–7.2 (m, 3 H, Ph), 6.95–7.0 (m, 2 H, Ph), 6.78 (dd, 1 H, J=6.1, 8.5 Hz), 6.58–6.62 (m, 2 H, Ar), 5.47 (d, 1 H, J=8.5 Hz, NH), 4.33 (m, 1 H, CH), 3.98 (t, 2 H, J=5.1 Hz, $OCH_2CH_2NH_2$), 3.90 (d of AB, 2 H, $CH_2OCO$), 3.75 (s, 3 H, $OCH_3$), 3.38 (s, 2 H, $COCH_2Ar$), 3.07 (t, 2 H, J=5.1 Hz, $OCH_2CH_2NH_2$), 2.68 (ddd of AB, 2 H, $CH_2Ar$), 2.46 (bs, 2 H, $NH_2$), 1.07 (s, 9 H, $C(CH_3)_3$) MS m/z: 443 ($MH^+$)

Example 91

N-[(2S)-3-Phenyl-1-pivaloyloxy-2-propyl]-2-[4-(2-aminoethoxy)-3-methoxyphenyl]acetamide (119)

The compound 119 was prepared by the same procedure with that described in above General Procedure D and the spectra were identical to that of compound 118.

mp: 71–76° C. [α]=−14.84 (c, 0.51, $CHCl_3$) MS m/z: 443 ($MH^+$)

Example 92

O-[2-(3,4-Dimethylbenzyl)-3-(pivaloyloxy)propyl]-N-[4-(methoxymethoxy)-3-methoxybenzyl] thiocarbamate (123)

The compound 123 was prepared by the same procedure with that described in above General Procedure E.

$^1$H-NMR ($CDCl_3$) δ: 6.75–7.15 (m, 6 H, Ar), 6.40 (bs, 1 H, NH), 5.22 (s, 2 H, $OCH_2O$), 4.66 (d, 2 H, J=5.4 Hz, $CH_2NH$), 4.48 (m, 2 H, $CH_2O$), 3.95–4.1 (m, 2 H, $CH_2OCO$), 3.88 (s, 3 H, $OCH_3$), 3.51 (s, 3 H, $OCH_3$), 2.6–2.75 (m, 2 H, $CH_2Ar$), 2.38 (s, 1 H, CH), 2.2–2.3 (m, 6 H, 2×$CH_3$), 1.21 (s, 9 H, $C(CH_3)_3$)

Example 93

O-12-(4-tert-Butylbenzyl)-3-(pivaloyloxy)propyl]-N-[4-(methoxymethoxy)-3-methoxybenzyl] thiocarbamate (124)

The compound 124 was prepared by the same procedure with that described in above General Procedure E.

$^1$H-NMR ($CDCl_3$) δ: 7.32 (d, 2H, J=8.3 Hz), 7.04 (d, 2 H, J=8.3 Hz), 6.75–7.0 (m, 3 H, Ar), 6.40 (bs, 1 H, NH), 5.22 (s, 2 H, $OCH_2O$), 4.66 (d, 2 H, J=5.4 Hz, $CH_2NH$), 4.48 (m, 2 H, $CH_2O$), 3.95–4.1 (m, 2 H, $CH_2OCO$), 3.88 (s, 3 H, $OCH_3$), 3.51 (s, 3 H, $OCH_3$), 2.6–2.75 (m, 2 H, $CH_2Ar$), 2.38 (s, 1 H, CH), 1.32 (s, 9 H, $C(CH_3)_3$), 1.21 (s, 9 H, $C(CH_3)_3$)

Example 94

N-(4-hydroxy-3-methoxybenzyl)-O-[2-(3,4-Dimethylbenzyl)-3-(pivaloyloxy)propyl] thiocarbamate (125)

The compound 125 was prepared by the same procedure with that described in above General Procedure B.

75% yield, yellow oil. $^1$H-NMR ($CDCl_3$) δ: 6.75–7.05 (m, 6 H, Ar), 6.38 (bs, 1 H, NH), 5.61 (s, 1 H, OH), 4.64 (d, 2 H, J=5.4 Hz, $CH_2NH$), 4.45 (m, 2 H, $CH_2O$), 3.95–4.1 (m, 2 H, $CH_2OCO$), 3.89 (s, 3 H, $OCH_3$), 2.6–2.75 (m, 2 H, $CH_2Ar$), 2.38 (s, 1 H, CH), 2.2–2.3 (m, 6 H, 2×$CH_3$), 1.21 (s, 9 H, $C(CH_3)_3$) MS m/z: 474 ($MH^+$)

Example 95

N-(4-hydroxy-3-methoxybenzyl)-O-[2-(4-tert-butylbenzyl)-3-(pivaloyloxy)propyl] thiocarbamate (126)

The compound 126 was prepared by the same procedure with that described in above General Procedure B.

72% yield, yellow oil. $^1$H-NMR ($CDCl_3$) δ: 7.32 (d, 2 H, J=8.3 Hz), 7.06 (d, 2 H, J=8.3 Hz), 6.75–7.0 (m, 3 H, Ar), 6.38 (bs, 1 H, NH), 5.61 (s, 1 H, OH), 4.64 (d, 2 H, J=5.4 Hz, $CH_2NH$), 4.45 (m, 2 H, $CH_2O$), 3.95–4.1 (m, 2 H, $CH_2OCO$), 3.89 (s, 3 H, $OCH_3$), 2.6–2.75 (m, 2 H, $CH_2Ar$), 2.38 (s, 1 H, CH), 1.32 (s, 9 H, $C(CH_3)_3$), 1.21 (s, 9 H, $C(CH_3)_3$) MS m/z: 502 ($MH^+$)

Example 96

O-[2-(3,4-Dimethylbenzyl)-3-(pivaloyloxy)propyl]-N-[4-(2-azidoethoxy)-3-methoxybenzyl] thiocarbamate (127)

The compound 125 was prepared by the same procedure with that described in above General Procedure E.

$^1$H-NMR ($CDCl_3$) δ: 6.75–7.15 (m, 6 H, Ar), 6.38 (bs, 1 H, NH), 5.22 (s, 2 H, $OCH_2O$), 4.66 (d, 2 H, J=5.4 Hz, $CH_2NH$), 4.18 (t, 2 H, J=5.4 Hz, $OCH_2CH_2N_3$), 3.95–4.1 (m, 2 H, $CH_2OCO$), 3.88 (s, 3 H, $OCH_3$), 3.62 (t, 2 H, J=5.4 Hz, $OCH_2CH_2N_3$), 2.6–2.75 (m, 2 H, $CH_2Ar$), 2.38 (s, 1 H, CH), 2.2–2.3 (m, 6 H, 2×$CH_3$), 1.21 (s, 9 H, $C(CH_3)_3$)

Example 97

O-[2-(4-tert-Butylbenzyl)-3-(pivaloyloxy)propyl]-N-[4-(2-azidoethoxy)-3-methoxybenzyl] thiocarbamate (128)

The compound 128 was prepared by the same procedure with that described in above General Procedure E.

$^1$H-NMR ($CDCl_3$) δ: 7.32 (d, 2 H, J=8.3 Hz), 7.06 (d, 2 H, J=8.3 Hz), 6.75–7.0 (m, 3 H, Ar), 6.38 (bs, 1 H, NH), 5.22 (s, 2 H, $OCH_2O$), 4.66 (d, 2 H, J=5.4 Hz, $CH_2NH$), 4.18 (t, 2 H, J=5.4 Hz, $OCH_2CH_2N_3$), 3.95–4.1 (m, 2 H, $CH_2OCO$), 3.88 (s, 3 H, $OCH_3$), 3.62 (t, 2 H, J=5.4 Hz, $OCH_2CH_2N_3$), 2.6–2.75 (m, 2 H, $CH_2Ar$), 2.38 (s, 1 H, CH), 1.32 (s, 9 H, $C(CH_3)_3$), 1.21 (s, 9 H, $C(CH_3)_3$)

Example 98

O-[2-(3,4-Dimethylbenzyl)-3-(pivaloyloxy)propyl]-N-[4-(2-aminoethoxy)-3-methoxybenzyl] thiocarbamate (129)

The compound 129 was prepared by the same procedure with that described in above General Procedure C.

$^1$H-NMR ($CDCl_3$) δ: 6.75–7.15 (m, 6 H, Ar), 6.38 (bs, 1 H, NH), 4.66 (d, 2 H, J=5.4 Hz, $CH_2NH$), 3.95–4.1 (m, 2 H, $CH_2OCO$), 3.98 (t, 2 H, J=5 Hz, $OCH_2CH_2NH_2$), 3.88 (s, 3 H, $OCH_3$), 3.11 (t, 2 H, J=5 Hz, $OCH_2CH_2NH_2$), 2.6–2.75 (m, 2 H, $CH_2Ar$), 2.5 (bs, 2 H, $NH_2$), 2.38 (s, 1 H, CH), 2.2–2.3 (m, 6 H, 2×$CH_3$), 1.21 (s, 9 H, $C(CH_3)_3$) MS m/z: 517 ($MH^+$)

Example 99

O-[2-(4-tert-Butylbenzyl)-3-(pivaloyloxy)propyl]-N-[4-(2-aminoethoxy)-3-methoxybenzyl] thiocarbamate (130)

The compound 130 was prepared by the same procedure with that described in above General Procedure C.

$^1$H-NMR ($CDCl_3$) δ: 7.32 (d, 2 H, J=8.3 Hz), 7.06 (d, 2 H, J=8.3 Hz), 6.75–7.0 (m, 3 H, Ar), 6.36 (bs, 1 H, NH), 4.64 (d, 2 H, J=5.4 Hz, $CH_2NH$), 3.95–4.1 (m, 2 H, $CH_2OCO$), 3.98 (t, 2 H, J=5 Hz, $OCH_2CH_2NH_2$), 3.88 (s, 3 H, $OCH_3$), 3.12 (t, 2 H, J=5 Hz, $OCH_2CH_2NH_2$), 2.6–2.75 (m, 2 H, $CH_2Ar$), 2.5 (bs, 2 H, $NH_2$), 2.38 (s, 1 H, CH), 1.32 (s, 9 H, $C(CH_3)_3$), 1.21 (s, 9 H, $C(CH_3)_3$) MS m/z: 545 ($MH^+$)

Example 100

O-(4-tert-Butylbenzyl)-N-[4-(methoxymethoxy)-3-methoxybenzyl]thiocarbamate (131)

The compound 131 was prepared by the same procedure with that described in General Procedure E.

$^1$H-NMR ($CDCl_3$) δ: 7.39 (d, 2 H, J=8.3 Hz), 7.32 (d, 2 H, J=8.3 Hz), 7.09 (d, 1 H, J=8.3 Hz, $Ar_{H-5}$), 6.89 (d, 1 H, J=1.95 Hz, $Ar_{H-2}$), 6.82 (dd, 1 H, J=8.3, 1.95 Hz, $Ar_{H-6}$), 6.50 (bs, 1 H, NH), 5.47 (s, 2 H, $ArCH_2O$), 5.20 (s, 2 H, $OCH_2O$), 4.68 (d, 2 H, J=5.6 Hz, $CH_2NH$), 3.86 (s, 3 H, $OCH_3$), 3.50 (s, 3 H, $OCH_3$), 1.32 (s, 9 H, $C(CH_3)_3$)

Example 101

O-(4-tert-Butylbenzyl)-N-(4-hydroxy-3-methoxybenzyl) thiocarbamate (132)

The compound 132 was prepared by the same procedure with that described in General Procedure B.

$^1$H-NMR ($CDCl_3$) δ: 7.30 (AB q, 4 H, J=8.5 Hz), 6.86 (d, 1 H, J=8 Hz, $Ar_{H-5}$), 6.73–6.79 (m, 2 H, $Ar_{H-2}$ and $Ar_{H-6}$), 5.58 (s, 1 H, OH), 5.51 (bs, 1 H, NH), 4.40 (d, 2 H, J=5.6 Hz, $CH_2NH$), 4.17 (s, 2 H, $ArCH_2O$), 3.87 (s, 3 H, $OCH_3$), 1.30 (s, 9 H, $C(CH_3)_3$). IR (KBr) 3334, 2962, 1651, 1515, 1274, 1200 $cm^{-1}$ MS m/z 360 ($MH^+$)

Example 102

O-(4-tert-Butylbenzyl)-N-[4-(2-azidoethoxy)-3-methoxybenzyl]thiocarbamate (133)

The compound 133 was prepared by the same procedure with that described in above General Procedure E.

$^1$H-NMR ($CDCl_3$) δ: 7.39 (d, 2H, J=8.3 Hz), 7.32 (d, 2 H, J=8.3 Hz), 7.09 (d, 1 H, J=8.3 Hz), 6.89 (d, 1 H, J 1.95 Hz), 6.82 (dd, 1 H, J=8.3, 1.95 Hz), 6.50 (bs, 1 H, NH), 5.20 (s, 2 H, $OCH_2O$), 4.68 (d, 2 H, J=5.6 Hz, $CH_2NH$), 4.18 (t, 2 H, J=5.4 Hz, $OCH_2CH_2N_3$), 3.86 (s, 3 H, $OCH_3$), 3.62 (t, 2 H, J=5.4 Hz, $OCH_2CH_2N_3$), 1.32 (s, 9 H, $C(CH_3)_3$).

Example 103

O-(4-tert-Butylbenzyl)-N-[4-(2-aminoethoxy)-3-methoxybenzyl]thiocarbamate (134)

The compound 134 was prepared by the same procedure with that described in above General Procedure C.

$^1$H-NMR ($CDCl_3$) δ: 7.39 (d, 2 H, J=8.3 Hz), 7.32 (d, 2 H, J=8.3 Hz), 7.09 (d, 1 H, J=8.3 Hz, $Ar_{H-5}$), 6.89 (d, 1 H, J=1.95 Hz, $Ar_{H-2}$), 6.82 (dd, 1 H, J=8.3, 1.95 Hz, $Ar_{H-6}$), 6.50 (bs, 1 H, NH), 5.20 (s, 2 H, $OCH_2O$), 4.68 (d, 2 H, J=5.6 Hz, $CH_2NH$), 3.98 (t, 2 H, J=4.9 Hz, $OCH_2CH_2NH_2$), 3.86 (s, 3 H, $OCH_3$), 3.12 (t, 2 H, J=4.9 Hz, $OCH_2CH_2NH_2$), 2.50 (bs, 2 H, $NH_2$), 1.32 (s, 9 H, $C(CH_3)_3$). MS m/z: 403 ($MH^+$)

Example 104

N-[2-(3,4-Dimethylbenzyl)-3-(pivaloyloxy)propyl]-O-[4-(methoxymethoxy)-3-methoxybenzyl] thiocarbamate (138)

The compound 138 was prepared by the same procedure with that described in above General Procedure E.

$^1$H-NMR ($CDCl_3$) δ: 6.85–7.15 (m, 6 H, Ar), 6.70 (bs, 1 H, NH), 5.40 (s, 2 H, $ArCH_2O$), 5.23 (s, 2 H, $OCH_2O$), 4.16 (ddd of AB, 2 H, $CH_2OCO$), 3.89 (s, 3 H, $OCH_3$), 3.51 (s, 3 H, $OCH_3$), 3.74 (m, 1 H, $CH_2NH$), 3.40 (m, 1 H, $CH_2NH$), 2.5–2.7 (m, 2 H, $CH_2Ar$), 2.35 (m, 1 H, CH), 2.2–2.3 (m, 6 H, 2×$CH_3$), 1.23 (s, 9 H, $C(CH_3)_3$)

Example 105

N-[2-(4-tert-Butylbenzyl)-3-(pivaloyloxy)propyl]-O-[4-(methoxymethoxy)-3-methoxybenzyl] thiocarbamate (139)

The compound 139 was prepared by the same procedure with that described in above General Procedure E.

$^1$H-NMR ($CDCl_3$) δ: 7.34 (d, 2H, J=8 Hz), 7.06 (d, 2 H, J=8 Hz), 6.85–7.0 (m, 3 H, Ar), 6.70 (bs, 1 H, NH), 5.40 (s, 2 H, $ArCH_2O$), 5.22 (s, 2 H, $OCH_2O$), 4.16 (ddd of AB, 2 H, $CH_2OCO$), 3.89 (s, 3 H, $OCH_3$), 3.51 (s, 3 H, $OCH_3$), 3.74 (m, 1 H, $CH_2NH$), 3.40 (m, 1 H, $CH_2NH$), 2.5–2.7 (m, 2 H, $CH_2Ar$), 2.35 (m, 1 H, CH), 1.34 (s, 9 H, $C(CH_3)_3$), 1.23 (s, 9 H, $C(CH_3)_3$)

Example 106

N-[2-(3,4-Dimethylbenzyl)-3-(pivaloyloxy)propyl]-O-(4-hydroxy-3-methoxybenzyl) thiocarbamate (140)

The compound 140 was prepared by the same procedure with that described in above General Procedure B.

$^1$H-NMR ($CDCl_3$) δ: 6.75–7.05 (m, 6 H, Ar), 5.70 (m, 1 H, NH), 5.55 (s, 1 H, OH), 4.10 (s, 2 H, $ArCH_2O$), 3.8–3.95 (m, 5 H, $OCH_3$ and $CH_2OCO$), 3.1–3.5 (m, 2 H, $CH_2NH$), 2.5–2.7 (m, 2 H, $CH_2Ar$), 2.1–2.3 (m, 7 H, 2×$CH_3$ and CH), 1.23 (s, 9 H, $C(CH_3)_3$). MS m/z: 474 ($MH^+$)

Example 107

N-[2-(4-tert-Butylbenzyl)-3-(pivaloyloxy)propyl]-O-(4-hydroxy-3-methoxybenzyl)thiocarbamate (141)

The compound 141 was prepared by the same procedure with that described in above General Procedure B.

$^1H$-NMR ($CDCl_3$) δ: 7.36 (d, 2 H, J=8.3 Hz), 7.12 (d, 2 H, J=8.3 Hz), 6.75–7.0 (m, 3 H, Ar), 5.70 (m, 1 H, NH), 5.53 (s, 1 H, OH), 4.10 (s, 2 H, $ArCH_2O$), 3.8–3.95 (m, 5 H, $OCH_3$ and $CH_2OCO$), 3.1–3.5 (m, 2 H, $CH_2NH$), 2.5–2.7 (m, 2 H, $CH_2Ar$), 2.10 (m, 1 H, CH), 1.34 (s, 9 H, $C(CH_3)_3$), 1.23 (s, 9 H, $C(CH_3)_3$). MS m/z: 502 ($MH^+$)

Example 108

N-[2-(3,4-Dimethylbenzyl)-3-(pivaloyloxy)propyl]-O-[4-(2-azidoethoxy)-3-methoxybenzyl] thiocarbamate (142)

The compound 142 was prepared by the same procedure with that described in above General Procedure E.

$^1H$-NMR ($CDCl_3$) δ: 6.85–7.15 (m, 6 H, Ar), 6.70 (bs, 1 H, NH), 5.40 (s, 2 H, $ArCH_2O$), 4.18 (t, 2 H, J=5.2 Hz, $OCH_2CH_2N_3$), 4.12 (ddd of AB, 2 H, $CH_2OCO$), 3.89 (s, 3 H, $OCH_3$), 3.74 (m, 1 H, $CH_2NH$), 3.62 (t, 2 H, J=5.2 Hz, $OCH_2CH_2N_3$), 3.40 (m, 1 H, $CH_2NH$), 2.5–2.7 (m, 2 H, $CH_2Ar$), 2.35 (m, 1 H, CH), 2.2–2.3 (m, 6 H, 2×$CH_3$), 1.23 (s, 9 H, $C(CH_3)_3$)

Example 109

N-[2-(4-tert-Butylbenzyl)-3-(pivaloyloxy)propyl]-O-[4-(2-azidoethoxy)-3-methoxybenzyl] thiocarbamate (143)

The compound 143 was prepared by the same procedure with that described in above General Procedure E.

$^1H$-NMR ($CDCl_3$) δ: 7.36 (d, 2 H, J=8.3 Hz), 7.18 (d, 2 H, J=8.3 Hz), 6.85–7.0 (m, 3 H, Ar), 6.68 (bs, 1 H, NH), 5.40 (s, 2 H, $ArCH_2O$), 4.18 (t, 2 H, J=5.2 Hz, $OCH_2CH_2N_3$), 4.12 (ddd of AB, 2 H, $CH_2OCO$), 3.88 (s, 3 H, $OCH_3$), 3.73 (m, 1 H, $CH_2NH$), 3.60 (t, 2 H, J=5.2 Hz, $OCH_2CH_2N_3$), 3.40 (m, 1 H, $CH_2NH$), 2.5–2.7 (m, 2 H, $CH_2Ar$), 2.34 (m, 1 H, CH), 1.34 (s, 9 H, $C(CH_3)_3$), 1.23 (s, 9 H, $C(CH_3)_3$)

Example 110

N-[2-(3,4-Dimethylbenzyl)-3-(pivaloyloxy)propyl]-O-[4-(2-aminoethoxy)-3-methoxybenzyl] thiocarbamate (144)

The compound 144 was prepared by the same procedure with that described in above General Procedure C.

$^1H$-NMR ($CDCl_3$) δ: 6.85–7.15 (m, 6 H, Ar), 6.68 (bs, 1 H, NH), 5.40 (s, 2 H, $ArCH_2O$), 4.12 (ddd of AB, 2 H, $CH_2OCO$), 3.98 (t, 2 H, J=5.2 Hz, $OCH_2CH_2NH_2$), 3.88 (s, 3 H, $OCH_3$), 3.74 (m, 1 H, $CH_2NH$), 3.39 (m, 1 H, $CH_2NH$), 3.10 (t, 2 H, J=5.2 Hz, $OCH_2CH_2NH_2$), 2.5–2.7 (m, 2 H, $CH_2Ar$), 2.5 (bs, 2 H, $NH_2$), 2.35 (m, 1 H, CH), 2.2–2.3 (m, 6 H, 2×$CH_3$), 1.22 (s, 9 H, $C(CH_3)_3$) MS m/z: 517 ($MH^+$)

Example 111

N-[2-(4-tert-Butylbenzyl)-3-(pivaloyloxy)propyl]-O-[4-(2-aminoethoxy)-3-methoxybenzyl] thiocarbamate (145)

The compound 145 was prepared by the same procedure with that described in above General Procedure C.

$^1H$-NMR ($CDCl_3$) δ: 7.32 (d, 2 H, J=8.3 Hz), 7.12 (d, 2 H, J=8.3 Hz), 6.85–7.0 (m, 3 H, Ar), 6.66 (bs, 1 H, NH), 5.40 (s, 2 H, $ArCH_2O$), 4.12 (ddd of AB, 2 H, $CH_2OCO$), 3.98 (t, 2 H, J=5.2 Hz, $OCH_2CH_2NH_2$), 3.88 (s, 3 H, $OCH_3$), 3.72 (m, 1 H, $CH_2NH$), 3.40 (m, 1 H, $CH_2NH$), 3.12 (t, 2 H, J=5.2 Hz, $OCH_2CH_2NH_2$), 2.5–2.7 (m, 4 H, $CH_2Ar$ and $NH_2$), 2.34 (m, 1 H, CH), 1.32 (s, 9 H, $C(CH_3)_3$), 1.22 (s, 9 H, $C(CH_3)_3$) MS m/z: 545 ($MH^+$)

Example 112

N-(4-tert-Butylbenzyl)-O-[4-(methoxymethoxy)-3-methoxybenzyl]thiocarbamate (146)

The compound 146 was prepared by the same procedure with that described in above General Procedure E.

$^1H$-NMR ($CDCl_3$) δ: 7.36 (d, 2 H, J=8.3 Hz), 7.25 (d, 2 H, J=8.3 Hz), 7.12 (d, 1 H, J=8 Hz, $Ar_{H-5}$), 6.9–6.95 (m, 2 H, $Ar_{H-2}$ and $Ar_{H-6}$), 6.51 (bs, 1 H, NH), 5.44 (s, 2 H, $ArCH_2O$), 5.22 (s, 2 H, $OCH_2O$), 4.72 (d, 2 H, J=5.4 Hz, $CH_2NH$), 3.88 (s, 3 H, $OCH_3$), 3.50 (s, 3 H, $OCH_3$), 1.31 (s, 9 H, $C(CH_3)_3$).

Example 113

N-(4-tert-Butylbenzyl)-O-(4-hydroxy-3-methoxybenzyl)thiocarbamate (147)

The compound 147 was prepared by the same procedure with that described in above General Procedure E.

$^1H$-NMR ($CDCl_3$) δ: 7.36 (d, 2 H, J=8.3 Hz), 7.20 (d, 2 H, J=8.3 Hz), 6.8–6.9 (m, 3 H), 5.55 (s, 1 H, OH), 5.53 (bs, 1 H, NH), 4.45 (d, 2 H, J=5.1 Hz, $CH_2NH$), 4.14 (s, 2 H, $CH_2O$), 3.87 (s, 3 H, $OCH_3$), 1.31 (s, 9 H, $C(CH_3)_3$). IR (KBr) 3360, 2961, 1652, 1513, 1268, 1200 $cm^{-1}$ MS(EI) m/z: 359 ($M^+$)

Example 106

N-(4-tert-Butylbenzyl)-O-[4-(2-azidomethoxy)-3-methoxybenzyl]thiocarbamate (148)

The compound 148 was prepared by the same procedure with that described in above General Procedure E.

$^1H$-NMR ($CDCl_3$) δ: 7.36 (d, 2 H, J=8.3 Hz), 7.20 (d, 2 H, J=8.3 Hz), 7.12 (d, 1 H, J=8 Hz), 6.9–6.95 (m, 2 H), 6.50 (bs, 1 H, NH), 5.44 (s, 2 H, $ArCH_2O$), 4.73 (d, 2 H, J=5.6 Hz, $CH_2NH$), 4.18 (t, 2 H, J=5.2 Hz, $OCH_2CH_2N_3$), 3.88 (s, 3 H, $OCH_3$), 3.62 (t, 2 H, J=5.2 Hz, $OCH_2CH_2N_3$), 1.31 (s, 9 H, $C(CH_3)_3$).

Example 107

N-(4-tert-Butylbenzyl)-O-[4-(2-aminomethoxy)-3-methoxybenzyl]thiocarbamate (149)

The compound 149 was prepared by the same procedure with that described in above General Procedure C.

$^1H$-NMR ($CDCl_3$) δ: 7.32 (d, 2 H, J=8.3 Hz), 7.16 (d, 2 H, J=8.3 Hz), 7.10 (d, 1 H, J=8 Hz), 6.9–6.95 (m, 2 H), 6.50 (bs, 1 H, NH), 5.44 (s, 2 H, $ArCH_2O$), 4.73 (d, 2 H, J=5.6 Hz, $CH_2NH$), 4.0 (t, 2 H, J=5.2 Hz, $OCH_2CH_2NH_2$), 3.88 (s, 3 H, $OCH_3$), 3.12 (t, 2 H, J=5.2 Hz, $OCH_2CH_2NH_2$), 1.31 (s, 9 H, $C(CH_3)_3$). MS m/z: 403 ($MH^+$)

Experimental Example 1

Receptor Binding Affinity Assay

The VR receptor binding affinity activity of the target compounds was measured by an in vitro receptor binding. In the receptor binding assay, the compounds were evaluated for their ability to displace bound [$^3H$]RTX from the receptor. The results are expressed in terms of $K_i$ values (mean±SEM, 3 experiments) which represent the concentration of the non-radioactive ligand that displaces half of the bound labeled RTX.

Methods

Preparation

The VR receptor binding affinity activity of the inventive compounds was measured by using Chinese Hamster Ovary (CHO, ATCC, No. CCL-61) cell whose cDNA of VR1 (pUHG102 VR1 plasmid) was transfected, which can control the expression of VR1 according to the presence of tetracycline and Tetracycline on/off system (pTet off regulatory plasmid, Clontech. Inc., USA) that the expression of VR1 is induced by removing tetracycline from the medium. CHO cells were cultured in the medium containing 1 μg/ml of tetracycline (T-7660, Sigma-Aldrich. Co., USA) and 10 μg/ml of puromycin for stabilizing the cell line. The cells were cultured after removing tetracycline prior to 48 hours. The tetracycline free culture medium was seeded at the bottom of T75 flask, incubated to the extent that its density reaches at 90%, and washed once with PBS buffer solution. The cells were collected by using saline solution containing 5 mM EDTA and subjected to centrifugation slightly to obtain precipitates, further, which had been kept at the temperature of −20° C. before use.

Resiniferatoxin Binding Assay.

[$^3$H] RTX binding assay of present invention was performed with the procedure described in the literature (Szallasi et al.; *Pharmacol. Exp. Ther.,* 262, pp883–888, 1992).

Experiments were designed to assess inhibition of specific [$^3$H]RTX binding to membranes by non-radioactive compounds. The binding assay mixture containing [$^3$H]RTX (80 pM), various concentrations of competitive binding substances, 0.25 mg/ml of BSA(Cohn fraction V), $5\times10^4$~$5\times10^5$ numbers of VR1 and the expression cell, was admixed with saline solution containing 450 μl of $Ca^{2+}$ and $Mg^{2+}$ and 0.25 mg/μl of BSA. Non-specific binding assay was measured after mixing 100 nM of non-radioactive RTX thereto. The reaction mixture was treated for 60 min at 37° C. and the reaction was quenched by cooling over ice. RTX bound to the membrane of VR1 was subjected to centrifugation with maximum velocity for 15 minutes to precipitate its membrane residue, which results in separating from non-binding RTX. The tips of tube containing above precipitate was cut off and the amount of bound radioisotope was determined by scintillation counter (LS6500, Beckman-Coulter, USA). The measurement of binding was determined in triplicate in each experiment, and each experiment was repeated at least two times. Binding data were analyzed by fitting to the Hill equation and the Ki (equilibrium binding parameter) index, the Bmax (maximum binding parameter) index, and the cooperativity index etc., were determined by using origin 6.0 program (Origin, MicroCal Co., USA).

The Preparation of Sample

An initial compound was dissolved in DMSO(dimethyl sulfoxide) and diluted with saline solution containing $Ca^{2+}$ and $Mg^{2+}$, and 0.25 mg/μl of BSA.

Result

As can be seen in Table 1, most of tested compounds showed stronger agonistic activity and receptor binding affinity than that of CAP. Among them, the thiourea analogues, compound 28 (Ki=24.95 nM), compound 29 (Ki=18.28 nM) and compound 63 (Ki=34.58 nM) exhibited more potent agonistic activity than that of amide and thiocarbamate analogues. The 4-t-Bu group at $R_1$ substituent and the pivaloyl group are proved to be effective hydrophobic groups resulting in optimal agonistic activity showed more potent activity than that of CAP.

TABLE 1

| Binding Affinities | | | | | | |
|---|---|---|---|---|---|---|
| No. | Compound | $R_1$ | $R_2$ | m | n | Binding Affinity (Ki = nM) |
| JYL-79 | Thiourea | 3,4-$Me_2$ | H | 1 | 1 | 17.43(±1.09) |
| JYL-273 | | 4-t-Bu | H | 1 | 1 | 6.35(±0.48) |
| 28 | | 3,4-$Me_2$ | H | 1 | 2 | 24.95(±4.43) |
| 29 | | 4-t-Bu | H | 1 | 2 | 18.28(±5.6) |
| 62 | | 3,4-$Me_2$ | H | 0 | 1 | 45.3(±18.2) |
| 63 | | 4-t-Bu | H | 0 | 1 | 34.58(±9.64) |
| 64 | | 3,4-$Me_2$ | H | 0 | 2 | 244.5(±87.7) |
| 75 | | 4-t-Bu | $(CH_2)_2NH_2$ | 0 | 1 | 341(±160) |
| LJO-198 | Amide | 3,4-$Me_2$ | H | 1 | 1 | 157(56) |
| 34 | | 3,4-$Me_2$ | H | 1 | 2 | 152.9(±6.9) |
| 35 | | 4-t-Bu | H | 1 | 2 | 36.34(±11.6) |
| MSK-195 | | 3,4-$Me_2$ | $(CH_2)_2NH_2$ | 1 | 1 | 603(±118) |
| 38 | | 3,4-$Me_2$ | $(CH_2)_2NH_2$ | 1 | 2 | 855(±45.9) |
| 125 | Thio-carbamate | | | | | 143(±3) |
| 132 | | | | | | 1956(±272) |
| 140 | | | | | | 156(±43) |
| 147 | | | | | | 1940(±224) |
| Capsaicin | | | | | | 1808(±270) |

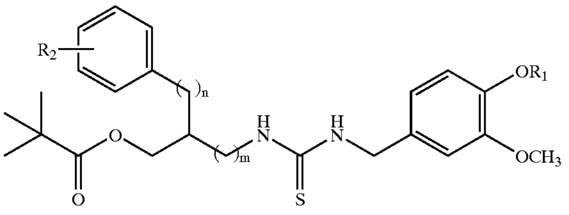

Thiourea

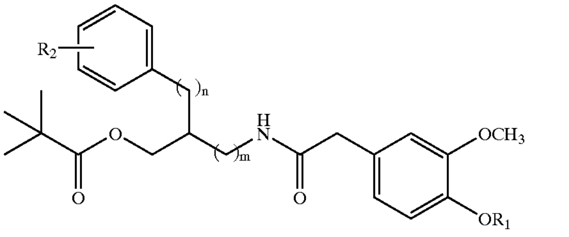

Amide

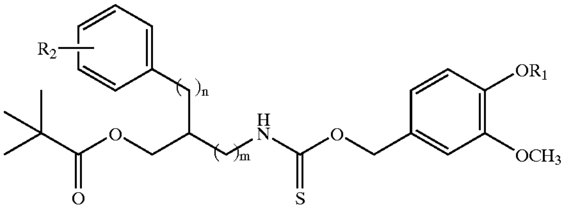

Thiocarbamate

Experimental Example 2

$^{45}$Ca Influx Test

Method

The $^{45}$Ca Influx test by using CHO cells expressing VR1 was performed by the procedure described in the literature (Lee, J. W., *Bioorganic & Medicinal Chemistry,* pp1713–1720, 2001).

The $^{45}$Ca Influx test by using CHO cells of the inventive compounds was measured by using Chinese Hamster Ovary (CHO, ATCC, No. CCL-61) cell whose cDNA of VR1 (pUHG102 VR1 plasmid) was transfected, which can control the expression of VR1 according to the presence of tetracycline and Tetracyclin on/off system (pTet off regulatory plasmid, Clontech. Inc., USA) that the expression of VR1 is induced by removing tetracycline from the medium.

The CHO cells were poured onto 24 well plates to the extent that its density reaches at 30% and incubated for 24 hours at 37° C. The culture medium was exchanged to tetracycline free medium to induce the expression of VR1 and tested after 36 hours.

In radioactive $^{45}Ca$ uptake experiment, The cells were incubated in 500 $\mu$l of DMEM medium (Dulbecco's modified Eagles medium: Gibco-BRL, 31600-083) containing free of serum and 1.8 mM $CaCl_2$ for 10 minutes at 37° C. Together with 0.25 mg/ml BSA (Sigma A2153, USA), 1 Ci/ml $^{45}Ca$(5–30 Ci/g used, ICN. Co., 62005 RT, U.S.A.), the test samples with increasing concentrations were added to each well. At the quenching moment of the incubation with $^{45}Ca$, the cultured cells were removed from the medium, washed three times with cool PBS buffer solution containing 1.8 mM $CaCl_2$ and 400 $\mu$l of RIPA buffer solution (50 mM Tris pH 7.4; 150 mM sodium chloride; 0.1% SDS; 1% sodium deoxycholate), was added in each well to homogenize the cells. The plates were stirred for 20 minutes slowly and 300 $\mu$l of cell lysate was transferred to scintillation vials from each wells. The radioactivity was determined by scintillation counter.

The data were assessed by determining four wells per each data point in each experiment and analyzed in computer by being transformed into Hill equation. The compounds named JYL-79 and JYL-273 described in prior arts (KP348819, PCT/KR00/00137), were used as control groups. The experiments were determined in triplicate in each sample comprising inventive compounds and control groups. The result is shown in Table 2.

Result

The $EC_{50}$ of compound 34 in the present invention was 0.784 nM, which showed 16 fold stronger effect than that of LJO-198 as a control group, 4 fold ($EC_{50}$=0.784 nM) than that of JYL-273 (KP348819, WO0050387) which is most active compound in prior art and 57 fold than that of commercially available capsaicin, respectively. The thiocarbamate compound 140 in present invention exhibited potent agonistic effect ($EC_{50}$=2.4 nM).

As cab be seen from Table 2, the agonistic effect of present invention is proved to be most potent among those of conventional VR agonists.

TABLE 2

Calcium Influx Assay

| No. | Compound | $R_1$ | $R_2$ | m | n | $^{45}Ca$ Influx ($EC_{50}$ = $\mu$M) |
|---|---|---|---|---|---|---|
| JYL-79 | Thiourea | 3,4-$Me_2$ | H | 1 | 1 | 3.29(±1.45) |
| JYL-273 | | 4-t-Bu | H | 1 | 1 | 3.07(±0.16) |
| 28 | | 3,4-$Me_2$ | H | 1 | 2 | 6.21(±2.18) |
| 29 | | 4-t-Bu | H | 1 | 2 | 18.7(±4.2) |
| 62 | | 3,4-$Me_2$ | H | 0 | 1 | 19.62(±4.85) |
| 63 | | 4-t-Bu | H | 0 | 1 | 5.68(±2.12) |
| 64 | | 3,4-$Me_2$ | H | 0 | 2 | 2.367(±0.395) |
| 75 | | 4-t-Bu | $(CH_2)_2NH_2$ | 0 | 1 | 82.44(±30.4) |
| LJO-198 | Amide | 3,4-$Me_2$ | H | 1 | 1 | 12.67(±3.5) |
| 34 | | 3,4-$Me_2$ | H | 1 | 2 | 0.784(±0.25) |
| 35 | | 4-t-Bu | H | 1 | 2 | 8.44(±2.90) |
| MSK-195 | | 3,4-$Me_2$ | $(CH_2)_2NH_2$ | 1 | 1 | 239.8(±47.8) |
| 38 | | 3,4-$Me_2$ | $(CH_2)_2NH_2$ | 1 | 2 | 206.3(±29.4) |
| 125 | Thiocarbamate | | | | | 11.9(±4) |
| 132 | | | | | | 376.4(±22.4) |
| 140 | | | | | | 2.4(±0.1) |
| 147 | | | | | | 176.6(±18.8) |
| Capsaicin | | | | | | 44.75(±3.79) |

Experimental Example 3

Acetic Acid-induced Writhing Test

Method

The acetic acid-inducing writhing test for testing the analgesic activity of inventive compounds prepared from above Examples was performed by the procedure described in the literature (Lee, J. W., *Bioorganic & Medicinal Chemistry*, pp1713–1720, 2001).

Male ICR mice having its mean body weight of 25 g(CD-1; Biogenomics Co. Korea) were reared in lighting controlled environment (12 hrs on/12 hrs off) and fasted overnight prior to testing. 1.2% acetic acid solution (1.2%) was administrated in the mice intraperitoneally and then, 5 minutes later, the number of abdominal constrictions was counted for 20 minutes. Each group consisting of ten mice was pretreated with test compounds or solvent (0.2 ml, i.p.) 1 hour before the injection of acetic acid. Test compounds were dissolved in ethanol/Tween-80/saline (10/10/80). Analgesic activity was expressed as the reduction in the number of abdominal constrictions, of control animals (vehicle-pretreated mice) and animals pretreated with test compounds. $ED_{50}$, the concentration of the test group reducing 50% of the number of writhes and the result was shown in Table 3.

Result

While the activity of JYL-273 (KP348819, PCT/WO0050387), most analgesic compound in prior art, showed 13 fold stronger effect (0.1071 $\mu$g/Kg) than that of capsaicin, the compound 62 ($ED_{50}$=0.006 $\mu$g/Kg), compound 63 ($ED_{50}$=0.00036 $\mu$g/Kg), compound 74 ($ED_{50}$=0.00003 $\mu$g/Kg) and compound 75 ($ED_{50}$=0.00061 $\mu$g/Kg) in present invention, exhibited 224, 3,733, 44,800 and 2,203 fold stronger effect than that of capsaicin, respectively. It shows that the analgesic effects of inventive compounds are proved to be most potent in conventional vanilloid receptor agonists.

The test results demonstrated that analgesic effect of the compounds used in this experiment is potent, and in particular, it is significant to clarify that vanilloid receptor agonist can exhibit such potent analgesic effect, and the result suggests that vanilloid receptor agonist has potential as an analgesic agent.

TABLE 3

| | | | Writhing test | | | | |
|---|---|---|---|---|---|---|---|
| No. | Compound | $R_1$ | $R_2$ | m | n | Writhing Test ($ED_{50}$ = $\mu$G/KG) | Relative effect |
| JYL-79 | Thiourea | 3,4-$Me_2$ | H | 1 | 1 | 0.161 | 8 |
| JYL-273 | | 4-t-Bu | H | 1 | 1 | 0.107 | 12 |
| 62 | | 3,4-$Me_2$ | H | 0 | 1 | 0.006 | 224 |
| 63 | | 4-t-Bu | H | 0 | 1 | 0.00036 | 3733 |
| 74 | | 3,4-$Me_2$ | H | 0 | 2 | 0.00003 | 44800 |
| 75 | | 4-t-Bu | $(CH_2)_2NH_2$ | 0 | 1 | 0.00061 | 2203 |
| LJO-198 | Amide | 3,4-$Me_2$ | H | 1 | 1 | 0.0235 | 57 |
| 34 | | 3,4-$Me_2$ | H | 1 | 2 | 0.934 | 1.4 |
| MSK-195 | | 3,4-$Me_2$ | $(CH_2)_2NH_2$ | 1 | 1 | 1.171 | 1.1 |
| 38 | | 3,4-$Me_2$ | $(CH_2)_2NH_2$ | 1 | 2 | 0.076 | 18 |
| Capsaicin | | | | | | 1.344 | 1 |

Experimental Example 4

Pungency in the Rat Eye-wiping Test

The focus of medicinal chemistry in developing vanilloid-derived therapeutics has been the improvement of the bioavailability and the reduction of the excitatory properties. In connection with these objectives, the rat eye-wiping test was employed as an in vivo pungency test to assess the pain-producing effects of the compounds.

Methods

The pain-inducing potency of the compounds was determined in the eye-wiping assay as previously described, and expressed quantitatively as follows.

Male Sprague-Dawley rat (mean body weight 150 g) were reared in a controlled environment at the temperatures of 22±2° C., at the humidity of 50±5% at the condition of 12 hours light(6 a.m.~6 p.m.) and dark cycle. Groups of SD rat were fasted with free access to water and meal, and adjusted for 30 minutes prior to testing. The test compounds were dissolved in ethanol/Tween-80/saline (10/10/80) or mixture solution of cremophor EL/DMSO/distilled water (10/10/80). Rats were put into transparent acryl box (29×19×18) and adjusted for 12 minutes. The test samples were dropped into left eye in the amount of 20 $\mu$l/eye, and the number of rat protective response (eye-wiping with the foreleg) was counted. Each concentration of samples was applied to each 6 rats and the dose-response curves were obtained from the mean values of respective concentrations.

From the dose-response curves, the concentration corresponding to a moderate pain-producing potency (MPP), i.e. inducing 10 times wipings, was calculated for each compound. On the basis of these concentrations, the relative pain-producing potency (RPP) was determined as compared to that of capsaicin, which was taken as 100 (Table 4).

Results

The characteristic of inventive compounds is that it works as vanilloid receptor agonist, but the strength of its pungency is much lower than that of capsaicin. When relative values of respective sample were defined as relative pain-producing potency (RPP) compared to that of capsaicin, which was taken as 100, the RPP values of compounds 74, 75 and 38 in the present invention, showed about 9, 3.4 and 5.5, respectively. It shows that the pungency of inventive compounds is proved to be the lowest pain-inducing potency in the conventional vanilloid receptor agonist which has been reported as pharmacologically effective synthetic compounds whose activities are identified by way of vanilloid receptor mechanism till now.

TABLE 4

| | | | Eye-Wiping Test | | | | |
|---|---|---|---|---|---|---|---|
| No. | Compound | $R_1$ | $R_2$ | m | n | MPP* ($\mu$g/ml) | RPP** |
| JYL-79 | Thiourea | 3,4-$Me_2$ | H | 1 | 1 | 1.7 | 94 |
| JYL-273 | | 4-t-Bu | H | 1 | 1 | 23 | 7 |
| 62 | | 3,4-$Me_2$ | H | 0 | 1 | 11.57 | 14 |
| 74 | | 3,4-$Me_2$ | H | 0 | 2 | 18.02 | 9 |
| 75 | | 4-t-Bu | $(CH_2)_2NH_2$ | 0 | 1 | 47 | 3.4 |
| MSK-195 | Amide | 3,4-$Me_2$ | $(CH_2)_2NH_2$ | 1 | 1 | 14.9 | 11 |
| 38 | | 3,4-$Me_2$ | $(CH_2)_2NH_2$ | 1 | 2 | 29 | 5.5 |
| Capsaicin | | | | | | 1.6 | 100 |

MPP*: moderate pain-producing potency
RPP**: relative pain-producing potency

Experimental Example 5

Toxicity Test

Methods

The acute toxicity tests on ICR mice (mean body weight 25±5 g) and Sprague-Dawley rats (235±10 g) were performed using the compounds 62, 38 and 140. Each group consisting of 3 mice or rats was administrated intraperitoneally with 20 mg/kg, 10 mg/kg and 1 mg/kg of test compounds or solvents (0.2 ml, i.p.), respectively and observed for 24 hrs.

Results

There were no treatment-related effects on mortality, clinical signs, body weight changes and gross findings in any group or either gender. These results suggested that the compounds prepared in the present invention were potent and safe.

Hereinafter, the formulating methods and kinds of excipients will be described, but the present invention is not limited to them. The representative preparation examples were described as follows.

Preparation of Powder

| | |
|---|---|
| Compound 28 | 500 mg |
| Corn Starch | 100 mg |
| Lactose | 100 mg |
| Talc | 10 mg |

Powder preparation was prepared by mixing above components and filling sealed package.

Preparation of Tablet

| | |
|---|---|
| Compound 34 | 100 mg |
| Corn Starch | 100 mg |
| Lactose | 100 mg |
| Magesium stearate | 2 mg |

Tablet preparation was prepared by mixing above components and entabletting.

Preparation of Capsule

| | |
|---|---|
| Compound 38 | 50 mg |
| Lactose | 50 mg |
| Magnesium stearate | 1 mg |

Tablet preparation was prepared by mixing above components and filling gelatin capsule by conventional gelatin preparation method.

Preparation of Injection

| | |
|---|---|
| Compound 62 | 100 mg |
| Distilled water for injection | optimum amount |
| PH controller | optimum amount |

Injection preparation was prepared by dissolving active component, controlling pH to about 7.5 and then filling all the components in 2 ml ample and sterilizing by conventional injection preparation method.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A compound represented by the following formula (I):

(I)

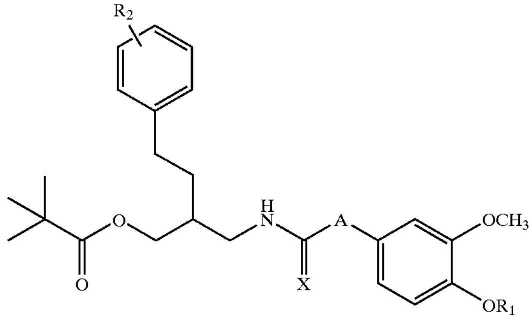

wherein,

X is a sulfur atom; A is —$NHCH_2$—; $R_1$ is a hydrogen atom or an aminoethyl group; $R_2$ is selected from the group consisting of a hydrogen, a halogen atom and an alkyl group having 1 to 6 carbon atoms.

2. A compound, which is selected from the group of consisting of:

N-[4-(3,4-dimethylphenyl)-2-(pivaloyloxymethyl)butyl]-N'-[4-hydroxy-3-methoxybenzyl]thiourea, and N-[4-t-butylphenyl-2-(pivaloyloxymethyl)butyl]-N'-[4-hydroxy-3-methoxybenzyl]thiourea.

3. A compound represented by the following formula (I):

(I)

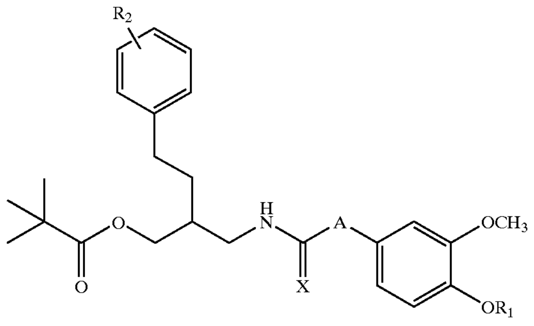

wherein,

X is an oxygen atom; A is —$NHCH_2$—; $R_1$ is a hydrogen atom or aminoethyl group; $R_2$ is selected from the group consisting of a hydrogen, a halogen atom and an alkyl group having 1 to 6 carbon atoms.

4. A compound, selected from the group consisting of:

N-[4-(3,4-dimethylphenyl-2-(pivaloyloxymethyl)butyl)-N'-[4-hydroxy-3-methoxybenzyl]urea, and N-[4-t-dimethylphenyl-2-(pivaloyloxymethyl)butyl]-N'-[4-hydroxy-3-methoxybenzyl]urea.

5. A compound represented by the following formula (II):

(II)

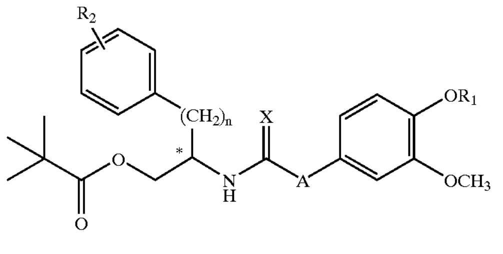

wherein,

X is an oxygen or sulfur atom; A is —$NHCH_2$— or —$CH_2$—; $R_1$ is a hydrogen atom, an aminoethyl or an alkoxyalkyl group having 1 to 6 carbon atoms; $R_2$ is selected from the group consisting of a hydrogen, halogen atom and alkyl group having 1 to 6 carbon atoms;

n is an integer of 1 to 3;

the asterisk mark * indicates a chiral carbon atom, and their pharmaceutically acceptable salts.

6. A compound selected from the group consisting of:

N-[3-(3,4-dimethylphenyl)-1-pivaloyloxy-2-propyl]-N'-[4-hydroxy-3-methoxybenzyl]thiourea, N-3-(4-t-butylphenyl)-1-pivaloyloxy-2-propyl]-N'-[4-hydroxy-3-methoxybenzyl]thiourea, N-[4-(3,4-dimethylphenyl)-1-pivaloyloxy-2-butyl]-N'-[4-hydroxy-3-methoxybenzyl]thiorea, N-[3-(3,4-dimethylphenyl)-1-pivaloyloxy-2-propyl]-N'-[4-hydroxy-3-methoxybenzyl]urea, N-[3-(4-t-dimethylphenyl)-1-pivaloyloxy-2-propyl]-N'-[4-hydroxy-3-methoxybenzyl]urea, N-[4-(3,4-dimethylphenyl)-1-pivaloyloxy-2-butyl]-N'-[4-hydroxy-3-methoxybenzyl]urea, N-[3-(3,4-dimethylphenyl)-1-pivaloyloxy-2-propyl]-N'-[4-(2-aminoethoxy)3-methoxybenzyl]thiourea, N-[3-(4-t-dimethylphenyl)-1-pivaloyloxy-2-propyl]-N'-[4-(2-aminoethoxy)3-methoxybenzyl]thiourea, N-[4-(3,4-dimethylphenyl)-1-pivaloyloxy-2-propyl]-N'-[4-(2-aminoethoxy)3-methoxybenzyl]thiourea, N-[3-(3,4-dimethylphenyl)-1-pivaloyloxy-2-propyl]-N'-[4-(2-aminoethoxy)3-methoxybenzyl]urea, N-[3-(4-t-dimethylphenyl)-1-pivaloyloxy-2-propyl]-N'-[4-(2-aminoethoxy)3-methoxybenzyl]urea, N-[4-(3,4-dimethylphenyl)-1-pivaloyloxy-2-propyl]-N'-[4-(2-aminoethoxy)3-methoxybenzyl]urea, N-[3-(3,4-dimethylphenyl)-1-pivaloyloxy-2-propyl]-2-[4-hydroxy-3-methoxyphenyl]acetamide, N-[3-(4-t-dimethylphenyl)-1-pivaloyloxy-2-propyl]-2-[4-hydroxy-3-methoxyphenyl]acetamide, N-[4-(3,4-dimethylphenyl)-1-pivaloyloxy-2-propyl]-2-[4-hydroxy-3-methoxyphenyl]acetamide, N-[3-(3,4-dimethylphenyl)-1-pivaloyloxy-2-propyl]-2-[4-(2-aminoethoxy)-3-methoxyphenyl]acetamide, N-[3-(4-t-dimethylphenyl)-1-pivaloyloxy-2-propyl]-2-[4-(2-aminoethoxy)-3-methoxyphenyl]acetamide, N-[4-(3,4-dimethylphenyl)-1-pivaloyloxy-2-propyl]-2-[4-(2-aminoethoxy)-3-methoxyphenyl]acetamide, N-[(2R)-3-phenyl-1-pivaloyloxy-2-propyl]-N'-[4-hydroxy-3-methoxybenzyl]thiourea, N-[(2S)-3-phenyl-1-pivaloyloxy-2-propyl]-N'-[4-hydroxy-3-methoxybenzyl]thiourea, N-[(2R)-3-phenyl-1-pivaloyloxy-2-propyl]-N'-[4-hydroxy-3-methoxybenzyl]urea, N-[(2S)-3-phenyl-1-pivaloyloxy-2-propyl]-N'-[4-hydroxy-3-methoxybenzyl]urea, N-[(2R)-3-phenyl-1-pivaloyloxy-2-propyl]-N'-[4-(2-aminoethoxy)-3-methoxybenzyl]thiourea, N-[(2S)-3-phenyl-1-pivaloyloxy-2-propyl]-N'-[4-(2-aminoethoxy)-3-methoxybenzyl]thiourea, N-[(2R)-3-phenyl-1-pivaloyloxy-2-propyl]-N'-[4-(2-aminoethoxy)-3-methoxybenzyl]urea, N-[(2S)-3-phenyl-1-pivaloyloxy-2-propyl]-N'-[4-(2-aminoethoxy)-3-methoxybenzyl]urea, N-[(2R)-3-phenyl-1-pivaloyloxy-2-propyl]-2-[4-hydroxy-3-methoxyphenyl]acetamide, N-[(2S)-3-phenyl-1-pivaloyloxy-2-propyl]-2-[4-hydroxy-3-methoxyphenyl]acetamide, N-[(2R)-3-phenyl-1-pivaloyloxy-2-propyl]-2-[4-(2-aminoethoxy)-3-methoxyphenyl]acetamide, and N-[(2S)-3-phenyl-1-pivaloyloxy-2-propyl]-2-[4-(2-aminoethoxy)-3-methoxyphenyl]acetamide.

7. The compound of claim 5, wherein X is a sulfur atom; A is —$NHCH_2$—; $R_1$ is a hydrogen atom or aminoethyl group; $R_2$ is a hydrogen or halogen atom or an alkyl group having 1 to 6 carbon atoms; n is an integer of 1 or 2.

8. The compound of claim 5, wherein X is an oxygen atom; A is —$CH_2$—; $R_1$ is a hydrogen atom or an aminoethyl group; $R_2$ is a hydrogen or halogen atom or an alkyl group having 1 to 6 carbon atoms; n is an integer of 1 or 2.

9. The compound of claim 5, wherein X is an oxygen atom; A is —$NHCH_2$—; $R_1$ is a hydrogen atom or an aminoethyl group; $R_2$ is a hydrogen or halogen atom or an alkyl group having 1 to 6 carbon atoms; n is an integer of 1 or 2.

10. A method for alleviating and/or treating pain, acute pain, chronic pain, neuropathic pain, post-operative pain, migraine, arthralgia or urgent urinary incontinence, comprising administering a therapeutically effective amount of a compound according to one of claims 1, 3, 2, 5, 6 or 4 or the salt or pharmaceutically acceptable hydrate thereof to a subject in need thereof.

11. A method of alleviating or relieving acute, chronic, inflammatory or neuropathic pains of suppressing inflammation or treating urge incontinence with comprises administering a compound according to one of claims 1, 3, 2, 5, 6 or 4 or the salt or pharmaceutically acceptable hydrate thereof to a subject in need thereof, as agonists of vanilloid receptors.

* * * * *